(12) United States Patent
Murray et al.

(10) Patent No.: US 8,012,900 B2
(45) Date of Patent: *Sep. 6, 2011

(54) NANO-LINKED METALLOCENE CATALYST COMPOSITIONS AND THEIR POLYMER PRODUCTS

(75) Inventors: Rex E. Murray, Bartlesville, OK (US); Kumudini C. Jayaratne, Groningen (NL); Qing Yang, Bartlesville, OK (US); Joel L. Martin, Bartlesville, OK (US)

(73) Assignee: Chevron Phillips Chemical Company, L.P., The Woodlands, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/965,982

(22) Filed: Dec. 28, 2007

(65) Prior Publication Data

US 2009/0170691 A1   Jul. 2, 2009

(51) Int. Cl.
*C07F 17/02* (2006.01)

(52) U.S. Cl. .......... 502/62; 502/102; 502/117; 502/150; 502/160; 526/161; 526/170; 526/136; 526/172

(58) Field of Classification Search ................ 526/113, 526/114, 115, 116; 502/62
See application file for complete search history.

(56) References Cited

U.S. PATENT DOCUMENTS

| | | |
|---|---|---|
| 3,242,099 A | 3/1966 | Manyik |
| 3,248,179 A | 4/1966 | Norwood |
| 4,060,480 A | 11/1977 | Reed |
| 4,452,910 A | 6/1984 | Hopkins |
| 4,501,885 A | 2/1985 | Sherk |
| 4,588,790 A | 5/1986 | Jenkins |
| 4,794,096 A | 12/1988 | Ewen |
| 4,808,561 A | 2/1989 | Welborn |
| 5,153,776 A | 10/1992 | Nozawa |
| 5,352,749 A | 10/1994 | DeChellis |
| 5,369,194 A | 11/1994 | Cribbs |
| 5,376,611 A | 12/1994 | Shveima |
| 5,436,304 A | 7/1995 | Griffin |
| 5,455,314 A | 10/1995 | Burns |
| 5,470,927 A | 11/1995 | Turner |
| 5,473,020 A | 12/1995 | Peifer |
| 5,492,973 A | 2/1996 | Peifer |
| 5,492,974 A | 2/1996 | Peifer |
| 5,492,975 A | 2/1996 | Peifer |
| 5,565,175 A | 10/1996 | Hottovy |
| 5,575,979 A | 11/1996 | Hanson |
| 5,576,259 A | 11/1996 | Hasegawa |

(Continued)

FOREIGN PATENT DOCUMENTS

EP   0985677 A1   3/2000

(Continued)

OTHER PUBLICATIONS

Jesus Cano Sierra et al. "Formation of Dinuclear Titanium and Zirconium Complexes by Olefin Metathesis_Catalytic Preparation of Organometallic Catalyst Systems".2003.*

(Continued)

*Primary Examiner* — Melvin C Mayes
*Assistant Examiner* — Colette Nguyen
(74) *Attorney, Agent, or Firm* — Merchant & Gould, P.C.

(57) ABSTRACT

The present invention provides polymerization catalyst compositions employing novel dinuclear metallocene compounds. Methods for making these new dinuclear metallocene compounds and for using such compounds in catalyst compositions for the polymerization and copolymerization of olefins are also provided.

32 Claims, 3 Drawing Sheets

U.S. PATENT DOCUMENTS

| | | | |
|---|---|---|---|
| 5,807,938 | A | 9/1998 | Kaneko |
| 5,869,586 | A | 2/1999 | Riedel |
| 5,919,983 | A | 7/1999 | Rosen |
| 6,010,974 | A * | 1/2000 | Kim et al. ............ 502/152 |
| 6,107,230 | A | 8/2000 | McDaniel |
| 6,153,776 | A | 11/2000 | Patton et al. |
| 6,165,929 | A | 12/2000 | McDaniel |
| 6,228,790 | B1 | 5/2001 | Ting |
| 6,235,917 | B1 | 5/2001 | Graf et al. |
| 6,239,235 | B1 | 5/2001 | Hottovy |
| 6,262,191 | B1 | 7/2001 | Hottovy |
| 6,274,752 | B1 | 8/2001 | Marks et al. |
| 6,291,695 | B1 | 9/2001 | Marks et al. |
| 6,294,494 | B1 | 9/2001 | McDaniel |
| 6,300,271 | B1 | 10/2001 | McDaniel |
| 6,316,553 | B1 | 11/2001 | McDaniel |
| 6,355,594 | B1 | 3/2002 | McDaniel |
| 6,376,415 | B1 | 4/2002 | McDaniel |
| 6,388,017 | B1 | 5/2002 | McDaniel |
| 6,391,816 | B1 | 5/2002 | McDaniel |
| 6,395,666 | B1 | 5/2002 | McDaniel |
| 6,403,732 | B2 | 6/2002 | Marks et al. |
| 6,403,733 | B2 | 6/2002 | Marks et al. |
| 6,524,987 | B1 | 2/2003 | Collins |
| 6,544,922 | B1 | 4/2003 | Marks et al. |
| 6,548,441 | B1 | 4/2003 | McDaniel |
| 6,548,442 | B1 | 4/2003 | McDaniel |
| 6,576,583 | B1 | 6/2003 | McDaniel |
| 6,613,712 | B1 | 9/2003 | McDaniel |
| 6,632,894 | B1 | 10/2003 | McDaniel |
| 6,667,274 | B1 | 12/2003 | Hawley |
| 6,670,299 | B1 | 12/2003 | Marks et al. |
| 6,747,112 | B2 | 6/2004 | Marks et al. |
| 6,750,302 | B1 | 6/2004 | McDaniel |
| 6,833,415 | B2 | 12/2004 | Kendrick |
| 7,064,225 | B2 | 6/2006 | Thorn |
| 7,119,153 | B2 | 10/2006 | Jensen et al. |
| 7,119,158 | B2 | 10/2006 | Marks et al. |
| 7,160,965 | B2 | 1/2007 | Marks et al. |
| 7,226,886 | B2 | 6/2007 | Jayaratne |
| 7,312,283 | B2 | 12/2007 | Martin et al. |
| 7,435,701 | B2 | 10/2008 | Shen |
| 7,495,036 | B2 | 2/2009 | Farrar |
| 7,517,939 | B2 | 4/2009 | Yang |
| 7,619,047 | B2 | 11/2009 | Yang et al. |
| 7,863,210 | B2 | 1/2011 | Murray et al. |
| 2002/0107345 | A1 * | 8/2002 | Ittel et al. ............ 526/161 |
| 2003/0069373 | A1 * | 4/2003 | Holtcamp et al. ............ 526/170 |
| 2003/0134995 | A1 | 7/2003 | Marks et al. |
| 2004/0072677 | A1 * | 4/2004 | Lee et al. ............ 502/103 |
| 2004/0106514 | A1 | 6/2004 | Nagy |
| 2005/0043541 | A1 | 2/2005 | Walter et al. |
| 2005/0285284 | A1 * | 12/2005 | Thorn et al. ............ 260/665 R |
| 2005/0288461 | A1 | 12/2005 | Jensen |
| 2006/0183631 | A1 | 8/2006 | Lee |
| 2007/0179044 | A1 | 8/2007 | Yang |
| 2007/0203018 | A1 | 8/2007 | Kwon |
| 2009/0170690 | A1 | 7/2009 | Murray |
| 2009/0171041 | A1 | 7/2009 | Murray |
| 2009/0240010 | A1 | 9/2009 | McDaniel et al. |
| 2010/0317904 | A1 | 12/2010 | Small |
| 2010/0324236 | A1 | 12/2010 | Murray et al. |

FOREIGN PATENT DOCUMENTS

| | | | |
|---|---|---|---|
| EP | 01743899 | A1 | 1/2007 |
| WO | WO 03/027131 | | 4/2003 |
| WO | WO 2009/085124 | A1 | 7/2009 |
| WO | WO 2009/085126 | A1 | 7/2009 |
| WO | WO 2009/085129 | A1 | 7/2009 |

OTHER PUBLICATIONS

Junpei Kuwabara et al. "Zr/Zr and Zr/Fe Dinuclear Complexes with Flexible Bridging Ligands.Preparatopm by Olefin metathesis Reaction of the mononuclear Precursors and Properties as Polymerization Catalysts". Apr. 26, 2005.*

Sierra et al. (CHem, Eur.J. 2003, 3628-3622).*

Kuwabara et al. (Organometallics, 2005, 24, 2706-2712).*

Kuwabara, Junpei, et al., Zr/Zr and Zr/Fe Dinuclear Complexes with Flexible Bridging Ligands, Preparation by Olefin Metathesis Reaction of the Mononuclear Precursors and Properties as Polymerization Catalysts, *Organometallics*, v. 25 (2005) pp. 2705-2712.

International Patent Application No. PCT/US2008/013705 Search Report.

Sierra, Jesus C., et al., "Formation of Dinuclear Titanium and Zirconium Complexes by Olefin Metathesis-Catalytic Preparation of Organometallic Catalyst Systems," Chem. Eur. J. 2003, 9, 3618-3622.

Ogasawara, Masamichi, et al., "Metathesis Route to Bridged Metallocenes," J. Am. Chem. Soc. 2002, 124, 9068-9069.

Hüerländer, Doris, et al., "Synthesis, Structural and Chemical Characterization of Unsaturated $C_4$- and $C_{10}$- Bridged Group-4 *ansa*-Metallocenes Obtained Through a Ring-Closing Olefin Metathesis Reaction," Eur. J. Inorg. Chem. 2002, 2633-2642.

Hongbo, Li, et al., "Coordination Copolymerization of Severly Encumbered Isoalkenes with Ethylene: Enhanced Enchainment Mediated by Binuclear Catalysts and Cocatalysts," J. Am. Chem. Soc. 2005, 127, 14756-14768.

Murray et al., pending U.S. Appl. No. 11/965,848, filed Dec. 28, 2007 (IFW accessible).

Murray et al., pending U.S. Appl. No. 11/966,081, filed Dec. 28, 2007 (IFW accessible).

Guo, et al., Bimetallic Catalysis for Styrene Homopolymerization and Ethylene—Styrene Copolymerization. Exceptional Comonomer Selectivity and Insertion Regiochemistry. J. Am. Chem. Soc., 2004, 126(21), 6542-6543.

Hüerländer, Doris, et al., "Synthesis, Structural and Chemical Characterization of Unsaturated C4• and C10•Bridged Group-4 *ansa*-Metallocenes Obtained Through a Ring-Closing Olefin Metathesis Reaction," Eur..J. Inorg. Chem., 2002, 2633-2642.

Li, et al., Catalyst/Cocatalyst Nuclearity Effects in Single-Site Polymerization Enhanced Polyethylene Branching and □-Olefin Comonomer Enchainment in Polymerizations Mediated by Binuclear Catalysts and Cocatalysts via a New Enchainment Pathway, J.Am. Chem. Soc., 2002, 124(43), 12725-12741.

Wang, et al., Covalently Linked Heterobimetallic Catalysts for Olefin Polymerization, Organometallics, 2004, 23(22), 5112-5114.

Murray et al., pending U.S. Appl. No. 12/489,630, filed Jun. 23, 2009.

International Search Report in PCT Application No. PCT/US2010/001795, mailed Aug. 9, 2010, 7 pages.

U.S. Appl. No. 12/898,465 filed Oct. 5, 2010 entitled "Oligomerization of Olefin Waxes Using Metallocene-Based Catalyst Systems".

Hawley's Condensed Chemical Dictionary, 11th Ed., John Wiley & Sons, 1995, 3 pages.

Cotton et al., Advanced Inorganic Chemistry, 6th Ed., Wiley-Interscience, 1999, 4 pages.

Pinnavaia, "Intercalated Clay Catalysts," Science, 1983, 220(4595), pp. 365-371.

Thomas, "Sheet Silicate Intercalates: New Agents for Unusual Chemical Conversions*," Intercalation Chemistry (S. Whittington and A. Jacobson, eds.), Academic Press, Inc. Ch. 3, 1972, pp. 55-99.

* cited by examiner

NANO-LINKED METALLOCENE CATALYST COMPOSITIONS AND THEIR POLYMER PRODUCTS

BACKGROUND OF THE INVENTION

The present invention relates generally to the field of olefin polymerization catalysis, catalyst compositions, methods for the polymerization and copolymerization of olefins, and polyolefins. More specifically, this invention relates to nano-linked dinuclear metallocene compounds and catalyst compositions employing such compounds.

A dinuclear metallocene compound can be produced via an olefin metathesis reaction, for example, as shown in Chem. Eur. J., 2003, 9, pp. 3618-3622. Olefin metathesis is a catalytic reaction between compounds that contain olefinic (e.g., alkene) moieties. Catalysts that are often employed in an olefin metathesis reaction include metals such as ruthenium, tungsten, molybdenum, or nickel.

SUMMARY OF THE INVENTION

The present invention generally relates to new catalyst compositions, methods for preparing catalyst compositions, methods for using the catalyst compositions to polymerize olefins, the polymer resins produced using such catalyst compositions, and articles produced using these polymer resins. In particular, the present invention relates to nano-linked dinuclear metallocene compounds and catalyst compositions employing such compounds. Catalyst compositions containing nano-linked dinuclear metallocene compounds of the present invention can be used to produce, for example, ethylene-based homopolymers and copolymers.

The present invention discloses novel dinuclear metallocene compounds having two metallocene moieties linked by an alkenyl group. According to one aspect of the present invention, these dinuclear compounds have the formula:

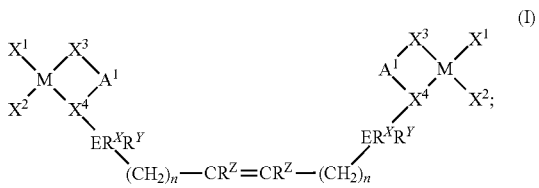
(I)

wherein:

$X^1$ and $X^2$ independently are a halide or a substituted or unsubstituted aliphatic, aromatic, or cyclic group, or a combination thereof;

$X^3$ is a substituted cyclopentadienyl, indenyl, or fluorenyl group, any substituents on $X^3$ other than a bridging group independently are a hydrogen atom or a substituted or unsubstituted alkyl or alkenyl group;

$X^4$ is a substituted cyclopentadienyl, indenyl, or fluorenyl group, any substituents on $X^4$ other than the bridging group and an alkenyl linking group independently are a hydrogen atom or a substituted or unsubstituted alkyl or alkenyl group;

$A^1$ is a substituted or unsubstituted bridging group comprising either a cyclic group of 5 to 8 carbon atoms, a bridging chain of 2 to 5 carbon atoms, or a carbon, silicon, germanium, tin, boron, nitrogen, or phosphorus bridging atom, any substituents on $A^1$ independently are a hydrogen atom, or a substituted or unsubstituted aliphatic, aromatic, or cyclic group, or a combination thereof;

M is Zr, Hf, or Ti;

E is carbon or silicon;

$R^X$, $R^Y$, and $R^Z$ independently are a hydrogen atom, or a substituted or unsubstituted aliphatic, aromatic, or cyclic group, or a combination thereof, and n is an integer in a range from 0 to 12, inclusive.

with the proviso that $A^1$ is not a silicon bridging atom when both $X^1$ and $X^2$ are chlorine atoms, both $X^3$ and $X^4$ are cyclopentadienyl groups, E is carbon, $R^X$, $R^Y$, and $R^Z$ are each hydrogen atoms, and n is equal to 0.

Catalyst compositions containing these nano-linked dinuclear metallocene compounds are also provided by the present invention. In one aspect, a catalyst composition is disclosed which comprises a contact product of at least one dinuclear metallocene compound and at least one compound selected from at least one aluminoxane compound, at least one organozinc compound, at least one organoboron or organoborate compound, at least one ionizing ionic compound, or any combination thereof. In this aspect, the dinuclear compound is as defined above in formula (I).

In another aspect, a catalyst composition comprising a contact product of at least one dinuclear metallocene compound and at least one activator-support is provided. This catalyst composition can further comprise at least one organoaluminum compound, as well as other co-catalysts. In these and other aspects, the at least one dinuclear metallocene compound is selected from:

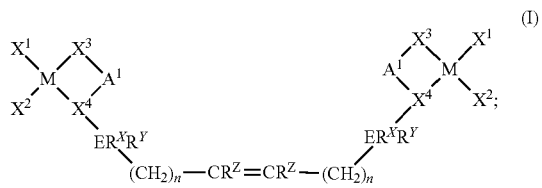
(I)

wherein:

$X^1$ and $X^2$ independently are a halide or a substituted or unsubstituted aliphatic, aromatic, or cyclic group, or a combination thereof;

$X^3$ is a substituted cyclopentadienyl, indenyl, or fluorenyl group, any substituents on $X^3$ other than a bridging group independently are a hydrogen atom or a substituted or unsubstituted alkyl or alkenyl group;

$X^4$ is a substituted cyclopentadienyl, indenyl, or fluorenyl group, any substituents on $X^4$ other than the bridging group and an alkenyl linking group independently are a hydrogen atom or a substituted or unsubstituted alkyl or alkenyl group;

$A^1$ is a substituted or unsubstituted bridging group comprising either a cyclic group of 5 to 8 carbon atoms, a bridging chain of 2 to 5 carbon atoms, or a carbon, silicon, germanium, tin, boron, nitrogen, or phosphorus bridging atom, any substituents on $A^1$ independently are a hydrogen atom, or a substituted or unsubstituted aliphatic, aromatic, or cyclic group, or a combination thereof, M is Zr, Hf, or Ti;

E is carbon or silicon;

$R^X$, $R^Y$, and $R^Z$ independently are a hydrogen atom, or a substituted or unsubstituted aliphatic, aromatic, or cyclic group, or a combination thereof; and n is an integer in a range from 0 to 12, inclusive.

with the proviso that $A^1$ is not a silicon bridging atom when both $X^1$ and $X^2$ are chlorine atoms, both $X^3$ and $X^4$ are cyclopentadienyl groups, E is carbon, $R^X$, $R^Y$, and $R^Z$ are each hydrogen atoms, and n is equal to 0.

The present invention also contemplates a process for polymerizing olefins in the presence of a catalyst composition, the process comprising contacting the catalyst composition with at least one olefin monomer and optionally at least one olefin comonomer under polymerization conditions to produce a polymer or copolymer. The catalyst composition can comprise a contact product of at least one dinuclear metallocene compound and at least one activator-support. Other co-catalysts, including organoaluminum compounds, can be employed in this process.

Polymers produced from the polymerization of olefins, resulting in either homopolymers or copolymers, can be used to produce various articles of manufacture.

DEFINITIONS

Figure 1:
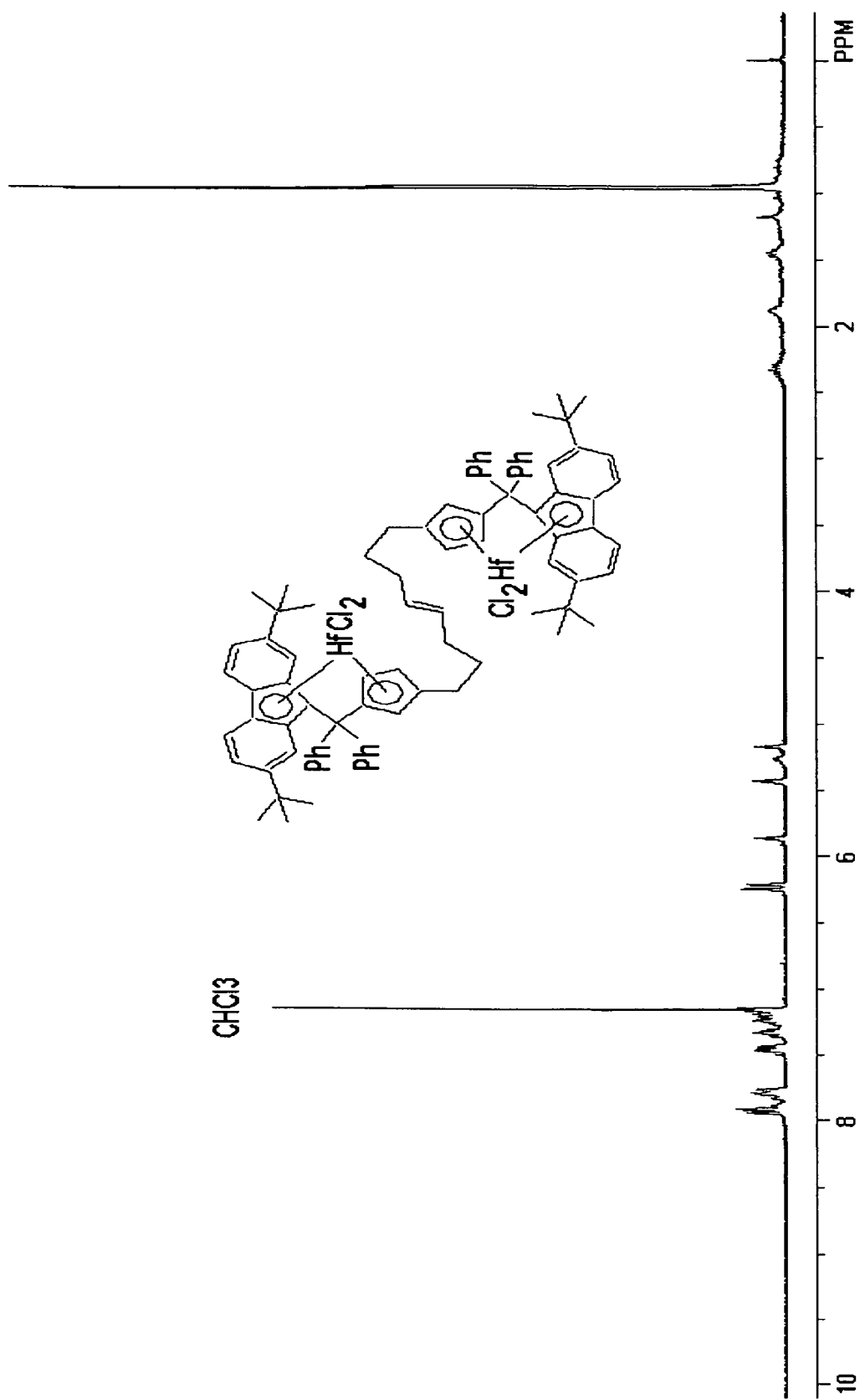
FIG. 1 presents an NMR plot of Example 1.

To define more clearly the terms used herein, the following definitions are provided. To the extent that any definition or usage provided by any document incorporated herein by reference conflicts with the definition or usage provided herein, the definition or usage provided herein controls.

The term "polymer" is used herein to mean homopolymers comprising ethylene and copolymers of ethylene and a comonomer. "Polymer" is also used herein to mean homopolymers and copolymers of any olefin monomer disclosed herein (e.g., propylene).

The term "co-catalyst" is used generally herein to refer to organoaluminum compounds that can constitute one component of a catalyst composition. Additionally, "co-catalyst" refers to other components of a catalyst composition including, but not limited to, aluminoxanes, organozinc compounds, organoboron or organoborate compounds, ionizing ionic compounds, as disclosed herein. The term "co-catalyst" is used regardless of the actual function of the compound or any chemical mechanism by which the compound may operate. In one aspect of this invention, the term "co-catalyst" is used to distinguish that component of the catalyst composition from the dinuclear metallocene compound.

The term "fluoroorgano boron compound" is used herein with its ordinary meaning to refer to neutral compounds of the form $BY_3$. The term "fluoroorgano borate compound" also has its usual meaning to refer to the monoanionic salts of a fluoroorgano boron compound of the form $[cation]^+[BY_4]^-$, where Y represents a fluorinated organic group. Materials of these types are generally and collectively referred to as "organoboron or organoborate compounds."

The term "contact product" is used herein to describe compositions wherein the components are contacted together in any order, in any manner, and for any length of time. For example, the components can be contacted by blending or mixing. Further, contacting of any component can occur in the presence or absence of any other component of the compositions described herein. Combining additional materials or components can be done by any suitable method. Further, the term "contact product" includes mixtures, blends, solutions, slurries, reaction products, and the like, or combinations thereof. Although "contact product" can include reaction products, it is not required for the respective components to react with one another.

The term "precontacted" mixture is used herein to describe a first mixture of catalyst components that are contacted for a first period of time prior to the first mixture being used to form a "postcontacted" or second mixture of catalyst components that are contacted for a second period of time. Typically, the precontacted mixture describes a mixture of metallocene compound (or compounds), olefin monomer, and organoaluminum compound (or compounds), before this mixture is contacted with an activator-support and optional additional organoaluminum compound. Thus, precontacted describes components that are used to contact each other, but prior to contacting the components in the second, postcontacted mixture. Accordingly, this invention may occasionally distinguish between a component used to prepare the precontacted mixture and that component after the mixture has been prepared. For example, according to this description, it is possible for the precontacted organoaluminum compound, once it is contacted with the metallocene and the olefin monomer, to have reacted to form at least one different chemical compound, formulation, or structure from the distinct organoaluminum compound used to prepare the precontacted mixture. In this case, the precontacted organoaluminum compound or component is described as comprising an organoaluminum compound that was used to prepare the precontacted mixture.

Similarly, the term "postcontacted" mixture is used herein to describe a second mixture of catalyst components that are contacted for a second period of time, and one constituent of which is the "precontacted" or first mixture of catalyst components that were contacted for a first period of time. Typically, the term "postcontacted" mixture is used herein to describe the mixture of metallocene compound, olefin monomer, organoaluminum compound, and activator-support (e.g., chemically-treated solid oxide), formed from contacting the precontacted mixture of a portion of these components with any additional components added to make up the postcontacted mixture. Generally, the additional component added to make up the postcontacted mixture is a chemically-treated solid oxide, and, optionally, can include an organoaluminum compound which is the same as or different from the organoaluminum compound used to prepare the precontacted mixture, as described herein. Accordingly, this invention may also occasionally distinguish between a component used to prepare the postcontacted mixture and that component after the mixture has been prepared.

The term "dinuclear metallocene," as used herein, describes a compound comprising two metallocene moieties linked by a connecting group. The connecting group can be an alkenyl group resulting from the metathesis reaction or the saturated version resulting from hydrogenation or derivatization. Thus, the dinuclear metallocenes of this invention contain four $\eta^3$ to $\eta^5$-cyclopentadienyl-type moieties, wherein the $\eta^3$ to $\eta^5$-cycloalkadienyl moieties include cyclopentadienyl ligands, indenyl ligands, fluorenyl ligands, and the like, including partially saturated or substituted derivatives or analogs of any of these. Possible substituents on these ligands include hydrogen, therefore the description "substituted derivatives thereof" in this invention comprises partially saturated ligands such as tetrahydroindenyl, tetrahydrofluorenyl, octahydrofluorenyl, partially saturated indenyl, partially saturated fluorenyl, substituted partially saturated indenyl, substituted partially saturated fluorenyl, and the like. In some contexts, the dinuclear metallocene is referred to simply as the "catalyst," in much the same way the term "co-catalyst" is used herein to refer to, for example, an organoaluminum compound. Unless otherwise specified, the following abbreviations are used: Cp for cyclopentadienyl; Ind for indenyl; and Flu for fluorenyl.

The terms "catalyst composition," "catalyst mixture," "catalyst system," and the like, do not depend upon the actual product resulting from the contact or reaction of the components of the mixtures, the nature of the active catalytic site, or the fate of the co-catalyst, the dinuclear metallocene compound, any olefin monomer used to prepare a precontacted mixture, or the activator-support, after combining these components. Therefore, the terms "catalyst composition," "catalyst mixture," "catalyst system," and the like, can include both heterogeneous compositions and homogenous compositions.

The term "hydrocarbyl" is used herein to specify a hydrocarbon radical group that includes, but is not limited to, aryl, alkyl, cycloalkyl, alkenyl, cycloalkenyl, cycloalkadienyl, alkynyl, aralkyl, aralkenyl, aralkynyl, and the like, and includes all substituted, unsubstituted, branched, linear, heteroatom substituted derivatives thereof.

The terms "chemically-treated solid oxide," "solid oxide activator-support," "treated solid oxide compound," and the like, are used herein to indicate a solid, inorganic oxide of relatively high porosity, which exhibits Lewis acidic or Brønsted acidic behavior, and which has been treated with an electron-withdrawing component, typically an anion, and which is calcined. The electron-withdrawing component is typically an electron-withdrawing anion source compound. Thus, the chemically-treated solid oxide compound comprises a calcined contact product of at least one solid oxide compound with at least one electron-withdrawing anion source compound. Typically, the chemically-treated solid oxide comprises at least one ionizing, acidic solid oxide compound. The terms "support" and "activator-support" are not used to imply these components are inert, and such components should not be construed as an inert component of the catalyst composition. The activator-support of the present invention can be a chemically-treated solid oxide.

Although any methods, devices, and materials similar or equivalent to those described herein can be used in the practice or testing of the invention, the typical methods, devices and materials are herein described.

All publications and patents mentioned herein are incorporated herein by reference for the purpose of describing and disclosing, for example, the constructs and methodologies that are described in the publications, which might be used in connection with the presently described invention. The publications discussed throughout the text are provided solely for their disclosure prior to the filing date of the present application. Nothing herein is to be construed as an admission that the inventors are not entitled to antedate such disclosure by virtue of prior invention.

For any particular compound disclosed herein, any general structure presented also encompasses all conformational isomers, regioisomers, and stereoisomers that may arise from a particular set of substituents. The general structure also encompasses all enantiomers, diastereomers, and other optical isomers whether in enantiomeric or racemic forms, as well as mixtures of stereoisomers, as the context requires. For example, isomerized and hydrogenated forms of the general structure illustrated in formula (I) are also contemplated.

Applicants disclose several types of ranges in the present invention. These include, but are not limited to, a range of number of atoms, a range of integers, a range of weight ratios, a range of molar ratios, and so forth. When Applicants disclose or claim a range of any type, Applicants' intent is to disclose or claim individually each possible number that such a range could reasonably encompass, including end points of the range as well as any sub-ranges and combinations of sub-ranges encompassed therein. For example, when the Applicants disclose or claim a chemical moiety having a certain number of carbon atoms, Applicants' intent is to disclose or claim individually every possible number that such a range could encompass, consistent with the disclosure herein. For example, the disclosure that a moiety is a $C_1$ to $C_{10}$ linear or branched alkyl group, or in alternative language having from 1 to 10 carbon atoms, as used herein, refers to a moeity that can be selected independently from an alkyl group having 1, 2, 3, 4, 5, 6, 7, 8, 9, or 10 carbon atoms, as well as any range between these two numbers (for example, a $C_1$ to $C_6$ alkyl group), and also including any combination of ranges between these two numbers (for example, a $C_2$ to $C_4$ and $C_6$ to $C_8$ alkyl group).

Similarly, another representative example follows for the weight ratio of organoaluminum to activator-support in a catalyst composition provided in one aspect of this invention. By a disclosure that the weight ratio of organoaluminum compound to activator-support is in a range from about 10:1 to about 1:1000, applicants intend to recite that the weight ratio can be selected from about 10:1, about 9:1, about 8:1, about 7:1, about 6:1, about 5:1, about 4:1, about 3:1, about 2:1, about 1:1, about 1:5, about 1:10, about 1:25, about 1:50, about 1:75, about 1:100, about 1:150, about 1:200, about 1:250, about 1:300, about 1:350, about 1:400, about 1:450, about 1:500, about 1:550, about 1:600, about 1:650, about 1:700, about 1:750, about 1:800, about 1:850, about 1:900, about 1:950, or about 1:1000. Additionally, the weight ratio can be within any range from about 10:1 to about 1:1000 (for example, the weight ratio is in a range from about 3:1 to about 1:100), and this also includes any combination of ranges between about 10:1 to about 1:1000. Likewise, all other ranges disclosed herein should be interpreted in a manner similar to these two examples.

Applicants reserve the right to proviso out or exclude any individual members of any such group, including any sub-ranges or combinations of sub-ranges within the group, that can be claimed according to a range or in any similar manner, if for any reason Applicants choose to claim less than the full measure of the disclosure, for example, to account for a reference that Applicants may be unaware of at the time of the filing of the application. Further, Applicants reserve the right to proviso out or exclude any individual substituents, analogs, compounds, ligands, structures, or groups thereof, or any members of a claimed group, if for any reason Applicants choose to claim less than the full measure of the disclosure, for example, to account for a reference that Applicants may be unaware of at the time of the filing of the application.

While compositions and methods are described in terms of "comprising" various components or steps, the compositions and methods can also "consist essentially of" or "consist of" the various components or steps.

DETAILED DESCRIPTION OF THE INVENTION

The present invention is directed generally to new catalyst compositions, methods for preparing catalyst compositions, methods for using the catalyst compositions to polymerize olefins, the polymer resins produced using such catalyst compositions, and articles produced using these polymer resins. In particular, the present invention relates to nano-linked dinuclear metallocene compounds and catalyst compositions employing such compounds.

Nano-linked metallocenes of the present invention are dinuclear molecules in which metallocene moieties are connected by an alkenyl linking group, or nano-link. Nano-linked metallocenes can be designed with specific angstrom distances between the two metal centers, where the distance is determined principally by the connecting linkage or linking group. The length, stereochemistry, and flexibility or rigidity of the linking group can be used to design catalysts which are either capable of, or incapable of, intra-molecular metal-to-metal interactions. For instance, under the restraint of the nano-link (e.g., an alkenyl linking group), nano-linked dinuclear metallocenes can offer unique co-catalyst interactions.

Dinuclear Metallocene Compouds

The present invention discloses novel compounds having two metallocene moieties linked by an alkenyl group, and methods of making these new compounds. These compounds are commonly referred to as dinuclear compounds, or binuclear compounds, because they contain two metal centers. Accordingly, in one aspect of this invention, the dinuclear compounds have the formula:

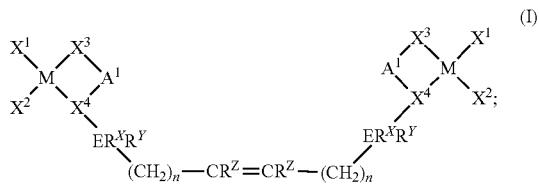

wherein:

$X^1$ and $X^2$ independently are a halide or a substituted or unsubstituted aliphatic, aromatic, or cyclic group, or a combination thereof;

$X^3$ is a substituted cyclopentadienyl, indenyl, or fluorenyl group, any substituents on $X^3$ other than a bridging group independently are a hydrogen atom or a substituted or unsubstituted alkyl or alkenyl group;

$X^4$ is a substituted cyclopentadienyl, indenyl, or fluorenyl group, any substituents on $X^4$ other than the bridging group and an alkenyl linking group independently are a hydrogen atom or a substituted or unsubstituted alkyl or alkenyl group;

$A^1$ is a substituted or unsubstituted bridging group comprising either a cyclic group of 5 to 8 carbon atoms, a bridging chain of 2 to 5 carbon atoms, or a carbon, silicon, germanium, tin, boron, nitrogen, or phosphorus bridging atom, any substituents on $A^1$ independently are a hydrogen atom, or a substituted or unsubstituted aliphatic, aromatic, or cyclic group, or a combination thereof;

M is Zr, Hf, or Ti;

E is carbon or silicon;

$R^X$, $R^Y$, and $R^Z$ independently are a hydrogen atom, or a substituted or unsubstituted aliphatic, aromatic, or cyclic group, or a combination thereof, and n is an integer in a range from 0 to 12, inclusive.

with the proviso that $A^1$ is not a silicon bridging atom when both $X^1$ and $X^2$ are chlorine atoms, both $X^3$ and $X^4$ are cyclopentadienyl groups, E is carbon, $R^X$, $R^Y$, and $R^Z$ are each hydrogen atoms, and n is equal to 0.

Formula (I) above is not designed to show stereochemistry or isomeric positioning of the different moieties (e.g., this formula is not intended to display cis or trans isomers, or R or S diastereoisomers), although such compounds are contemplated and encompassed by this formula.

In formula (I), halides include fluorine, chlorine, bromine, and iodine atoms. As used herein, an aliphatic group includes linear or branched alkyl and alkenyl groups. Generally, the aliphatic group contains from 1 to 20 carbon atoms. Unless otherwise specified, alkyl and alkenyl groups described herein are intended to include all structural isomers, linear or branched, of a given moiety; for example, all enantiomers and all diastereomers are included within this definition. As an example, unless otherwise specified, the term propyl is meant to include n-propyl and iso-propyl, while the term butyl is meant to include n-butyl, iso-butyl, t-butyl, sec-butyl, and so forth. For instance, non-limiting examples of octyl isomers include 2-ethyl hexyl and neooctyl. Suitable examples of alkyl groups which can be employed in the present invention include, but are not limited to, methyl, ethyl, propyl, butyl, pentyl, hexyl, heptyl, octyl, nonyl, or decyl, and the like. Examples of alkenyl groups within the scope of the present invention include, but are not limited to, ethenyl, propenyl, butenyl, pentenyl, hexenyl, heptenyl, octenyl, nonenyl, decenyl, and the like.

Aromatic groups and combinations with aliphatic groups include aryl and arylalkyl groups, and these include, but are not limited to, phenyl, alkyl-substituted phenyl, naphthyl, alkyl-substituted naphthyl, phenyl-substituted alkyl, naphthyl-substituted alkyl, and the like. Generally, such groups and combinations of groups contain less than 20 carbon atoms. Hence, non-limiting examples of such moieties that can be used in the present invention include phenyl, tolyl, benzyl, dimethylphenyl, trimethylphenyl, phenylethyl, phenylpropyl, phenylbutyl, propyl-2-phenylethyl, and the like. Cyclic groups include cycloalkyl and cycloalkenyl moieties and such moieties can include, but are not limited to, cyclopentyl, cyclopentenyl, cyclohexyl, cyclohexenyl, cyclooctyl, cyclooctenyl, and the like. One example of a combination including a cyclic group is a cyclohexylphenyl group. Unless otherwise specified, any substituted aromatic or cyclic moiety used herein is meant to include all regioisomers; for example, the term tolyl is meant to include any possible substituent position, that is, ortho, meta, or para.

In formula (I), an alkenyl linking group is an alkenyl group that links or connects the two metallocene moieties. As illustrated in the above formula, the alkenyl linking group is attached to the metallocene moieties at a cyclopentadienyl, indenyl, or fluorenyl group. $X^4$ can have one or more substituents in addition to the alkenyl linking group and the bridging group.

In one aspect of the present invention, $X^1$ and $X^2$ independently are a substituted or unsubstituted aliphatic group having from 1 to 20 carbon atoms. In another aspect, $X^1$ and $X^2$ independently are methyl, ethyl, propyl, butyl, pentyl, hexyl, heptyl, octyl, nonyl, decyl, or trimethylsilylmethyl. In yet another aspect, $X^1$ and $X^2$ independently are ethenyl, propenyl, butenyl, pentenyl, hexenyl, heptenyl, octenyl, nonenyl, or decenyl. $X^1$ and $X^2$ independently are a substituted or unsubstituted aromatic group, for example, having up to 20 carbon atoms, in another aspect of the present invention.

In a different aspect, $X^1$ and $X^2$ are both chlorine atoms. $X^1$ and $X^2$ independently can be selected from phenyl, naphthyl, tolyl, benzyl, dimethylphenyl, trimethylphenyl, phenylethyl, phenylpropyl, phenylbutyl, propyl-2-phenylethyl, cyclopentyl, cyclopentenyl, cyclohexyl, cyclohexenyl, or cyclohexylphenyl in other aspects of this invention. Yet, in another aspect, $X^1$ and $X^2$ independently are methyl, phenyl, benzyl, or a halide. Further, $X^1$ and $X^2$ independently can be methyl, phenyl, benzyl, or a chlorine atom in another aspect of the present invention.

In formula (I), $X^3$ and $X^4$ independently are a substituted cyclopentadienyl, indenyl, or fluorenyl group, and are necessarily substituted with a bridging group, $A^1$, as indicated in the formula above. $X^4$ is further substituted with an alkenyl linking group. In one aspect of the present invention, $X^3$ and $X^4$ independently are either a substituted cyclopentadienyl group or a substituted fluorenyl group. In another aspect, $X^4$ is a substituted cyclopentadienyl group, while $X^3$ is a substituted fluorenyl group. Yet, in another aspect, $X^3$ is a substituted indenyl group.

Any substituents on $X^3$ other than the bridging group independently are a hydrogen atom or a substituted or unsubstituted alkyl or alkenyl group. Hydrogen is included, therefore the notion of a substituted indenyl and substituted fluorenyl includes partially saturated indenyls and fluorenyls including, but not limited to, tetrahydroindenyls, tetrahydrofluorenyls, and octahydrofluorenyls. Exemplary alkyls that can be substituents on $X^3$ include methyl, ethyl, propyl, butyl, pentyl, hexyl, heptyl, octyl, nonyl, or decyl, and the like. In one aspect, excluding the bridging group, each substituent on $X^3$ independently is a hydrogen atom, or an ethyl, propyl, n-butyl, t-butyl, or hexyl group. In another aspect, substituents on $X^3$ are selected independently from a hydrogen atom, ethenyl, propenyl, butenyl, pentenyl, hexenyl, heptenyl, octenyl, nonenyl, or decenyl, exclusive of the bridging group.

$X^4$ in formula (I) is a substituted cyclopentadienyl, indenyl, or fluorenyl group, and is substituted with the bridging group $A^1$ and an alkenyl linking group. In one aspect of this invention, $X^4$ contains no further substitutions. $X^4$ can be further substituted with a hydrogen atom or a substituted or unsubstituted alkyl or alkenyl group in a different aspect of this invention. For example, suitable alkyls that can be substituents on $X^4$ include methyl, ethyl, propyl, butyl, pentyl, hexyl, heptyl, octyl, nonyl, or decyl, and the like. In another aspect, excluding the bridging group and the alkenyl linking group, any substituent on $X^4$ independently is selected from a hydrogen atom, or an ethyl, propyl, n-butyl, t-butyl or hexyl group. In yet another aspect, substituents on $X^4$ are selected independently from a hydrogen atom, ethenyl, propenyl, butenyl, pentenyl, hexenyl, heptenyl, octenyl, nonenyl, or decenyl, exclusive of the aforementioned bridging group and alkenyl linking group.

In formula (I), $A^1$ is a substituted or unsubstituted bridging group comprising either a cyclic group of 5 to 8 carbon atoms, a bridging chain of 2 to 5 carbon atoms, or a carbon, silicon, germanium, tin, boron, nitrogen, or phosphorus bridging atom, which connects $X^3$ and $X^4$. In one aspect of this invention, $A^1$ is a silicon bridging atom. In a different aspect, $A^1$ is a carbon bridging atom. Yet, in another aspect, $A^1$ is a bridging chain of 2 to 5 carbon atoms, such as, for example, a two-carbon bridging chain that connects $X^3$ and $X^4$. $A^1$ can be a germanium, tin, boron, nitrogen, or phosphorus bridging atom in other aspects of the present invention. In accordance with yet another aspect of this invention, $A^1$ can be a cyclic group of 5 to 8 carbon atoms such as, for example, a cyclopentyl or cyclohexyl group.

Any substituents on $A^1$ are selected independently from a hydrogen atom, or a substituted or unsubstituted aliphatic, aromatic, or cyclic group, or a combination thereof. $A^1$ can have one or more substituents. In one aspect, for example, a substituent on $A^1$ can be a methyl, ethyl, propyl, butyl, pentyl, hexyl, ethenyl, propenyl, butenyl, pentenyl, hexenyl, phenyl, naphthyl, tolyl, benzyl, cyclopentyl, cyclohexyl, or cyclohexylphenyl group, or a hydrogen atom. Yet, in another aspect, each substituent on the bridging group is selected independently from a hydrogen atom, methyl group, phenyl group, naphthyl group, or cyclohexylphenyl group. In a further aspect, $A^1$ has two phenyl substituents, or alternatively, $A^1$ has two methyl substituents.

In formula (I), substituted aliphatic, aromatic, or cyclic groups, and combinations thereof, are disclosed, as well as substituted alkyl or alkenyl groups. Such groups described herein are intended to include substituted analogs with substitutions at any position on these groups that conform to the normal rules of chemical valence. Thus, groups substituted with one or more than one substituent are contemplated.

Such substituents, when present, are independently selected from an oxygen group, a sulfur group, a nitrogen group, a phosphorus group, an arsenic group, a carbon group, a silicon group, a germanium group, a tin group, a lead group, a boron group, an aluminum group, an inorganic group, an organometallic group, or a substituted derivative thereof, any of which having from 1 to about 20 carbon atoms; a halide; or hydrogen; as long as these groups do not terminate the activity of the catalyst composition. Examples of each of these substituent groups include, but are not limited to, the following groups.

Examples of halide substituents, in each occurrence, include fluoride, chloride, bromide, and iodide.

In each occurrence, oxygen groups are oxygen-containing groups, examples of which include, but are not limited to, alkoxy or aryloxy groups ($-OR^A$), $-OSiR^A_3$, $-OPR^A_2$, $-OAlR^A_2$, and the like, including substituted derivatives thereof, wherein $R^A$ in each occurrence can be alkyl, cycloalkyl, aryl, aralkyl, substituted alkyl, substituted aryl, or substituted aralkyl having from 1 to 20 carbon atoms. Examples of alkoxy or aryloxy groups ($-OR^A$) groups include, but are not limited to, methoxy, ethoxy, propoxy, butoxy, phenoxy, substituted phenoxy, and the like.

In each occurrence, sulfur groups are sulfur-containing groups, examples of which include, but are not limited to, $-SR^A$ and the like, including substituted derivatives thereof, wherein $R^A$ in each occurrence can be alkyl, cycloalkyl, aryl, aralkyl, substituted alkyl, substituted aryl, or substituted aralkyl having from 1 to 20 carbon atoms.

In each occurrence, nitrogen groups are nitrogen-containing groups, which include, but are not limited to, $-NR^A_2$ and the like, including substituted derivatives thereof, wherein $R^A$ in each occurrence can be alkyl, cycloalkyl, aryl, aralkyl, substituted alkyl, substituted aryl, or substituted aralkyl having from 1 to 20 carbon atoms.

In each occurrence, phosphorus groups are phosphorus-containing groups, which include, but are not limited to, $-PR^A_2$, $-P(OR^A)_2$, and the like, including substituted derivatives thereof, wherein $R^A$ in each occurrence can be alkyl, cycloalkyl, aryl, aralkyl, substituted alkyl, substituted aryl, or substituted aralkyl having from 1 to 20 carbon atoms.

In each occurrence, arsenic groups are arsenic-containing groups, which include, but are not limited to, $-AsR^A_2$, $-As(OR^A)_2$, and the like, including substituted derivatives thereof, wherein $R^A$ in each occurrence can be alkyl, cycloalkyl, aryl, aralkyl, substituted alkyl, substituted aryl, or substituted aralkyl having from 1 to 20 carbon atoms.

In each occurrence, carbon groups are carbon-containing groups, which include, but are not limited to, alkyl halide groups that comprise halide-substituted alkyl groups with 1 to 20 carbon atoms, aralkyl groups with 1 to 20 carbon atoms, $-C(NR^A)H$, $-C(NR^A)R^A$, $-C(NR^A)OR^A$, and the like, including substituted derivatives thereof, wherein $R^A$ in each occurrence can be alkyl, cycloalkyl, aryl, aralkyl, substituted alkyl, substituted aryl, or substituted aralkyl having from 1 to 20 carbon atoms.

In each occurrence, silicon groups are silicon-containing groups, which include, but are not limited to, silyl groups such as alkylsilyl groups, arylsilyl groups, arylalkylsilyl groups, siloxy groups, and the like, which in each occurrence have from 1 to 20 carbon atoms. For example, silicon group substituents include trimethylsilyl and phenyloctylsilyl groups.

In each occurrence, germanium groups are germanium-containing groups, which include, but are not limited to, germyl groups such as alkylgermyl groups, arylgermyl groups, arylalkylgermyl groups, germyloxy groups, and the like, which in each occurrence have from 1 to 20 carbon atoms.

In each occurrence, tin groups are tin-containing groups, which include, but are not limited to, stannyl groups such as alkylstannyl groups, arylstannyl groups, arylalkylstannyl groups, stannoxy (or "stannyloxy") groups, and the like, which in each occurrence have from 1 to 20 carbon atoms. Thus, tin groups include, but are not limited to, stannoxy groups.

In each occurrence, lead groups are lead-containing groups, which include, but are not limited to, alkyllead groups, aryllead groups, arylalkyllead groups, and the like, which in each occurrence, have from 1 to 20 carbon atoms.

In each occurrence, boron groups are boron-containing groups, which include, but are not limited to, —$BR^A_2$, —$BX_2$, —$BR^AX$, and the like, wherein X is a monoanionic group such as hydride, alkoxide, alkyl thiolate, and the like, and wherein $R^A$ in each occurrence can be alkyl, cycloalkyl, aryl, aralkyl, substituted alkyl, substituted aryl, or substituted aralkyl having from 1 to 20 carbon atoms.

In each occurrence, aluminum groups are aluminum-containing groups, which include, but are not limited to, —$AlR^A$, —$AlX_2$, —$AlR^AX$, wherein X is a monoanionic group such as hydride, alkoxide, alkyl thiolate, and the like, and wherein $R^A$ in each occurrence can be alkyl, cycloalkyl, aryl, aralkyl, substituted alkyl, substituted aryl, or substituted aralkyl having from 1 to 20 carbon atoms.

Examples of inorganic groups that may be used as substituents, in each occurrence include, but are not limited to, —$OAlX_2$, —$OSiX_3$, —$OPX_2$, —$SX$, —$AsX_2$, —$PX_2$, and the like, wherein X is a monoanionic group such as hydride, amide, alkoxide, alkyl thiolate, and the like, and wherein any alkyl, cycloalkyl, aryl, aralkyl, substituted alkyl, substituted aryl, or substituted aralkyl group or substituent on these ligands has from 1 to 20 carbon atoms.

Examples of organometallic groups that may be used as substituents, in each occurrence, include, but are not limited to, organoboron groups, organoaluminum groups, organogallium groups, organosilicon groups, organogermanium groups, organotin groups, organolead groups, organo-transition metal groups, and the like, having from 1 to 20 carbon atoms.

Formula (I), depicted above, illustrates that the dinuclear compounds of the present invention are homonuclear, because each metallocene moiety linked by the alkenyl linking group is the same and contains the same metal center. M can be Zr, Hf, or Ti in the present invention. In a different aspect, M is either Hf or Ti.

In the alkenyl linking group, E is either carbon or silicon. $R^X$, $R^Y$, and $R^Z$ in the alkenyl linking group independently are selected from a hydrogen atom, or a substituted or unsubstituted aliphatic, aromatic, or cyclic group, or a combination thereof. In one aspect of the present invention, $R^X$, $R^Y$, and $R^Z$ independently are a substituted or unsubstituted aliphatic group having from 1 to 20 carbon atoms. For example, $R^X$, $R^Y$, and $R^Z$ can be selected independently from methyl, ethyl, propyl, butyl, pentyl, hexyl, heptyl, octyl, nonyl, decyl, or trimethylsilylmethyl. In another aspect, $R^X$, $R^Y$, and $R^Z$ are hydrogen atoms. $R^X$, $R^Y$, and $R^Z$ independently are a substituted or unsubstituted aromatic group, for example, having up to 20 carbon atoms, in yet another aspect of the present invention.

$R^X$, $R^Y$, and $R^Z$ independently are a methyl, ethyl, propyl, butyl, pentyl, hexyl, phenyl, naphthyl, tolyl, benzyl, cyclopentyl, cyclohexyl, or cyclohexylphenyl group, or a hydrogen atom, in other aspects of this invention. Further, $R^X$, $R^Y$, and $R^Z$ independently can be methyl, phenyl, benzyl, or a hydrogen atom in another aspect of the present invention.

The integer n in formula (I) determines the length of the alkenyl linking group and ranges from 0 to 12, inclusive. In one aspect of this invention, n is equal to 0, 1, 2, 3, 4, 5, 6, or 7. In a different aspect of the present invention, n is 1, 2, 3, 4, or 5. The integer n can be 1, 2, or 3 in other aspects of this invention.

According to yet another aspect of the present invention, both $X^1$ and $X^2$ are methyl groups, phenyl groups, or chlorine atoms. In this aspect, $X^4$ is a substituted cyclopentadienyl group, and $X^3$ is a substituted fluorenyl group. In one aspect, the substituted fluorenyl group is substituted with two butyl substituents, for example, two tert-butyl substituents. In these and other aspects, M is Zr or Hf; n is 1, 2, 3, or 4; $R^X$, $R^Y$, and $R^Z$ are hydrogen atoms; and $A^1$ is a carbon bridging atom having either two methyl or two phenyl substituents.

In accordance with another aspect of the present invention, both $X^1$ and $X^2$ in formula (I) are chlorine atoms. In this aspect, n is in range from 1 to 10, inclusive. In a different aspect, $X^1$ and $X^2$ are chlorine atoms; either $X^3$ or $X^4$ is a substituted cyclopentadienyl group, and the other is a substituted fluorenyl group; $A^1$ is a silicon or carbon bridging atom, optionally substituted with one or more methyl or phenyl substituents; $R^X$, $R^Y$, and $R^Z$ are hydrogen atoms; M is Zr, Hf, or Ti; and n is either 1, 2, 3, 4, or 5.

An example of a dinuclear compound in accordance with the present invention is the following compound, which is abbreviated "DMET 1" throughout this disclosure:

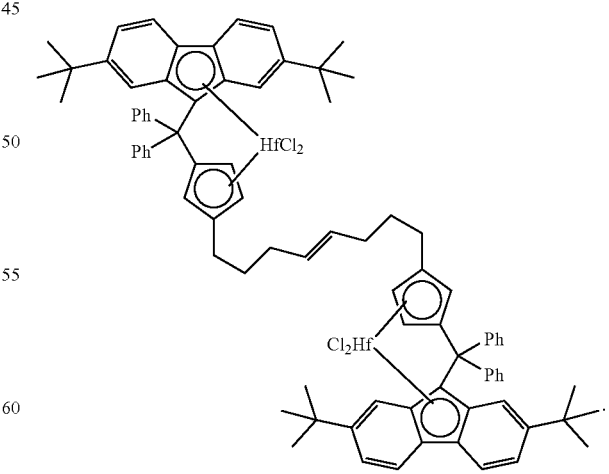

Applicants have used the abbreviation Ph for phenyl. Other illustrative and non-limiting examples of dinuclear compounds of the present invention include the following:

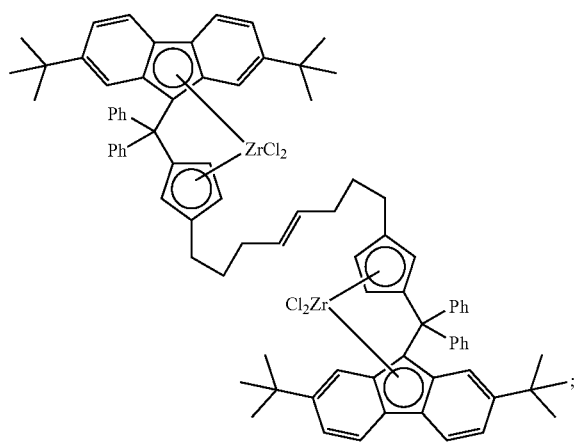
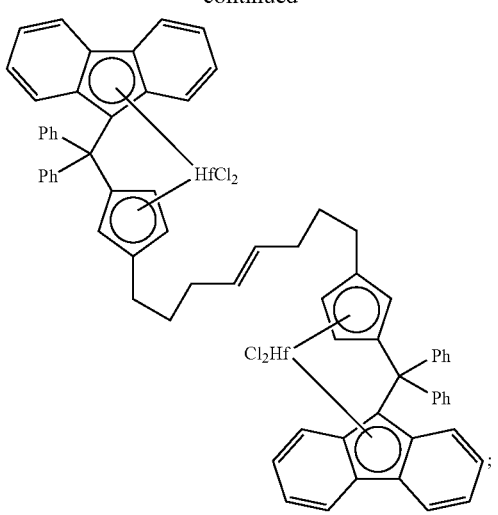
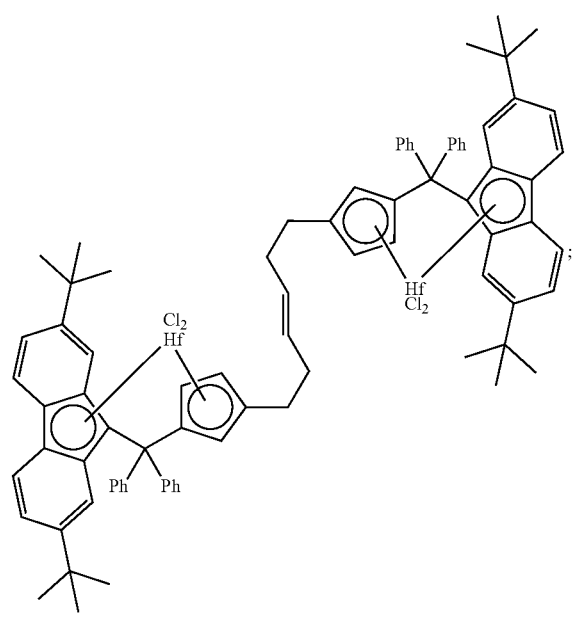
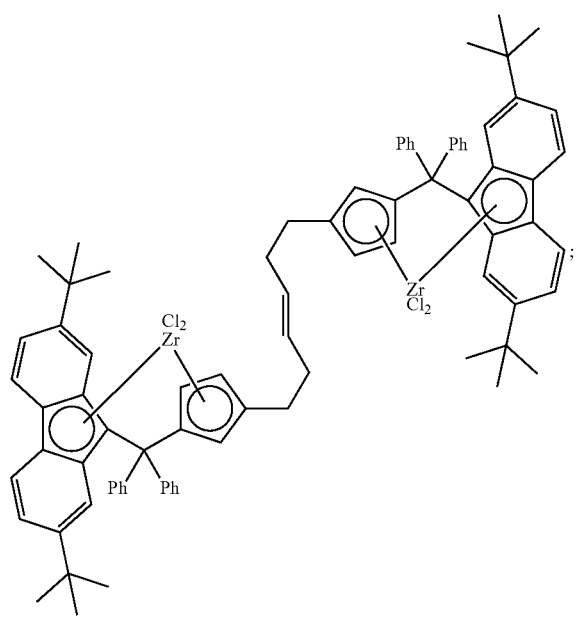
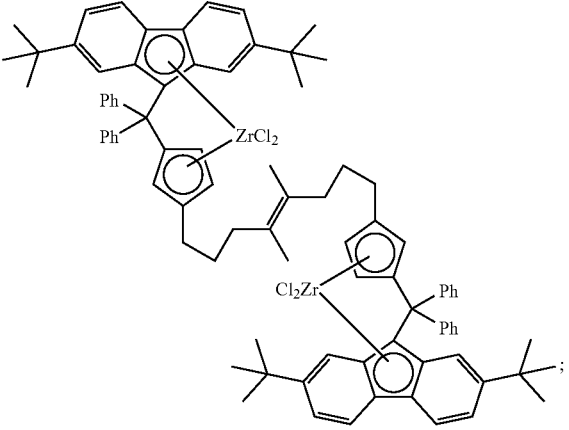

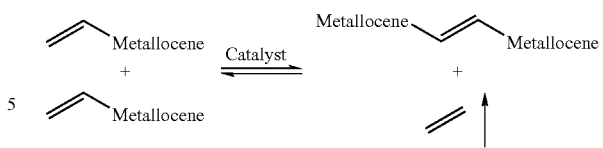

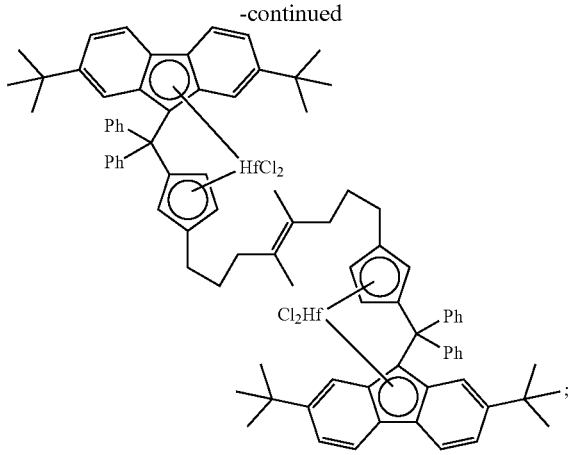

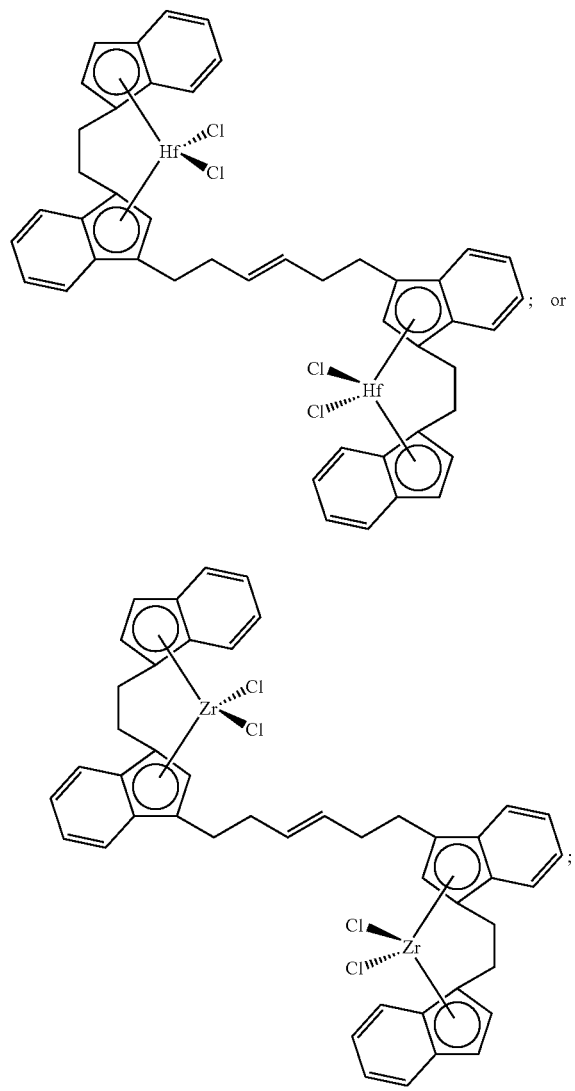

and the like. Applicants have used the abbreviation Ph for phenyl.

Methods of making a dinuclear compound of the present invention are also provided. One such method for synthesizing a dinuclear metallocene compound is illustrated in the general reaction scheme provided below:

A metallocene catalyst having an alkenyl substituent is linked to itself via the olefin metathesis reaction in the presence of a suitable catalyst. Generally, the alkenyl substituent can be of any length, and can be, for example, a substituent on a cyclopentadienyl-type group (e.g., cyclopentadienyl, indenyl, fluorenyl). In the reaction product, the metallocene moieties are connected by an alkenyl linking group. Ethylene gas is also produced in this reaction.

Various metal-based catalysts can be employed in an olefin metathesis reaction. The metals often used include ruthenium, tungsten, molybdenum, and nickel. In the examples that follow, a Grubbs 1st Generation Metathesis Catalyst based on ruthenium was employed, but this invention is not limited to any particular metathesis catalyst.

Metathesis reactions can be conducted in the presence of a solvent such as, for example, aliphatic, aromatic, or saturated ester solvents. Suitable solvents useful in the production of dinuclear metallocene compounds include, but are not limited to, benzene, toluene, heptane, isobutane, methylene chloride, and the like. Solvent selection can depend upon many factors, for instance, the desired reaction temperature and solubility of either the metallocene reactant or the dinuclear metallocene in the particular solvent.

Suitable olefin metathesis reaction temperatures to produce dinuclear metallocene compounds of the present invention are generally in a range from about −50° C. to about 150° C. For example, the reaction temperature can be in the range from about 0° C. to about 100° C. The reaction temperature selected is often a compromise between many variables, such as the solvent employed, reaction pressure, reaction time, quantity and type of catalyst, product yield and selectivity, and isomer ratio, if desired. Further, the metathesis reaction equilibrium can be driven towards the dinuclear metallocene product if ethylene gas is removed or vented from the reaction system.

Generally, there is no limitation on the selection of the metallocene compound that can be used to form the dinuclear compounds of the present invention, other than the presence of an alkenyl substituent on a cyclopentadienyl, indenyl, or fluorenyl group. Some examples of metallocene compounds that can be used to produce dinuclear compounds of the present invention via the olefin metathesis reaction scheme above include, but are not limited to:

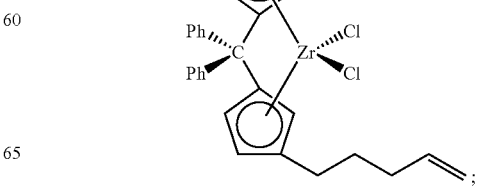

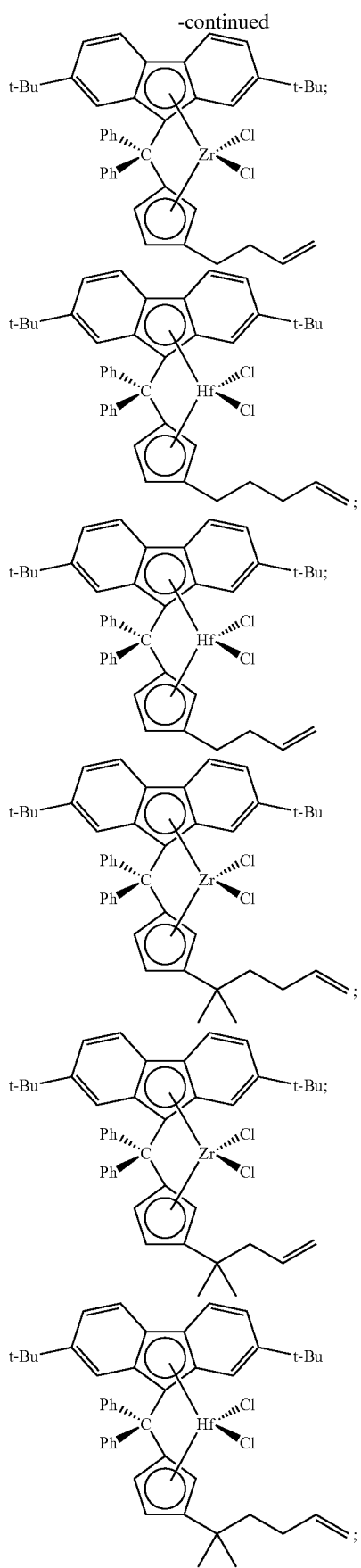
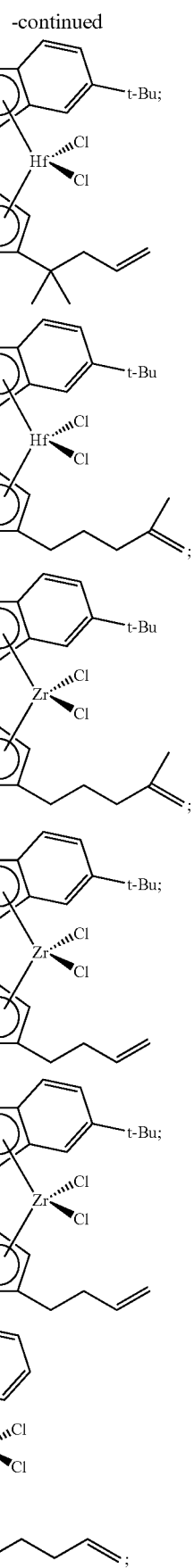

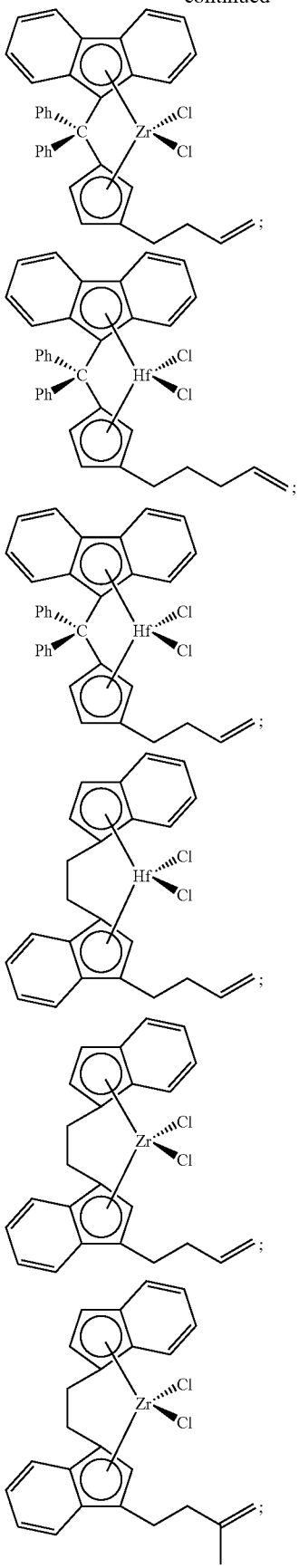

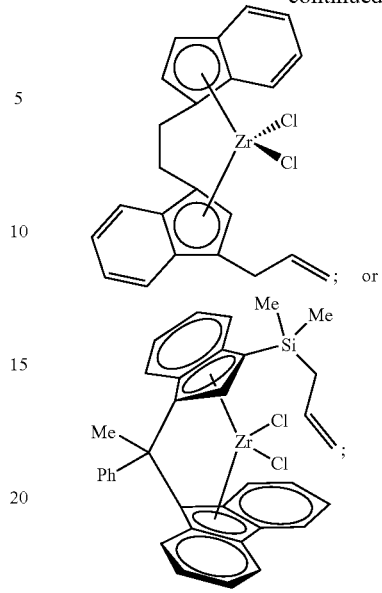

and the like. Applicants have used the abbreviations Ph for phenyl, Me for methyl, and t-Bu for tert-butyl.

Additional bridged metallocene compounds can be used to produce dinuclear compounds of the present invention. Therefore, the scope of the present invention is not limited to the starting metallocene species provided above.

Catalyst Composition

The present invention also relates to catalyst compositions employing dinuclear metallocene compounds. According to one aspect of the present invention, a catalyst composition is provided which comprises a contact product of at least one dinuclear metallocene compound and at least one activator-support. This catalyst composition can further comprise at least one organoaluminum compound. These catalyst compositions can be utilized to produce polyolefins, both homopolymers and copolymers, for a variety of end-use applications. The at least one dinuclear metallocene compound in these catalyst compositions has the formula:

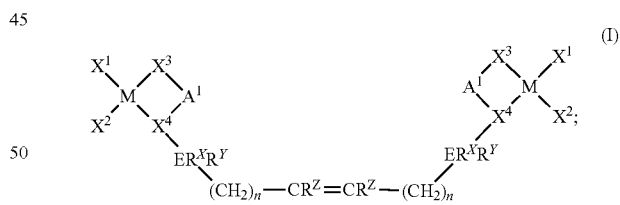

wherein:

$X^1$ and $X^2$ independently are a halide or a substituted or unsubstituted aliphatic, aromatic, or cyclic group, or a combination thereof;

$X^3$ is a substituted cyclopentadienyl, indenyl, or fluorenyl group, any substituents on $X^3$ other than a bridging group independently are a hydrogen atom or a substituted or unsubstituted alkyl or alkenyl group;

$X^4$ is a substituted cyclopentadienyl, indenyl, or fluorenyl group, any substituents on $X^4$ other than the bridging group and an alkenyl linking group independently are a hydrogen atom or a substituted or unsubstituted alkyl or alkenyl group;

$A^1$ is a substituted or unsubstituted bridging group comprising either a cyclic group of 5 to 8 carbon atoms, a bridging chain of 2 to 5 carbon atoms, or a carbon, silicon, germanium, tin, boron, nitrogen, or phosphorus bridging atom, any substituents on $A^1$ independently are a hydrogen atom, or a substituted or unsubstituted aliphatic, aromatic, or cyclic group, or a combination thereof;

M is Zr, Hf, or Ti;

E is carbon or silicon;

$R^X$, $R^Y$, and $R^Z$ independently are a hydrogen atom, or a substituted or unsubstituted aliphatic, aromatic, or cyclic group, or a combination thereof; and n is an integer in a range from 0 to 12, inclusive.

with the proviso that $A^1$ is not a silicon bridging atom when both $X^1$ and $X^2$ are chlorine atoms, both $X^3$ and $X^4$ are cyclopentadienyl groups, E is carbon, $R^X$, $R^Y$, and $R^Z$ are each hydrogen atoms, and n is equal to 0.

In accordance with this and other aspects of the present invention, it is contemplated that the catalyst compositions disclosed herein can contain more than one dinuclear metallocene compound and/or more than one activator-support. Additionally, more than one organoaluminum compound is also contemplated.

In another aspect of the present invention, a catalyst composition is provided which comprises a contact product of at least one dinuclear metallocene compound, at least one activator-support, and at least one organoaluminum compound, wherein this catalyst composition is substantially free of aluminoxanes, organozinc compounds, organoboron or organoborate compounds, and ionizing ionic compounds. In this aspect, the catalyst composition has catalyst activity, to be discussed below, in the absence of these additional co-catalysts.

However, in other aspects of this invention, these co-catalysts can be employed. For example, a catalyst composition comprising at least one dinuclear metallocene compound and at least one activator-support can further comprise at least one optional co-catalyst. Suitable co-catalysts in this aspect include, but are not limited to, aluminoxane compounds, organozinc compounds, organoboron or organoborate compounds, ionizing ionic compounds, and the like, or any combination thereof. More than one co-catalyst can be present in the catalyst composition.

In a different aspect, a catalyst composition is provided which does not require an activator-support. Such a catalyst composition comprises the contact product of at least one dinuclear metallocene compound and at least one compound selected from at least one aluminoxane compound, at least one organozinc compound, at least one organoboron or organoborate compound, at least one ionizing ionic compound, or combinations thereof. In this aspect, the at least one dinuclear metallocene compound is selected from:

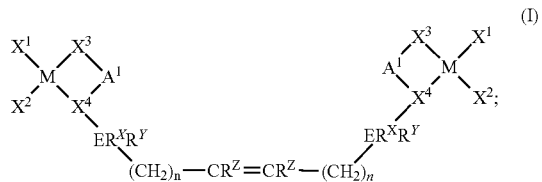

wherein:

$X^1$ and $X^2$ independently are a halide or a substituted or unsubstituted aliphatic, aromatic, or cyclic group, or a combination thereof;

$X^3$ is a substituted cyclopentadienyl, indenyl, or fluorenyl group, any substituents on $X^3$ other than a bridging group independently are a hydrogen atom or a substituted or unsubstituted alkyl or alkenyl group;

$X^4$ is a substituted cyclopentadienyl, indenyl, or fluorenyl group, any substituents on $X^4$ other than the bridging group and an alkenyl linking group independently are a hydrogen atom or a substituted or unsubstituted alkyl or alkenyl group;

$A^1$ is a substituted or unsubstituted bridging group comprising either a cyclic group of 5 to 8 carbon atoms, a bridging chain of 2 to 5 carbon atoms, or a carbon, silicon, germanium, tin, boron, nitrogen, or phosphorus bridging atom, any substituents on $A^1$ independently are a hydrogen atom, or a substituted or unsubstituted aliphatic, aromatic, or cyclic group, or a combination thereof;

M is Zr, Hf, or Ti;

E is carbon or silicon;

$R^X$, $R^Y$, and $R^Z$ independently are a hydrogen atom, or a substituted or unsubstituted aliphatic, aromatic, or cyclic group, or a combination thereof; and n is an integer in a range from 0 to 12, inclusive.

with the proviso that $A^1$ is not a silicon bridging atom when both $X^1$ and $X^2$ are chlorine atoms, both $X^3$ and $X^4$ are cyclopentadienyl groups, E is carbon, $R^X$, $R^Y$, and $R^Z$ are each hydrogen atoms, and n is equal to 0.

Activator-Support

The present invention encompasses various catalyst compositions which can include an activator-support. In one aspect, the activator-support comprises a chemically-treated solid oxide. Alternatively, the activator-support can comprise a clay mineral, a pillared clay, an exfoliated clay, an exfoliated clay gelled into another oxide matrix, a layered silicate mineral, a non-layered silicate mineral, a layered aluminosilicate mineral, a non-layered aluminosilicate mineral, or any combination thereof.

The chemically-treated solid oxide exhibits enhanced acidity as compared to the corresponding untreated solid oxide compound. The chemically-treated solid oxide also functions as a catalyst activator as compared to the corresponding untreated solid oxide. While the chemically-treated solid oxide activates the metallocene in the absence of co-catalysts, it is not necessary to eliminate co-catalysts from the catalyst composition. The activation function of the activator-support is evident in the enhanced activity of catalyst composition as a whole, as compared to a catalyst composition containing the corresponding untreated solid oxide. However, it is believed that the chemically-treated solid oxide can function as an activator, even in the absence of an organoaluminum compound, aluminoxanes, organoboron compounds, ionizing ionic compounds, and the like.

The chemically-treated solid oxide can comprise at least one solid oxide treated with at least one electron-withdrawing anion. While not intending to be bound by the following statement, it is believed that treatment of the solid oxide with an electron-withdrawing component augments or enhances the acidity of the oxide. Thus, either the activator-support exhibits Lewis or Brønsted acidity that is typically greater than the Lewis or Brønsted acid strength of the untreated solid oxide, or the activator-support has a greater number of acid sites than the untreated solid oxide, or both. One method to quantify the acidity of the chemically-treated and untreated solid oxide materials is by comparing the polymerization activities of the treated and untreated oxides under acid catalyzed reactions.

The chemically-treated solid oxide of this invention is formed generally from an inorganic solid oxide that exhibits Lewis acidic or Brønsted acidic behavior and has a relatively high porosity. The solid oxide is chemically-treated with an electron-withdrawing component, typically an electron-withdrawing anion, to form an activator-support.

According to one aspect of the present invention, the solid oxide used to prepare the chemically-treated solid oxide has a pore volume greater than about 0.1 cc/g. According to another aspect of the present invention, the solid oxide has a pore volume greater than about 0.5 cc/g. According to yet another aspect of the present invention, the solid oxide has a pore volume greater than about 1.0 cc/g.

In another aspect, the solid oxide has a surface area of from about 100 to about 1000 m$^2$/g. In yet another aspect, the solid oxide has a surface area of from about 200 to about 800 m$^2$/g. In still another aspect of the present invention, the solid oxide has a surface area of from about 250 to about 600 m$^2$/g.

The chemically-treated solid oxide can comprise a solid inorganic oxide comprising oxygen and at least one element selected from Group 2, 3, 4, 5, 6, 7, 8, 9, 10, 11, 12, 13, 14, or 15 of the periodic table, or comprising oxygen and at least one element selected from the lanthanide or actinide elements. (See: Hawley's Condensed Chemical Dictionary, 11$^{th}$ Ed., John Wiley & Sons; 1995; Cotton, F. A.; Wilkinson, G.; Murillo; C. A.; and Bochmann; M. Advanced Inorganic Chemistry, 6$^{th}$ Ed., Wiley-Interscience, 1999.) For example, the inorganic oxide can comprise oxygen and at least one element selected from Al, B, Be, Bi, Cd, Co, Cr, Cu, Fe, Ga, La, Mn, Mo, Ni, Sb, Si, Sn, Sr, Th, Ti, V, W, P, Y, Zn or Zr.

Suitable examples of solid oxide materials or compounds that can be used to form the chemically-treated solid oxide include, but are not limited to, $Al_2O_3$, $B_2O_3$, BeO, $Bi_2O_3$, CdO, $Co_3O_4$, $Cr_2O_3$, CuO, $Fe_2O_3$, $Ga_2O_3$, $La_2O_3$, $Mn_2O_3$, $MoO_3$, NiO, $P_2O_5$, $Sb_2O_5$, $SiO_2$, $SnO_2$, SrO, $ThO_2$, $TiO_2$, $V_2O_5$, $WO_3$, $Y_2O_3$, ZnO, $ZrO_2$, and the like, including mixed oxides thereof, and combinations thereof. For example, the solid oxide can be silica, alumina, silica-alumina, aluminum phosphate, heteropolytungstates, titania, zirconia, magnesia, boria, zinc oxide, mixed oxides thereof, or any combination thereof.

The solid oxide of this invention encompasses oxide materials such as alumina, "mixed oxide" compounds thereof such as silica-alumina, and combinations and mixtures thereof. The mixed oxide compounds such as silica-alumina can be single or multiple chemical phases with more than one metal combined with oxygen to form a solid oxide compound. Examples of mixed oxides that can be used in the activator-support of the present invention include, but are not limited to, silica-alumina, silica-titania, silica-zirconia, zeolites, various clay minerals, alumina-titania, alumina-zirconia, zinc-aluminate, and the like.

The electron-withdrawing component used to treat the solid oxide can be any component that increases the Lewis or Brønsted acidity of the solid oxide upon treatment (as compared to the solid oxide that is not treated with at least one electron-withdrawing anion). According to one aspect of the present invention, the electron-withdrawing component is an electron-withdrawing anion derived from a salt, an acid, or other compound, such as a volatile organic compound, that serves as a source or precursor for that anion. Examples of electron-withdrawing anions include, but are not limited to, sulfate, bisulfate, fluoride, chloride, bromide, iodide, fluorosulfate, fluoroborate, phosphate, fluorophosphate, trifluoroacetate, triflate, fluorozirconate, fluorotitanate, trifluoroacetate, triflate, and the like, including mixtures and combinations thereof. In addition, other ionic or non-ionic compounds that serve as sources for these electron-withdrawing anions also can be employed in the present invention.

Thus, for example, the chemically-treated solid oxide used in the catalyst compositions of the present can be fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, and the like, or combinations thereof.

When the electron-withdrawing component comprises a salt of an electron-withdrawing anion, the counterion or cation of that salt can be selected from any cation that allows the salt to revert or decompose back to the acid during calcining. Factors that dictate the suitability of the particular salt to serve as a source for the electron-withdrawing anion include, but are not limited to, the solubility of the salt in the desired solvent, the lack of adverse reactivity of the cation, ion-pairing effects between the cation and anion, hygroscopic properties imparted to the salt by the cation, and the like, and thermal stability of the anion. Examples of suitable cations in the salt of the electron-withdrawing anion include, but are not limited to, ammonium, trialkyl ammonium, tetraalkyl ammonium, tetraalkyl phosphonium, $H^+$, $[H(OEt_2)_2]^+$, and the like.

Further, combinations of one or more different electron-withdrawing anions, in varying proportions, can be used to tailor the specific acidity of the activator-support to the desired level. Combinations of electron-withdrawing components can be contacted with the oxide material simultaneously or individually, and in any order that affords the desired chemically-treated solid oxide acidity. For example, one aspect of this invention is employing two or more electron-withdrawing anion source compounds in two or more separate contacting steps.

Thus, one example of such a process by which an chemically-treated solid oxide is prepared is as follows: a selected solid oxide compound, or combination of oxide compounds, is contacted with a first electron-withdrawing anion source compound to form a first mixture; this first mixture is calcined and then contacted with a second electron-withdrawing anion source compound to form a second mixture; the second mixture is then calcined to form a treated solid oxide compound. In such a process, the first and second electron-withdrawing anion source compounds are either the same or different compounds.

According to another aspect of the present invention, the chemically-treated solid oxide comprises a solid inorganic oxide material, a mixed oxide material, or a combination of inorganic oxide materials, that is chemically-treated with an electron-withdrawing component, and optionally treated with a metal source, including metal salts, metal ions, or other metal-containing compounds. Non-limiting examples of the metal or metal ion include zinc, nickel, vanadium, titanium, silver, copper, gallium, tin, tungsten, molybdenum, and the like, or combinations thereof. Examples of chemically-treated solid oxides that contain a metal or metal ion include, but are not limited to, zinc-impregnated chlorided alumina, titanium-impregnated fluorided alumina, zinc-impregnated fluorided alumina, zinc-impregnated chlorided silica-alumina, zinc-impregnated fluorided silica-alumina, zinc-impregnated sulfated alumina, chlorided zinc aluminate, fluorided zinc aluminate, sulfated zinc aluminate, and the like, or any combination thereof.

Any method of impregnating the solid oxide material with a metal can be used. The method by which the oxide is contacted with a metal source, typically a salt or metal-containing compound, can include, but is not limited to, gelling, co-gelling, impregnation of one compound onto another, and the like. If desired, the metal-containing compound is added to or impregnated into the solid oxide in solution form, and subsequently converted into the supported metal upon calcining. Accordingly, the solid inorganic oxide can further comprise a metal selected from zinc, titanium, nickel, vanadium, silver, copper, gallium, tin, tungsten, molybdenum, and the like, or combinations of these metals. For example, zinc is often used to impregnate the solid oxide because it can provide improved catalyst activity at a low cost.

The solid oxide can be treated with metal salts or metal-containing compounds before, after, or at the same time that the solid oxide is treated with the electron-withdrawing anion. Following any contacting method, the contacted mixture of oxide compound, electron-withdrawing anion, and the metal ion is typically calcined. Alternatively, a solid oxide material, an electron-withdrawing anion source, and the metal salt or metal-containing compound are contacted and calcined simultaneously.

Various processes are used to form the chemically-treated solid oxide useful in the present invention. The chemically-treated solid oxide can comprise the contact product of at least one solid oxide compound and at least one electron-withdrawing anion source. It is not required that the solid oxide compound be calcined prior to contacting the electron-withdrawing anion source. The contact product typically is calcined either during or after the solid oxide compound is contacted with the electron-withdrawing anion source. The solid oxide compound can be calcined or uncalcined. Various processes to prepare solid oxide activator-supports that can be employed in this invention have been reported. For example, such methods are described in U.S. Pat. Nos. 6,107,230, 6,165,929, 6,294,494, 6,300,271, 6,316,553, 6,355,594, 6,376,415, 6,388,017, 6,391,816, 6,395,666, 6,524,987, 6,548,441, 6,548,442, 6,576,583, 6,613,712, 6,632,894, 6,667,274, and 6,750,302, the disclosures of which are incorporated herein by reference in their entirety.

According to one aspect of the present invention, the solid oxide material is chemically-treated by contacting it with at least one electron-withdrawing component, typically an electron-withdrawing anion source. Further, the solid oxide material optionally is chemically treated with a metal ion, and then calcined to form a metal-containing or metal-impregnated chemically-treated solid oxide. According to another aspect of the present invention, the solid oxide material and electron-withdrawing anion source are contacted and calcined simultaneously.

The method by which the oxide is contacted with the electron-withdrawing component, typically a salt or an acid of an electron-withdrawing anion, can include, but is not limited to, gelling, co-gelling, impregnation of one compound onto another, and the like. Thus, following any contacting method, the contacted mixture of the solid oxide, electron-withdrawing anion, and optional metal ion, is calcined.

The solid oxide activator-support (i.e., chemically-treated solid oxide) thus can be produced by a process comprising:

1) contacting a solid oxide compound with at least one electron-withdrawing anion source compound to form a first mixture; and 2) calcining the first mixture to form the solid oxide activator-support.

According to another aspect of the present invention, the solid oxide activator-support (chemically-treated solid oxide) is produced by a process comprising:

1) contacting at least one solid oxide compound with a first electron-withdrawing anion source compound to form a first mixture;

2) calcining the first mixture to produce a calcined first mixture;

3) contacting the calcined first mixture with a second electron-withdrawing anion source compound to form a second mixture; and 4) calcining the second mixture to form the solid oxide activator-support.

According to yet another aspect of the present invention, the chemically-treated solid oxide is produced or formed by contacting the solid oxide with the electron-withdrawing anion source compound, where the solid oxide compound is calcined before, during, or after contacting the electron-withdrawing anion source, and where there is a substantial absence of aluminoxanes, organoboron or organoborate compounds, and ionizing ionic compounds.

Calcining of the treated solid oxide generally is conducted in an ambient atmosphere, typically in a dry ambient atmosphere, at a temperature from about 200° C. to about 900° C., and for a time of about 1 minute to about 100 hours. Calcining can be conducted at a temperature of from about 300° C. to about 800° C., or alternatively, at a temperature of from about 400° C. to about 700° C. Calcining can be conducted for about 1 hour to about 50 hours, or for about 3 hours to about 20 hours. Thus, for example, calcining can be carried out for about 1 to about 10 hours at a temperature of from about 350° C. to about 550° C. Any suitable ambient atmosphere can be employed during calcining. Generally, calcining is conducted in an oxidizing atmosphere, such as air. Alternatively, an inert atmosphere, such as nitrogen or argon, or a reducing atmosphere, such as hydrogen or carbon monoxide, can be used.

According to one aspect of the present invention, the solid oxide material is treated with a source of halide ion, sulfate ion, or a combination of anions, optionally treated with a metal ion, and then calcined to provide the chemically-treated solid oxide in the form of a particulate solid. For example, the solid oxide material is treated with a source of sulfate (termed a "sulfating agent"), a source of chloride ion (termed a "chloriding agent"), a source of fluoride ion (termed a "fluoriding agent"), or a combination thereof, and calcined to provide the solid oxide activator. Useful acidic activator-supports include, but are not limited to, bromided alumina, chlorided alumina, fluorided alumina, sulfated alumina, bromided silica-alumina, chlorided silica-alumina, fluorided silica-alumina, sulfated silica-alumina, bromided silica-zirconia, chlorided silica-zirconia, fluorided silica-zirconia, sulfated silica-zirconia; a pillared clay, such as a pillared montmorillonite, optionally treated with fluoride, chloride, or sulfate; phosphated alumina or other aluminophosphates optionally treated with sulfate, fluoride, or chloride; or any combination of the above. Further, any of these activator-supports optionally can be treated with a metal ion.

The chemically-treated solid oxide can comprise a fluorided solid oxide in the form of a particulate solid. The fluorided solid oxide can be formed by contacting a solid oxide with a fluoriding agent. The fluoride ion can be added to the oxide by forming a slurry of the oxide in a suitable solvent such as alcohol or water including, but not limited to, the one to three carbon alcohols because of their volatility and low surface tension. Examples of suitable fluoriding agents include, but are not limited to, hydrofluoric acid (HF), ammonium fluoride ($NH_4F$), ammonium bifluoride ($NH_4HF_2$), ammonium tetrafluoroborate ($NH_4BF_4$), ammonium silicofluoride (hexafluorosilicate) (($NH_4)_2SiF_6$), ammonium hexafluorophosphate ($NH_4PF_6$), analogs thereof, and combinations thereof. For example, ammonium bifluoride $NH_4HF_2$ can be used as the fluoriding agent, due to its ease of use and availability.

If desired, the solid oxide is treated with a fluoriding agent during the calcining step. Any fluoriding agent capable of thoroughly contacting the solid oxide during the calcining step can be used. For example, in addition to those fluoriding agents described previously, volatile organic fluoriding agents can be used. Examples of volatile organic fluoriding agents useful in this aspect of the invention include, but are not limited to, freons, perfluorohexane, perfluorobenzene, fluoromethane, trifluoroethanol, an the like, and combinations thereof. Gaseous hydrogen fluoride or fluorine itself also can be used with the solid oxide if fluorided while calcining. One convenient method of contacting the solid oxide with the fluoriding agent is to vaporize a fluoriding agent into a gas stream used to fluidize the solid oxide during calcination.

Similarly, in another aspect of this invention, the chemically-treated solid oxide comprises a chlorided solid oxide in the form of a particulate solid. The chlorided solid oxide is formed by contacting a solid oxide with a chloriding agent. The chloride ion can be added to the oxide by forming a slurry of the oxide in a suitable solvent. The solid oxide can be treated with a chloriding agent during the calcining step. Any chloriding agent capable of serving as a source of chloride and thoroughly contacting the oxide during the calcining step can be used. For example, volatile organic chloriding agents can be used. Examples of suitable volatile organic chloriding agents include, but are not limited to, certain freons, perchlorobenzene, chloromethane, dichloromethane, chloroform, carbon tetrachloride, trichloroethanol, and the like, or any combination thereof. Gaseous hydrogen chloride or chlorine itself also can be used with the solid oxide during calcining. One convenient method of contacting the oxide with the chloriding agent is to vaporize a chloriding agent into a gas stream used to fluidize the solid oxide while calcination.

The amount of fluoride or chloride ion present before calcining the solid oxide generally is from about 2 to about 50% by weight, where weight percent is based on the weight of the solid oxide, for example, silica-alumina, before calcining. According to another aspect of this invention, the amount of fluoride or chloride ion present before calcining the solid oxide is from about 3 to about 25% by weight, and according to another aspect of this invention, from about 4 to about 20% by weight. Once impregnated with halide, the halided oxide can be dried by any suitable method including, but not limited to, suction filtration followed by evaporation, drying under vacuum, spray drying, and the like, although it is also possible to initiate the calcining step immediately without drying the impregnated solid oxide.

The silica-alumina used to prepare the treated silica-alumina typically has a pore volume greater than about 0.5 cc/g. According to one aspect of the present invention, the pore volume is greater than about 0.8 cc/g, and according to another aspect of the present invention, greater than about 1.0 cc/g. Further, the silica-alumina generally has a surface area greater than about 100 m$^2$/g. According to another aspect of this invention, the surface area is greater than about 250 m$^2$/g. Yet, in another aspect, the surface area is greater than about 350 m$^2$/g.

The silica-alumina utilized in the present invention typically has an alumina content from about 5 to about 95% by weight. According to one aspect of this invention, the alumina content of the silica-alumina is from about 5 to about 50%, or from about 8% to about 30%, alumina by weight. According to yet another aspect of this invention, the solid oxide component comprises alumina without silica, and according to another aspect of this invention, the solid oxide component comprises silica without alumina.

The sulfated solid oxide comprises sulfate and a solid oxide component, such as alumina or silica-alumina, in the form of a particulate solid. Optionally, the sulfated oxide is treated further with a metal ion such that the calcined sulfated oxide comprises a metal. According to one aspect of the present invention, the sulfated solid oxide comprises sulfate and alumina. In some instances, the sulfated alumina is formed by a process wherein the alumina is treated with a sulfate source, for example, sulfuric acid or a sulfate salt such as ammonium sulfate. This process is generally performed by forming a slurry of the alumina in a suitable solvent, such as alcohol or water, in which the desired concentration of the sulfating agent has been added. Suitable organic solvents include, but are not limited to, the one to three carbon alcohols because of their volatility and low surface tension.

According to one aspect of this invention, the amount of sulfate ion present before calcining is from about 0.5 parts by weight to about 100 parts by weight sulfate ion to about 100 parts by weight solid oxide. According to another aspect of this invention, the amount of sulfate ion present before calcining is from about 1 part by weight to about 50 parts by weight sulfate ion to about 100 parts by weight solid oxide, and according to still another aspect of this invention, from about 5 parts by weight to about 30 parts by weight sulfate ion to about 100 parts by weight solid oxide. These weight ratios are based on the weight of the solid oxide before calcining. Once impregnated with sulfate, the sulfated oxide can be dried by any suitable method including, but not limited to, suction filtration followed by evaporation, drying under vacuum, spray drying, and the like, although it is also possible to initiate the calcining step immediately.

According to another aspect of the present invention, the activator-support used in preparing the catalyst compositions of this invention comprises an ion-exchangeable activator-support, including but not limited to silicate and aluminosilicate compounds or minerals, either with layered or non-layered structures, and combinations thereof. In another aspect of this invention, ion-exchangeable, layered aluminosilicates such as pillared clays are used as activator-supports. When the acidic activator-support comprises an ion-exchangeable activator-support, it can optionally be treated with at least one electron-withdrawing anion such as those disclosed herein, though typically the ion-exchangeable activator-support is not treated with an electron-withdrawing anion.

According to another aspect of the present invention, the activator-support of this invention comprises clay minerals having exchangeable cations and layers capable of expanding. Typical clay mineral activator-supports include, but are not limited to, ion-exchangeable, layered aluminosilicates such as pillared clays. Although the term "support" is used, it is not meant to be construed as an inert component of the catalyst composition, but rather is to be considered an active part of the catalyst composition, because of its intimate association with the dinuclear metallocene component.

According to another aspect of the present invention, the clay materials of this invention encompass materials either in their natural state or that have been treated with various ions by wetting, ion exchange, or pillaring. Typically, the clay material activator-support of this invention comprises clays that have been ion exchanged with large cations, including polynuclear, highly charged metal complex cations. However, the clay material activator-supports of this invention also encompass clays that have been ion exchanged with simple salts, including, but not limited to, salts of Al(III), Fe(II), Fe(III) and Zn(II) with ligands such as halide, acetate, sulfate, nitrate, or nitrite.

According to another aspect of the present invention, activator-support comprises a pillared clay. The term "pillared clay" is used to refer to clay materials that have been ion exchanged with large, typically polynuclear, highly charged metal complex cations. Examples of such ions include, but are not limited to, Keggin ions which can have charges such as 7+, various polyoxometallates, and other large ions. Thus, the term pillaring refers to a simple exchange reaction in which the exchangeable cations of a clay material are replaced with large, highly charged ions, such as Keggin ions. These polymeric cations are then immobilized within the interlayers of the clay and when calcined are converted to metal oxide "pillars," effectively supporting the clay layers as column-like structures. Thus, once the clay is dried and calcined to produce the supporting pillars between clay layers, the expanded lattice structure is maintained and the porosity is enhanced. The resulting pores can vary in shape and size as a function of the pillaring material and the parent clay material used. Examples of pillaring and pillared clays are found in: T. J. Pinnavaia, Science 220 (4595), 365-371 (1983); J. M. Thomas, Intercalation Chemistry, (S. Whittington and A. Jacobson, eds.) Ch. 3, pp. 55-99, Academic Press, Inc., (1972); U.S. Pat. No. 4,452,910; U.S. Pat. No. 5,376,611; and U.S. Pat. No. 4,060,480; the disclosures of which are incorporated herein by reference in their entirety.

The pillaring process utilizes clay minerals having exchangeable cations and layers capable of expanding. Any pillared clay that can enhance the polymerization of olefins in the catalyst composition of the present invention can be used. Therefore, suitable clay minerals for pillaring include, but are not limited to, allophanes; smectites, both dioctahedral (Al) and tri-octahedral (Mg) and derivatives thereof such as montmorillonites (bentonites), nontronites, hectorites, or laponites; halloysites; vermiculites; micas; fluoromicas; chlorites; mixed-layer clays; the fibrous clays including but not limited to sepiolites, attapulgites, and palygorskites; a serpentine clay; illite; laponite; saponite; and any combination thereof. In one aspect, the pillared clay activator-support comprises bentonite or montmorillonite. The principal component of bentonite is montmorillonite.

The pillared clay can be pretreated if desired. For example, a pillared bentonite is pretreated by drying at about 300° C. under an inert atmosphere, typically dry nitrogen, for about 3 hours, before being added to the polymerization reactor. Although an exemplary pretreatment is described herein, it should be understood that the preheating can be carried out at many other temperatures and times, including any combination of temperature and time steps, all of which are encompassed by this invention.

The activator-support used to prepare the catalyst compositions of the present invention can be combined with other inorganic support materials, including, but not limited to, zeolites, inorganic oxides, phosphated inorganic oxides, and the like. In one aspect, typical support materials that are used include, but are not limited to, silica, silica-alumina, alumina, titania, zirconia, magnesia, boria, thoria, aluminophosphate, aluminum phosphate, silica-titania, coprecipitated silica/titania, mixtures thereof, or any combination thereof.

According to yet another aspect of the present invention, one or more of the dinuclear metallocene compounds can be precontacted with an olefin monomer and an organoaluminum compound for a first period of time prior to contacting this mixture with the activator-support. Once the precontacted mixture of the metallocene compound(s), olefin monomer, and organoaluminum compound is contacted with the activator-support, the composition further comprising the activator-support is termed the "postcontacted" mixture. The postcontacted mixture can be allowed to remain in further contact for a second period of time prior to being charged into the reactor in which the polymerization process will be carried out.

Organoaluminum Compounds

In one aspect, organoaluminum compounds that can be used with the present invention include, but are not limited to, compounds having the formula:

where $R^2$ is an aliphatic group having from 2 to 6 carbon atoms. For example, $R^2$ can be ethyl, propyl, butyl, hexyl, or isobutyl.

Other organoaluminum compounds which can be used in accordance with the present invention include, but are not limited to, compounds having the formula:

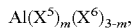

where $X^5$ is a hydrocarbyl; $X^6$ is an alkoxide or an aryloxide, a halide, or a hydride; and m is from 1 to 3, inclusive.

In one aspect, $X^5$ is a hydrocarbyl having from 1 to about 20 carbon atoms. In another aspect of the present invention, $X^5$ is an alkyl having from 1 to 10 carbon atoms. For example, $X^5$ can be ethyl, propyl, n-butyl, sec-butyl, isobutyl, or hexyl, and the like, in yet another aspect of the present invention.

According to one aspect of the present invention, $X^6$ is an alkoxide or an aryloxide, any one of which has from 1 to 20 carbon atoms, a halide, or a hydride. In another aspect of the present invention, $X^6$ is selected independently from fluorine or chlorine. Yet, in another aspect, $X^6$ is chlorine.

In the formula, $Al(X^5)_m(X^6)_{3-m}$, m is a number from 1 to 3, inclusive, and typically, m is 3. The value of m is not restricted to be an integer; therefore, this formula includes sesquihalide compounds or other organoaluminum cluster compounds.

Examples of organoaluminum compounds suitable for use in accordance with the present invention include, but are not limited to, trialkylaluminum compounds, dialkylaluminium halide compounds, dialkylaluminum alkoxide compounds, dialkylaluminum hydride compounds, and combinations thereof. Specific non-limiting examples of suitable organoaluminum compounds include trimethylaluminum (TMA), triethylaluminum (TEA), tripropylaluminum, diethylaluminum ethoxide, tributylaluminum, diisobutylaluminum hydride, triisobutylaluminum, diethylaluminum chloride, and the like, or combinations thereof.

The present invention contemplates precontacting at least one dinuclear metallocene compound with at least one organoaluminum compound and an olefin monomer to form a precontacted mixture, prior to contacting this precontacted mixture with the activator-support to form a catalyst composition. When the catalyst composition is prepared in this manner, typically, though not necessarily, a portion of the organoaluminum compound is added to the precontacted mixture and another portion of the organoaluminum compound is added to the postcontacted mixture prepared when the precontacted mixture is contacted with the solid oxide activator-support. However, the entire organoaluminum compound can be used to prepare the catalyst composition in either the precontacting or postcontacting step. Alternatively, all the catalyst components are contacted in a single step.

Further, more than one organoaluminum compound can be used in either the precontacting or the postcontacting step. When an organoaluminum compound is added in multiple steps, the amounts of organoaluminum compound disclosed herein include the total amount of organoaluminum compound used in both the precontacted and postcontacted mixtures, and any additional organoaluminum compound added to the polymerization reactor. Therefore, total amounts of organoaluminum compounds are disclosed regardless of whether a single organoaluminum compound or more than one organoaluminum compound is used.

Aluminoxane Compounds

The present invention further provides a catalyst composition which can comprise an aluminoxane compound. As used herein, the term "aluminoxane" refers to aluminoxane compounds, compositions, mixtures, or discrete species, regardless of how such aluminoxanes are prepared, formed or otherwise provided. For example, a catalyst composition comprising an aluminoxane compound can be prepared in which aluminoxane is provided as the poly(hydrocarbyl aluminum oxide), or in which aluminoxane is provided as the combination of an aluminum alkyl compound and a source of active protons such as water. Aluminoxanes are also referred to as poly(hydrocarbyl aluminum oxides) or organoaluminoxanes.

The other catalyst components typically are contacted with the aluminoxane in a saturated hydrocarbon compound solvent, though any solvent that is substantially inert to the reactants, intermediates, and products of the activation step can be used. The catalyst composition formed in this manner is collected by any suitable method, for example, by filtration. Alternatively, the catalyst composition is introduced into the polymerization reactor without being isolated.

The aluminoxane compound of this invention can be an oligomeric aluminum compound comprising linear structures, cyclic structures, or cage structures, or mixtures of all three. Cyclic aluminoxane compounds having the formula:

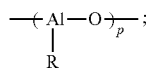

wherein R is a linear or branched alkyl having from 1 to 10 carbon atoms, and p is an integer from 3 to 20, are encompassed by this invention. The AlRO moiety shown here also constitutes the repeating unit in a linear aluminoxane. Thus, linear aluminoxanes having the formula:

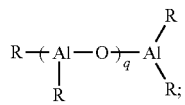

wherein R is a linear or branched alkyl having from 1 to 10 carbon atoms, and q is an integer from 1 to 50, are also encompassed by this invention.

Further, aluminoxanes can have cage structures of the formula $R^t_{5r+\alpha}R^b_{r-\alpha}Al_{4r}O_{3r}$, wherein $R^t$ is a terminal linear or branched alkyl group having from 1 to 10 carbon atoms; $R^b$ is a bridging linear or branched alkyl group having from 1 to 10 carbon atoms; r is 3 or 4; and α is equal to $n_{Al(3)} - n_{O(2)} + n_{O(4)}$, wherein $n_{Al(3)}$ is the number of three coordinate aluminum atoms, $n_{O(2)}$ is the number of two coordinate oxygen atoms, and $n_{O(4)}$ is the number of 4 coordinate oxygen atoms.

Thus, aluminoxanes which can be employed in the catalyst compositions of the present invention are represented generally by formulas such as $(R-Al-O)_p$, $R(R-Al-O)_qAlR_2$, and the like. In these formulas, the R group is typically a linear or branched $C_1$-$C_6$ alkyl, such as methyl, ethyl, propyl, butyl, pentyl, or hexyl. Examples of aluminoxane compounds that can be used in accordance with the present invention include, but are not limited to, methylaluminoxane, ethylaluminoxane, n-propylaluminoxane, iso-propylaluminoxane, n-butylaluminoxane, t-butyl-aluminoxane, sec-butylaluminoxane, iso-butylaluminoxane, 1-pentylaluminoxane, 2-pentylaluminoxane, 3-pentylaluminoxane, isopentylaluminoxane, neopentylaluminoxane, and the like, or any combination thereof. Methyl aluminoxane, ethyl aluminoxane, and isobutyl aluminoxane are prepared from trimethylaluminum, triethylaluminum, or triisobutylaluminum, respectively, and sometimes are referred to as poly(methyl aluminum oxide), poly(ethyl aluminum oxide), and poly(isobutyl aluminum oxide), respectively. It is also within the scope of the invention to use an aluminoxane in combination with a trialkylaluminum, such as that disclosed in U.S. Pat. No. 4,794,096, incorporated herein by reference in its entirety.

The present invention contemplates many values of p and q in the aluminoxane formulas $(R-Al-O)_p$ and $R(R-Al-O)_qAlR_2$, respectively. Is some aspects, p and q are at least 3. However, depending upon how the organoaluminoxane is prepared, stored, and used, the value of p and q can vary within a single sample of aluminoxane, and such combinations of organoaluminoxanes are contemplated herein.

In preparing a catalyst composition containing an aluminoxane, the molar ratio of the total moles of aluminum in the aluminoxane (or aluminoxanes) to the total moles of dinuclear metallocene compound (or compounds) in the composition is generally between about 1:10 and about 100,000:1. In another aspect, the molar ratio is in a range from about 5:1 to about 15,000:1. Optionally, aluminoxane can be added to a polymerization zone in ranges from about 0.01 mg/L to about 1000 mg/L, from about 0.1 mg/L to about 100 mg/L, or from about 1 mg/L to about 50 mg/L.

Organoaluminoxanes can be prepared by various procedures. Examples of organoaluminoxane preparations are disclosed in U.S. Pat. Nos. 3,242,099 and 4,808,561, the disclosures of which are incorporated herein by reference in their entirety. For example, water in an inert organic solvent can be reacted with an aluminum alkyl compound, such as $(R^2)_3Al$, to form the desired organoaluminoxane compound. While not intending to be bound by this statement, it is believed that this synthetic method can afford a mixture of both linear and cyclic R—Al—O aluminoxane species, both of which are encompassed by this invention. Alternatively, organoaluminoxanes are prepared by reacting an aluminum alkyl compound, such as $(R^2)_3Al$ with a hydrated salt, such as hydrated copper sulfate, in an inert organic solvent.

Organoboron/Organoborate Compounds

According to another aspect of the present invention, a catalyst composition comprising organoboron or organoborate compounds is provided. Such compounds include neutral boron compounds, borate salts, and the like, or combinations thereof. For example, fluoroorgano boron compounds and fluoroorgano borate compounds are contemplated.

Any fluoroorgano boron or fluoroorgano borate compound can be utilized with the present invention. Examples of fluoroorgano borate compounds that can be used in the present invention include, but are not limited to, fluorinated aryl borates such as N,N-dimethylanilinium tetrakis(pentafluorophenyl)borate, triphenylcarbenium tetrakis(pentafluorophenyl)borate, lithium tetrakis(pentafluorophenyl)borate, N,N-dimethylanilinium tetrakis[3,5-bis(trifluoromethyl)phenyl]borate, triphenylcarbenium tetrakis[3,5-bis(trifluoromethyl)phenyl]borate, and the like, or mixtures thereof. Examples of fluoroorgano boron compounds that can be used as co-catalysts in the present invention include, but are not limited to, tris(pentafluorophenyl)boron, tris[3,5-bis(trifluoromethyl)phenyl]boron, and the like, or mixtures thereof. Although not intending to be bound by the following theory, these examples of fluoroorgano borate and fluoroorgano boron compounds, and related compounds, are thought to form "weakly-coordinating" anions when combined with organometal or metallocene compounds, as disclosed in U.S. Pat. No. 5,919,983, the disclosure of which is incorporated herein by reference in its entirety. Applicants also contemplate the use of diboron, or bis-boron, compounds or other bifunctional compounds containing two or more boron atoms in the chemical structure, such as disclosed in J. Am. Chem. Soc., 2005, 127, pp. 14756-14768, the content of which is incorporated herein by reference in its entirety.

Generally, any amount of organoboron compound can be used. According to one aspect of this invention, the molar ratio of the total moles of organoboron or organoborate compound (or compounds) to the total moles of dinuclear metallocene compound (or compounds) in the catalyst composition is in a range from about 0.1:1 to about 15:1. Typically, the amount of the fluoroorgano boron or fluoroorgano borate compound used as a co-catalyst for the dinuclear metallocene is from about 0.5 moles to about 10 moles of boron/borate compound per mole of dinuclear metallocene compound. According to another aspect of this invention, the amount of fluoroorgano boron or fluoroorgano borate compound is from about 0.8 moles to about 5 moles of boron/borate compound per mole of dinuclear metallocene compound.

Ionizing Ionic Compounds

The present invention further provides a catalyst composition comprising an ionizing ionic compound. An ionizing ionic compound is an ionic compound that can function as a co-catalyst to enhance the activity of the catalyst composition. While not intending to be bound by theory, it is believed that the ionizing ionic compound is capable of reacting with a metallocene compound and converting the metallocene into one or more cationic metallocene compounds, or incipient cationic metallocene compounds. Again, while not intending to be bound by theory, it is believed that the ionizing ionic compound can function as an ionizing compound by completely or partially extracting an anionic ligand, possibly a non-alkadienyl ligand such as $X^1$ or $X^2$, from the metallocene. However, the ionizing ionic compound is an activator regardless of whether it is ionizes the dinuclear metallocene, abstracts an $X^1$ or $X^2$ ligand in a fashion as to form an ion pair, weakens the metal-$X^1$ or metal-$X^2$ bond in the dinuclear metallocene, simply coordinates to an $X^1$ or $X^2$ ligand, or activates the metallocene by some other mechanism.

Further, it is not necessary that the ionizing ionic compound activate the metallocene compounds only. The activation function of the ionizing ionic compound can be evident in the enhanced activity of catalyst composition as a whole, as compared to a catalyst composition that does not contain an ionizing ionic compound.

Examples of ionizing ionic compounds include, but are not limited to, the following compounds: tri(n-butyl)ammonium tetrakis(p-tolyl)borate, tri(n-butyl)ammonium tetrakis(m-tolyl)borate, tri(n-butyl)ammonium tetrakis(2,4-dimethylphenyl)borate, tri(n-butyl)ammonium tetrakis(3,5-dimethylphenyl)borate, tri(n-butyl)ammonium tetrakis[3,5-bis(trifluoromethyl)phenyl]borate, tri(n-butyl)ammonium tetrakis(pentafluorophenyl)borate, N,N-dimethylanilinium tetrakis(p-tolyl)borate, N,N-dimethylanilinium tetrakis(m-tolyl)borate, N,N-dimethylanilinium tetrakis(2,4-dimethylphenyl)borate, N,N-dimethylanilinium tetrakis(3,5-dimethylphenyl)borate, N,N-dimethylanilinium tetrakis[3,5-bis(trifluoromethyl)phenyl]borate, N,N-dimethylanilinium tetrakis(pentafluorophenyl)borate, triphenylcarbenium tetrakis(p-tolyl)borate, triphenylcarbenium tetrakis(m-tolyl)borate, triphenylcarbenium tetrakis(2,4-dimethylphenyl)borate, triphenylcarbenium tetrakis(3,5-dimethylphenyl) borate, triphenylcarbenium tetrakis[3,5-bis(trifluoromethyl)phenyl]borate, triphenylcarbenium tetrakis(pentafluorophenyl)borate, tropylium tetrakis(p-tolyl)borate, tropylium tetrakis(m-tolyl)borate, tropylium tetrakis(2,4-dimethylphenyl)borate, tropylium tetrakis(3,5-dimethylphenyl)borate, tropylium tetrakis[3,5-bis(trifluoro-methyl)phenyl]borate, tropylium tetrakis(pentafluorophenyl)borate, lithium tetrakis(pentafluorophenyl)borate, lithium tetraphenylborate, lithium tetrakis(p-tolyl)borate, lithium tetrakis(m-tolyl)borate, lithium tetrakis(2,4-dimethylphenyl)borate, lithium tetrakis(3,5-dimethylphenyl)borate, lithium tetrafluoroborate, sodium tetrakis(pentafluorophenyl)borate, sodium tetraphenylborate, sodium tetrakis(p-tolyl)borate, sodium tetrakis(m-tolyl)borate, sodium tetrakis(2,4-dimethylphenyl)borate, sodium tetrakis(3,5-dimethylphenyl)borate, sodium tetrafluoroborate, potassium tetrakis-(pentafluorophenyl)borate, potassium tetraphenylborate, potassium tetrakis(p-tolyl)borate, potassium tetrakis(m-tolyl)borate, potassium tetrakis(2,4-dimethyl-phenyl)borate, potassium tetrakis(3,5-dimethylphenyl)borate, potassium tetrafluoroborate, lithium tetrakis(pentafluorophenyl)aluminate, lithium tetraphenylaluminate, lithium tetrakis(p-tolyl)aluminate, lithium tetrakis(m-tolyl)aluminate, lithium tetrakis(2,4-dimethylphenyl)aluminate, lithium tetrakis(3,5-dimethylphenyl)aluminate, lithium tetrafluoroaluminate, sodium tetrakis(pentafluoro-phenyl)aluminate, sodium tetraphenylaluminate, sodium tetrakis(p-tolyl)aluminate, sodium tetrakis (m-tolyl)aluminate, sodium tetrakis(2,4-dimethylphenyl) aluminate, sodium tetrakis(3,5-dimethylphenyl)aluminate, sodium tetrafluoroaluminate, potassium tetrakis(pentafluorophenyl)aluminate, potassium tetraphenylaluminate, potassium tetrakis(p-tolyl)aluminate, potassium tetrakis(m-tolyl) aluminate, potassium tetrakis(2,4-dimethylphenyl) aluminate, potassium tetrakis (3,5-dimethylphenyl) aluminate, potassium tetrafluoroaluminate, and the like, or combinations thereof. Ionizing ionic compounds useful in this invention are not limited to these; other examples of ionizing ionic compounds are disclosed in U.S. Pat. Nos. 5,576,259 and 5,807,938, the disclosures of which are incorporated herein by reference in their entirety.

Olefin Monomers

Unsaturated reactants that can be employed with catalyst compositions and polymerization processes of this invention typically include olefin compounds having from about 2 to 30 carbon atoms per molecule and having at least one olefinic double bond. This invention encompasses homopolymerization processes using a single olefin such as ethylene or propylene, as well as copolymerization reactions with at least one different olefinic compound. The resulting copolymers generally contain a major amount of ethylene (>50 mole percent) and a minor amount of comonomer (<50 mole percent), though this is not a requirement. The comonomers that can be copolymerized with ethylene often have from 3 to 20 carbon atoms in their molecular chain.

Acyclic, cyclic, polycyclic, terminal (α), internal, linear, branched, substituted, unsubstituted, functionalized, and non-functionalized olefins can be employed in this invention. For example, typical unsaturated compounds that can be polymerized with the catalyst compositions of this invention include, but are not limited to, ethylene, propylene, 1-butene, 2-butene, 3-methyl-1-butene, isobutylene, 1-pentene, 2-pentene, 3-methyl-1-pentene, 4-methyl-1-pentene, 1-hexene, 2-hexene, 3-hexene, 3-ethyl-1-hexene, 1-heptene, 2-heptene, 3-heptene, the four normal octenes, the four normal nonenes, the five normal decenes, and the like, or mixtures of two or more of these compounds. Cyclic and bicyclic olefins, including but not limited to, cyclopentene, cyclohexene, norbornylene, norbornadiene, and the like, can also be polymerized as described above. Styrene can also be employed as a monomer.

When a copolymer is desired, the monomer can be, for example, ethylene or propylene, which is copolymerized with a comonomer. Examples of olefin comonomers include, but are not limited to, 1-butene, 2-butene, 3-methyl-1-butene, isobutylene, 1-pentene, 2-pentene, 3-methyl-1-pentene, 4-methyl-1-pentene, 1-hexene, 2-hexene, 3-ethyl-1-hexene, 1-heptene, 2-heptene, 3-heptene, 1-octene, and the like. According to one aspect of the present invention, the comonomer is selected from 1-butene, 1-pentene, 1-hexene, 1-octene, 1-decene, or styrene.

Generally, the amount of comonomer introduced into a reactor zone to produce the copolymer is from about 0.01 to about 50 weight percent of the comonomer based on the total weight of the monomer and comonomer. According to another aspect of the present invention, the amount of comonomer introduced into a reactor zone is from about 0.01 to about 40 weight percent comonomer based on the total weight of the monomer and comonomer. In still another aspect, the amount of comonomer introduced into a reactor zone is from about 0.1 to about 35 weight percent comonomer based on the total weight of the monomer and comonomer. Yet, in another aspect, the amount of comonomer introduced into a reactor zone is from about 0.5 to about 20 weight percent comonomer based on the total weight of the monomer and comonomer.

While not intending to be bound by this theory, where branched, substituted, or functionalized olefins are used as reactants, it is believed that a steric hindrance can impede and/or slow the polymerization process. Thus, branched and/or cyclic portion(s) of the olefin removed somewhat from the carbon-carbon double bond would not be expected to hinder the reaction in the way that the same olefin substituents situated more proximate to the carbon-carbon double bond might. According to one aspect of the present invention, at least one monomer/reactant is ethylene, so the polymerizations are either a homopolymerization involving only ethylene, or copolymerizations with a different acyclic, cyclic, terminal, internal, linear, branched, substituted, or unsubstituted olefin. In addition, the catalyst compositions of this invention can be used in the polymerization of diolefin compounds including, but not limited to, 1,3-butadiene, isoprene, 1,4-pentadiene, and 1,5-hexadiene.

Preparation of the Catalyst Composition

In one aspect, the present invention encompasses a catalyst composition comprising a contact product of a dinuclear metallocene compound and an activator-support. Such a composition can further comprise an organoaluminum compound. Additionally, this catalyst composition can further comprise at least one optional co-catalyst, wherein the at least one optional co-catalyst is at least one aluminoxane compound, at least one organozinc compound, at least one organoboron or organoborate compound, at least one ionizing ionic compound, or any combination thereof. In another aspect, a catalyst composition is provided which comprises the contact product of at least one dinuclear metallocene compound and at least one compound selected from at least one aluminoxane compound, at least one organozinc compound, at least one organoboron or organoborate compound, at least one ionizing ionic compound, or any combination thereof.

This invention further encompasses methods of making these catalyst compositions, such as, for example, contacting the respective catalyst components in any order or sequence.

The at least one dinuclear metallocene compound can be precontacted with an olefinic monomer if desired, not necessarily the olefin monomer to be polymerized, and an organoaluminum compound for a first period of time prior to contacting this precontacted mixture with an activator-support. The first period of time for contact, the precontact time, between the metallocene compound or compounds, the olefinic monomer, and the organoaluminum compound typically ranges from a time period of about 0.1 hour to about 24 hours, for example, from about 0.1 to about 1 hour. Precontact times from about 10 minutes to about 30 minutes are also employed.

Alternatively, the precontacting process is carried out in multiple steps, rather than a single step, in which multiple mixtures are prepared, each comprising a different set of catalyst components. For example, at least two catalyst components are contacted forming a first mixture, followed by contacting the first mixture with at least one other catalyst component forming a second mixture, and so forth.

Multiple precontacting steps can be carried out in a single vessel or in multiple vessels. Further, multiple precontacting steps can be carried out in series (sequentially), in parallel, or a combination thereof. For example, a first mixture of two catalyst components can be formed in a first vessel, a second mixture comprising the first mixture plus one additional catalyst component can be formed in the first vessel or in a second vessel, which is typically placed downstream of the first vessel.

In another aspect, one or more of the catalyst components can be split and used in different precontacting treatments. For example, part of a catalyst component is fed into a first precontacting vessel for precontacting with at least one other catalyst component, while the remainder of that same catalyst component is fed into a second precontacting vessel for precontacting with at least one other catalyst component, or is fed directly into the reactor, or a combination thereof. The precontacting can be carried out in any suitable equipment, such as tanks, stirred mix tanks, various static mixing devices, a flask, a vessel of any type, or combinations of these apparatus.

In another aspect of this invention, the various catalyst components (for example, dinuclear metallocene, activator-support, organoaluminum co-catalyst, and optionally an unsaturated hydrocarbon) are contacted in the polymerization reactor simultaneously while the polymerization reaction is proceeding. Alternatively, any two or more of these catalyst components can be precontacted in a vessel prior to entering the reaction zone. This precontacting step can be continuous, in which the precontacted product is fed continuously to the reactor, or it can be a stepwise or batchwise process in which a batch of precontacted product is added to make a catalyst composition. This precontacting step can be carried out over a time period that can range from a few seconds to as much as several days, or longer. In this aspect, the continuous precontacting step generally lasts from about 1 second to about 1 hour. In another aspect, the continuous precontacting step lasts from about 10 seconds to about 45 minutes, or from about 1 minute to about 30 minutes.

Once the precontacted mixture of the metallocene compound, olefin monomer, and organoaluminum co-catalyst is contacted with the activator-support, this composition (with the addition of the activator-support) is termed the "postcontacted mixture." The postcontacted mixture optionally remains in contact for a second period of time, the postcontact time, prior to initiating the polymerization process. Postcontact times between the precontacted mixture and the activator-support generally range from about 0.1 hour to about 24 hours. In a further aspect, the postcontact time is in a range from about 0.1 hour to about 1 hour. The precontacting step, the postcontacting step, or both, can increase the productivity of the polymer as compared to the same catalyst composition that is prepared without precontacting or postcontacting. However, neither a precontacting step nor a postcontacting step is required.

The postcontacted mixture can be heated at a temperature and for a time period sufficient to allow adsorption, impregnation, or interaction of precontacted mixture and the activator-support, such that a portion of the components of the precontacted mixture is immobilized, adsorbed, or deposited thereon. Where heating is employed, the postcontacted mixture generally is heated to a temperature of from between about 0° F. to about 150° F., or from about 40° F. to about 95° F.

According to one aspect of this invention, the molar ratio of the moles of dinuclear metallocene compound to the moles of organoaluminum compound in a catalyst composition generally is in a range from about 1:1 to about 1:10,000. In another aspect, the molar ratio is in a range from about 1:1 to about 1:1,000. Yet, in another aspect, the molar ratio of the moles of dinuclear metallocene compound to the moles of organoaluminum compound is in a range from about 1:1 to about 1:100. These molar ratios reflect the ratio of total moles of dinuclear metallocene compound or compounds to the total amount of organoaluminum compound (or compounds) in both the precontacted mixture and the postcontacted mixture combined, if precontacting and/or postcontacting steps are employed.

When a precontacting step is used, the molar ratio of the total moles of olefin monomer to total moles of dinuclear metallocene in the precontacted mixture is typically in a range from about 1:10 to about 100,000:1. Total moles of each component are used in this ratio to account for aspects of this invention where more than one olefin monomer and/or more than dinuclear metallocene is employed. Further, this molar ratio can be in a range from about 10:1 to about 1,000:1 in another aspect of the invention.

Generally, the weight ratio of organoaluminum compound to activator-support is in a range from about 10:1 to about 1:1000. If more than one organoaluminum compound and/or more than one activator-support is employed, this ratio is based on the total weight of each respective component. In another aspect, the weight ratio of the organoaluminum compound to the activator-support is in a range from about 3:1 to about 1:100, or from about 1:1 to about 1:50.

In some aspects of this invention, the weight ratio of dinuclear metallocene to activator-support is in a range from about 1:1 to about 1:1,000,000. If more than one dinuclear metallocene and/or more than one activator-support is employed, this ratio is based on the total weight of each respective component. In another aspect, this weight ratio is in a range from about 1:5 to about 1:100,000, or from about 1:10 to about 1:10,000. Yet, in another aspect, the weight ratio of the dinuclear metallocene compound to the activator-support is in a range from about 1:20 to about 1:1000.

According to some aspects of this invention, aluminoxane compounds are not required to form the catalyst composition. Thus, the polymerization proceeds in the absence of aluminoxanes. Accordingly, the present invention can use, for example, organoaluminum compounds and an activator-support in the absence of aluminoxanes. While not intending to be bound by theory, it is believed that the organoaluminum compound likely does not activate the metallocene catalyst in the same manner as an organoaluminoxane compound.

Additionally, in some aspects, organoboron and organoborate compounds are not required to form a catalyst composition of this invention. Nonetheless, aluminoxanes, organozinc compounds, organoboron or organoborate compounds, ionizing ionic compounds, or combinations thereof can be used in other catalyst compositions contemplated by and encompassed within the present invention. Hence, co-catalysts such as aluminoxanes, organozinc compounds, organoboron or organoborate compounds, ionizing ionic compounds, or combinations thereof, can be employed with the dinuclear metallocene compound, either in the presence or in the absence of an activator-support, and either in the presence or in the absence of an organoaluminum compound.

Catalyst compositions of the present invention generally have a catalyst activity greater than about 100 grams of polyethylene per gram of activator-support per hour (abbreviated gP/(gAS·hr)). In another aspect, the catalyst activity is greater than about 150, greater than about 200, or greater than about 250 gP/(gAS·hr). In still another aspect, catalyst compositions of this invention are characterized by having a catalyst activity greater than about 500, greater than about 1000, or greater than about 1500 gP/(gAS·hr). Yet, in another aspect, the catalyst activity is greater than about 2000 gP/(gAS·hr). This activity is measured under slurry polymerization conditions using isobutane as the diluent, at a polymerization temperature of about 90° C. and an ethylene pressure of about 550 psig.

Other aspects of the present invention do not require an activator-support. These catalyst compositions comprise a contact product of at least one dinuclear metallocene compound and at least one compound selected from at least one aluminoxane compound, at least one organozinc compound, at least one organoboron or organoborate compound, at least one ionizing ionic compound, or any combination thereof. Such catalyst compositions of the present invention generally have catalyst activities greater than about 100 grams of polyethylene per hour per gram of the respective aluminoxane compound, organozinc compound, organoboron or organoborate compound, ionizing ionic compound, or combination thereof. In another aspect, the catalyst activity is greater than about 250, or greater than about 500 grams of polyethylene per hour per gram of the respective aluminoxane compound, organozinc compound, organoboron or organoborate compound, ionizing ionic compound, or combination thereof. Yet, in another aspect, the catalyst activity is greater than about 1000, or greater than about 2000 grams of polyethylene per hour.

As discussed above, any combination of the dinuclear metallocene compound, the activator-support, the organoaluminum compound, and the olefin monomer, can be precontacted in some aspects of this invention. When any precontacting occurs with an olefinic monomer, it is not necessary that the olefin monomer used in the precontacting step be the same as the olefin to be polymerized. Further, when a precontacting step among any combination of the catalyst components is employed for a first period of time, this precontacted mixture can be used in a subsequent postcontacting step between any other combination of catalyst components for a second period of time. For example, the dinuclear metallocene compound, the organoaluminum compound, and 1-hexene can be used in a precontacting step for a first period of time, and this precontacted mixture then can be contacted with the activator-support to form a postcontacted mixture that is contacted for a second period of time prior to initiating the polymerization reaction. For example, the first period of time for contact, the precontact time, between any combination of the metallocene compound, the olefinic monomer, the activator-support, and the organoaluminum compound can be from about 0.1 hour to about 24 hours, from about 0.1 to about 1 hour, or from about 10 minutes to about 30 minutes. The postcontacted mixture optionally is allowed to remain in contact for a second period of time, the postcontact time, prior to initiating the polymerization process. According to one aspect of this invention, postcontact times between the precontacted mixture and any remaining catalyst components is from about 0.1 hour to about 24 hours, or from about 0.1 hour to about 1 hour.

Polymerization Process

Catalyst compositions of the present invention can be used to polymerize olefins to form homopolymers or copolymers. One such process for polymerizing olefins in the presence of a catalyst composition of the present invention comprises contacting the catalyst composition with at least one olefin monomer and optionally at least one olefin comonomer under polymerization conditions to produce a polymer or copolymer, wherein the catalyst composition comprises a contact product of at least one dinuclear metallocene compound and at least one activator-support. The at least one dinuclear metallocene compound is selected from the following formula:

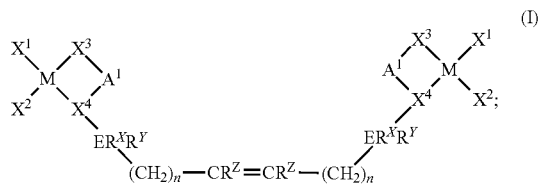

wherein:

$X^1$ and $X^2$ independently are a halide or a substituted or unsubstituted aliphatic, aromatic, or cyclic group, or a combination thereof;

$X^3$ is a substituted cyclopentadienyl, indenyl, or fluorenyl group, any substituents on $X^3$ other than a bridging group independently are a hydrogen atom or a substituted or unsubstituted alkyl or alkenyl group;

$X^4$ is a substituted cyclopentadienyl, indenyl, or fluorenyl group, any substituents on $X^4$ other than the bridging group and an alkenyl linking group independently are a hydrogen atom or a substituted or unsubstituted alkyl or alkenyl group;

$A^1$ is a substituted or unsubstituted bridging group comprising either a cyclic group of 5 to 8 carbon atoms, a bridging chain of 2 to 5 carbon atoms, or a carbon, silicon, germanium, tin, boron, nitrogen, or phosphorus bridging atom, any substituents on $A^1$ independently are a hydrogen atom, or a substituted or unsubstituted aliphatic, aromatic, or cyclic group, or a combination thereof;

M is Zr, Hf, or Ti;

E is carbon or silicon;

$R^X$, $R^Y$, and $R^Z$ independently are a hydrogen atom, or a substituted or unsubstituted aliphatic, aromatic, or cyclic group, or a combination thereof; and n is an integer in a range from 0 to 12, inclusive.

with the proviso that $A^1$ is not a silicon bridging atom when both $X^1$ and $X^2$ are chlorine atoms, both $X^3$ and $X^4$ are cyclopentadienyl groups, E is carbon, $R^X$, $R^Y$, and $R^Z$ are each hydrogen atoms, and n is equal to 0.

The catalyst compositions of the present invention are intended for any olefin polymerization method using various types of polymerization reactors. As used herein, "polymerization reactor" includes any polymerization reactor capable of polymerizing olefin monomers to produce homopolymers or copolymers. Such homopolymers and copolymers are referred to as resins or polymers. The various types of reactors include those that may be referred to as batch, slurry, gas-phase, solution, high pressure, tubular or autoclave reactors. Gas phase reactors may comprise fluidized bed reactors or staged horizontal reactors. Slurry reactors may comprise vertical or horizontal loops. High pressure reactors may comprise autoclave or tubular reactors. Reactor types can include batch or continuous processes. Continuous processes could use intermittent or continuous product discharge. Processes may also include partial or full direct recycle of un-reacted monomer, un-reacted comonomer, and/or diluent.

Polymerization reactor systems of the present invention may comprise one type of reactor in a system or multiple reactors of the same or different type. Production of polymers in multiple reactors may include several stages in at least two separate polymerization reactors interconnected by a transfer device making it possible to transfer the polymers resulting from the first polymerization reactor into the second reactor. The desired polymerization conditions in one of the reactors may be different from the operating conditions of the other reactors. Alternatively, polymerization in multiple reactors may include the manual transfer of polymer from one reactor to subsequent reactors for continued polymerization. Multiple reactor systems may include any combination including, but not limited to, multiple loop reactors, multiple gas reactors, a combination of loop and gas reactors, multiple high pressure reactors or a combination of high pressure with loop and/or gas reactors. The multiple reactors may be operated in series or in parallel.

According to one aspect of the invention, the polymerization reactor system may comprise at least one loop slurry reactor comprising vertical or horizontal loops. Monomer, diluent, catalyst and optionally any comonomer may be continuously fed to a loop reactor where polymerization occurs. Generally, continuous processes may comprise the continuous introduction of a monomer, a catalyst, and a diluent into a polymerization reactor and the continuous removal from this reactor of a suspension comprising polymer particles and the diluent. Reactor effluent may be flashed to remove the solid polymer from the liquids that comprise the diluent, monomer and/or comonomer. Various technologies may be used for this separation step including but not limited to, flashing that may include any combination of heat addition and pressure reduction; separation by cyclonic action in either a cyclone or hydrocyclone; or separation by centrifugation.

A typical slurry polymerization process (also known as the particle form process), is disclosed, for example, in U.S. Pat. Nos. 3,248,179, 4,501,885, 5,565,175, 5,575,979, 6,239,235, 6,262,191 and 6,833,415, each of which is incorporated by reference in its entirety herein.

Suitable diluents used in slurry polymerization include, but are not limited to, the monomer being polymerized and hydrocarbons that are liquids under reaction conditions. Examples of suitable diluents include, but are not limited to, hydrocarbons such as propane, cyclohexane, isobutane, n-butane, n-pentane, isopentane, neopentane, and n-hexane. Some loop polymerization reactions can occur under bulk conditions where no diluent is used. An example is polymerization of propylene monomer as disclosed in U.S. Pat. Nos. 5,455, 314, which is incorporated by reference herein in its entirety.

According to yet another aspect of this invention, the polymerization reactor may comprise at least one gas phase reactor. Such systems may employ a continuous recycle stream containing one or more monomers continuously cycled through a fluidized bed in the presence of the catalyst under polymerization conditions. A recycle stream may be withdrawn from the fluidized bed and recycled back into the reactor. Simultaneously, polymer product may be withdrawn from the reactor and new or fresh monomer may be added to replace the polymerized monomer. Such gas phase reactors may comprise a process for multi-step gas-phase polymerization of olefins, in which olefins are polymerized in the gaseous phase in at least two independent gas-phase polymerization zones while feeding a catalyst-containing polymer formed in a first polymerization zone to a second polymerization zone. One type of gas phase reactor is disclosed in U.S. Pat. Nos. 5,352,749, 4588,790 and 5,436,304, each of which is incorporated by reference in its entirety herein.

According to still another aspect of the invention, a high pressure polymerization reactor may comprise a tubular reactor or an autoclave reactor. Tubular reactors may have several zones where fresh monomer, initiators, or catalysts are added. Monomer may be entrained in an inert gaseous stream and introduced at one zone of the reactor. Initiators, catalysts, and/or catalyst components may be entrained in a gaseous stream and introduced at another zone of the reactor. The gas streams may be intermixed for polymerization. Heat and pressure may be employed appropriately to obtain optimal polymerization reaction conditions.

According to yet another aspect of the invention, the polymerization reactor may comprise a solution polymerization reactor wherein the monomer is contacted with the catalyst composition by suitable stirring or other means. A carrier comprising an inert organic diluent or excess monomer may be employed. If desired, the monomer may be brought in the vapor phase into contact with the catalytic reaction product, in the presence or absence of liquid material. The polymerization zone is maintained at temperatures and pressures that will result in the formation of a solution of the polymer in a reaction medium. Agitation may be employed to obtain better temperature control and to maintain uniform polymerization mixtures throughout the polymerization zone. Adequate means are utilized for dissipating the exothermic heat of polymerization.

Polymerization reactors suitable for the present invention may further comprise any combination of at least one raw material feed system, at least one feed system for catalyst or catalyst components, and/or at least one polymer recovery system. Suitable reactor systems for the present invention may further comprise systems for feedstock purification, catalyst storage and preparation, extrusion, reactor cooling, polymer recovery, fractionation, recycle, storage, loadout, laboratory analysis, and process control.

Conditions that are controlled for polymerization efficiency and to provide resin properties include temperature, pressure and the concentrations of various reactants. Polymerization temperature can affect catalyst productivity, polymer molecular weight and molecular weight distribution. Suitable polymerization temperature may be any temperature below the de-polymerization temperature according to the Gibbs Free energy equation. Typically this includes from about 60° C. to about 280° C., for example, and from about 70° C. to about 110° C., depending upon the type of polymerization reactor.

Suitable pressures will also vary according to the reactor and polymerization type. The pressure for liquid phase polymerizations in a loop reactor is typically less than 1000 psig. Pressure for gas phase polymerization is usually at about 200 to 500 psig. High pressure polymerization in tubular or autoclave reactors is generally run at about 20,000 to 75,000 psig. Polymerization reactors can also be operated in a supercritical region occurring at generally higher temperatures and pressures. Operation above the critical point of a pressure/temperature diagram (supercritical phase) may offer advantages.

The concentration of various reactants can be controlled to produce resins with certain physical and mechanical properties. The proposed end-use product that will be formed by the resin and the method of forming that product determines the desired resin properties. Mechanical properties include tensile, flexural, impact, creep, stress relaxation and hardness tests. Physical properties include density, molecular weight, molecular weight distribution, melting temperature, glass transition temperature, temperature melt of crystallization, density, stereoregularity, crack growth, long chain branching and rheological measurements.

The concentrations of monomer, co-monomer, hydrogen, co-catalyst, modifiers, and electron donors are important in producing these resin properties. Comonomer is used to control product density. Hydrogen can be used to control product molecular weight. Co-catalysts can be used to alkylate, scavenge poisons and control molecular weight. Modifiers can be used to control product properties and electron donors affect stereoregularity. In addition, the concentration of poisons is minimized because poisons impact the reactions and product properties.

The polymer or resin may be formed into various articles, including, but not limited to, bottles, drums, toys, household containers, utensils, film products, drums, fuel tanks, pipes, geomembranes, and liners. Various processes may be used to form these articles, including, but not limited to, blow molding, extrusion molding, rotational molding, thermoforming, cast molding and the like. After polymerization, additives and modifiers can be added to the polymer to provide better processing during manufacturing and for desired properties in the end product. Additives include surface modifiers such as slip agents, antiblocks, tackifiers; antioxidants such as primary and secondary antioxidants; pigments; processing aids such as waxes/oils and fluoroelastomers; and special additives such as fire retardants, antistats, scavengers, absorbers, odor enhancers, and degradation agents.

Homopolymers and copolymers of ethylene produced in accordance with this invention generally have a melt index from about 0.01 to about 100 g/10 min. For example, a melt index in the range from about 0.1 to about 50 g/10 min, or from about 0.5 to about 25 g/10 min, are contemplated in some aspects of this invention.

The density of ethylene-based polymers produced using one or more dinuclear metallocene compounds of the present invention typically falls within the range from about 0.88 to about 0.97 g/cc. In one aspect of this invention, the polymer density is in a range from about 0.90 to about 0.95 g/cc. Yet, in another aspect, the density is generally in a range from about 0.91 to about 0.94 g/cc.

If the resultant polymer produced in accordance with the present invention is, for example, a polymer or copolymer of ethylene, it can be formed into various articles of manufacture. Such articles include, but are not limited to, molded products, household containers, utensils, film or sheet products, drums, fuel tanks, pipes, geomembranes, liners, and the like. Various processes can be employed to form these articles. Non-limiting examples of these processes include injection molding, blow molding, film extrusion, sheet extrusion, profile extrusion, and the like. Additionally, additives and modifiers are often added to these polymers in order to provide beneficial polymer processing or end-use product attributes.

EXAMPLES

The invention is further illustrated by the following examples, which are not to be construed in any way as imposing limitations to the scope of this invention. Various other aspects, embodiments, modifications, and equivalents thereof which, after reading the description herein, may suggest themselves to one of ordinary skill in the art without departing from the spirit of the present invention or the scope of the appended claims.

Nuclear Magnetic Resonance (NMR) spectra were obtained on a Varian Mercury Plus 300 NMR spectrometer operating at 300 MHz for $^1$H NMR (CDCl$_3$ solvent, referenced against the peak of residual CHCl$_3$ at 7.24 ppm) and 75 MHz for $^{13}$C NMR (CDCl$_3$ solvent, referenced against central line of CHCl$_3$ at 77.00 ppm).

In addition to NMR, a thermal desorption mass spectrometry procedure (direct insertion probe mass spectrometry or DIPMS) was used to characterize and identify the dinuclear metallocene compounds in the examples. The mass spectrometer had the following capabilities: 70 ev electron impact ionization, mass range from 35 to 1200 amu, direct probe insertion accessory with maximum temperature to at least 650° C., and software capable of integrating broad peaks typical of probe runs. The method was developed using a Finnigan™ TSQ 7000™ instrument, scan range of 35 to 1400 (1 second scan time), conventional thin wire (with loop at tip) probe tips, source temperature of 180° C., 2×10−6 manifold vacuum, and Finnigan™ Excalibur™ software for peak integration and instrument control. Other instruments having comparable mass range and probe capabilities could be utilized.

In the DIPMS procedure, the sample is placed on the probe tip using a micro syringe. In practice, the smallest drop of sample which can be transferred to the probe usually gives the best results. After placing the sample on the probe, it is allowed to stand for about 5-10 min to allow for evaporation of the bulk of the diluent/solvent containing the compound of interest. Allowing the diluent/solvent to evaporate before inserting the probe into the instrument will, among other things, lessen the chance that the drop will fall off of the tip during the insertion process. After inserting the probe, the temperature program and data acquisition cycles begin. The temperature program used was 50° C. (hold 1 min), 30° C./min temperature ramp, 650° C. final temperature (hold 5 min). This program takes 26 minutes to complete. The filament was turned on 0.5 min into the run and kept on until the completion of the temperature program. After a couple of minutes to allow the probe tip to cool, the probe was removed from the instrument and the analysis cycle was complete.

The Finnigan™ instrument had removable ion volumes; these were changed and cleaned after every two runs to minimize buildup of residue on the lens and other source components. The results are typically outputted as plots showing total ion current versus time.

Melt index (MI, g/10 min) was determined in accordance with ASTM D1238 at 190° C. with a 2,160 gram weight.

High load melt index (HLMI, g/10 min) was determined in accordance with ASTM D1238 at 190° C. with a 21,600 gram weight.

Polymer density was determined in grams per cubic centimeter (g/cc) on a compression molded sample, cooled at about 15° C. per hour, and conditioned for about 40 hours at room temperature in accordance with ASTM D1505 and ASTM D1928, procedure C.

Melt rheological characterizations were determined by methods known to those of skill in the art. For example, small-strain (10%) oscillatory shear measurements were performed on a Rheometrics Scientific, Inc. ARES rheometer using parallel-plate geometry. All rheological tests were performed at 190° C.

Molecular weights and molecular weight distributions were obtained using a PL 220 SEC high temperature chromatography unit (Polymer Laboratories) with trichlorobenzene (TCB) as the solvent, with a flow rate of 1 mL/minute at a temperature of 145° C. BHT (2,6-di-tert-butyl-4-methylphenol) at a concentration of 0.5 g/L was used as a stabilizer in the TCB. An injection volume of 200 µL was used with a nominal polymer concentration of 1.5 mg/mL. Dissolution of the sample in stabilized TCB was carried out by heating at 150° C. for 5 hours with occasional, gentle agitation. The columns used were three PLgel Mixed A LS columns (7.8×300 mm) and were calibrated with a broad linear polyethylene standard (Phillips Marlex® BHB 5003) for which the molecular weight had been determined.

Molecular weight distributions and branch profiles were obtained through size exclusion chromatography (SEC) using an FTIR detector. Chromatographic conditions are those described above. However, the sample injection volume was 500 µL. Samples were introduced to the FTIR detector via a heated transfer line and flow cell (KBr windows, 1 mm optical path, and ca. 70 µL cell volume). The temperatures of the transfer line and flow cell were kept at 143±1° C. and 140±1° C., respectively. A Perkin Elmer FTIR spectrophotometer (PE 2000) equipped with a narrow band mercury cadmium telluride (MCT) detector was used in these studies.

All spectra were acquired using Perkin Elmer Timebase software. Background spectra of the TCB solvent were obtained prior to each run. All IR spectra were measured at 8 cm$^{-1}$ resolution (16 scans). Chromatograms were generated using the root mean square absorbance over the 3000-2700 cm$^{-1}$ spectral region (i.e., FTIR serves as a concentration detector). Molecular weight calculations were made as previously described using a broad molecular weight polyethylene (PE) standard [see Jordens K, Wilkes G L, Janzen J, Rohlfing D C, Welch M B, Polymer 2000; 41:7175]. Spectra from individual time slices of the chromatogram were subsequently analyzed for comonomer branch levels using chemometric techniques. All calibration spectra were taken at sample concentrations which far exceeded that needed for good signal to noise (i.e., >0.08 mg/mL at the detector).

Branching content was determined as follows. Narrow molecular weight (weight-average molecular weight to number-average molecular weight ratio ($M_w/M_n$) of about 1.1 to 1.3), solvent gradient fractions of ethylene 1-butene, ethylene 1-hexene, polyethylene homopolymers, and low molecular weight alkanes were used in calibration and verification studies. The total methyl content of these samples ranged from 1.4 to 82.7 methyls per 1000 total carbons. Methyl content of samples was calculated from $M_n$ or measured using C-13 NMR spectroscopy. C-13 NMR spectra were obtained on 15 weight percent samples in TCB using a 500 MHz Varian Unity Spectometer run at 125° C. as previous described [see Randall J C, Hsieh E T, NMR and Macromolecules; Sequence, Dynamic, and Domain Structure, ACS Symposium Series 247, J. C. Randall, Ed., American Chemical Society, Washington D.C., 1984.]. Methyl content per 1000 carbons by NMR was obtained by multiplying (times 1000) the ratio of total methyl signals to total signal intensity.

A partial least squares (PLS) calibration curve was generated using Pirouette chemometric software (Infometrix) to correlate changes in the FTIR absorption spectra with calculated or NMR measured values for methyls/1000 total carbons for 25 samples. The FTIR absorption spectra used in the calibration model were made from co-added spectra collected across the whole sample. Only a portion of the spectral region (2996 and 2836 cm$^{-1}$) was used in the calibration step in order to minimize the effects of residual solvent absorption. Preprocessing of spectral data included area normalization, taking the first derivative of the spectra and mean centering all data.

A four component calibration model was calculated and optimized using the process of cross validation (RSQ=0.999, SEV=0.7). The calibration model was verified using 23 additional samples. The predicted versus actual values for the validation data showed excellent correlation (RSQ=0.987) and exhibited a root mean square error of prediction equal to +/−0.4 methyl groups per 1000 total carbon molecules.

Short chain branching levels were calculated by subtracting out methyl chain end contributions. The amount of methyl chain ends were calculated using the equation $Me_{ce}=C(2-V_{ce})/M_s$, where $Me_{ce}$ is the number of methyl chain ends per 1000 total carbon molecules, C is a constant equal to 14000, $V_{ce}$ is the number of vinyl terminated chain ends (e.g., 1 for chromium catalyzed resins), and $M_s$ is the molecular weight calculated for a particular slice of the molecular weight distribution.

Sulfated alumina was formed by a process wherein alumina was chemically-treated with a sulfate or bisulfate source. Such a sulfate or bisulfate source may include, for example, sulfuric acid, ammonium sulfate, or ammonium bisulfate. In an exemplary procedure, a commercial alumina sold as W.R. Grace Alumina A was sulfated by impregnation with an aqueous solution containing about 15-20% $(NH_4)_2SO_4$ or $H_2SO_4$. This sulfated alumina was calcined at 550° C. in air (240° C./hr ramp rate), with a 3 hr hold period at this temperature. Afterward, the sulfated alumina was collected and stored under dry nitrogen, and was used without exposure to the atmosphere.

Example 1

Synthesis of bis[dichlorohafnium(diphenylmethylidene($\eta^5$-9-2,7-di-tert-butylfluorenyl)($\eta^5$-3-cyclopentadienyl)]1,8-oct-4-ene, $C_{86}H_{88}Hf_2Cl_4$(DMET 1), using olefin metathesis DMET 1 is a nano-linked, dinuclear compound of the presented invention. It is produced using a single metallocene reactant and is, therefore, a homonuclear compound. The reactant metallocene used to produce DMET 1 is diphenylmethylidene($\eta^5$-(3-(penten-4-yl)cyclopentadienyl)($\eta^5$-9-2,7-di-tert-butylfluorenyl)hafnium dichloride (abbreviated "MET 1"). The reaction scheme for this inventive example is illustrated below (Ph=Phenyl):

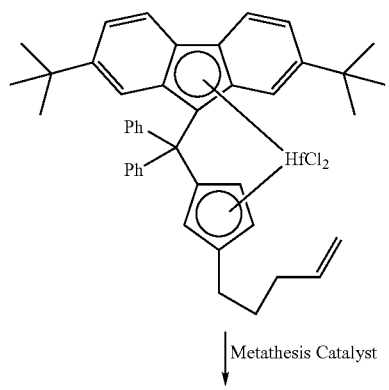

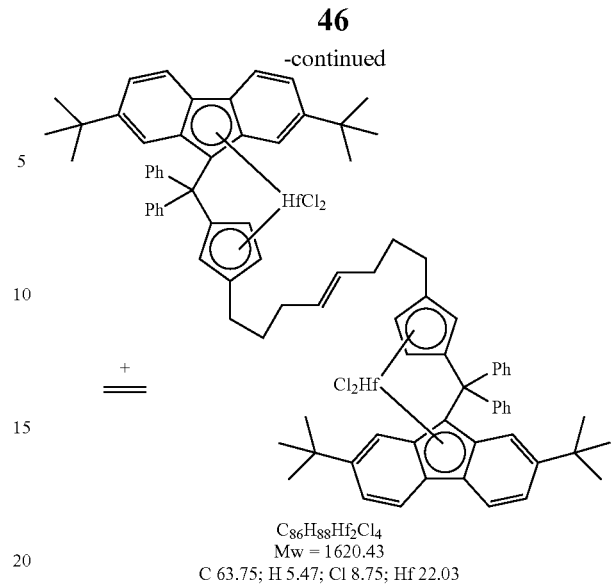

$C_{86}H_{88}Hf_2Cl_4$
Mw = 1620.43
C 63.75; H 5.47; Cl 8.75; Hf 22.03

The MET 1 metallocene starting material can be prepared in accordance with suitable methods. One such technique is described in U.S. Patent Publication No. 2007-0179044, the disclosure of which is incorporated herein by reference in its entirety.

Approximately 2 mg of bis(tricyclohexylphosphine)benzylidine ruthenium (IV) dichloride (Grubbs first generation metathesis catalyst) were charged to a reactor under an inert nitrogen atmosphere. After about 100 mg of MET 1 were added to the reactor, approximately 2 mL of benzene-d6 were added via syringe. The reaction was allowed to proceed at ambient temperature. Initially, a yellow solution resulted and ethylene was released from the reaction mixture. As the reaction proceeded, the reaction mixture became a turbid yellow color. After 2 days, a sample of the reaction product was removed, and utilized in Example 2.

After 6 days, approximately 3.75 mg of ruthenium catalyst in 1 mL of benzene-d6 were added to the reaction product remaining in the reactor. After a total of 34 days at a temperature of around 30° C., the solid reaction product was removed from the reactor. A sample of this reaction product was dissolved in D-chloroform to form a solution for analysis by 1H-NMR. NMR confirmed the presence of the desired dinuclear compound, DMET 1, as illustrated in FIG. 1.

Example 2

Hydrolysis of DMET 1, $C_{86}H_{88}Hf_2Cl_4$, to the Free Ligand, $C_{86}H_{92}$ Although the conversion to DMET 1 was slow in Example 1, mass spectrometry also confirmed the presence of the desired dinuclear compound, DMET 1. A portion of the reaction product after 2 days from Example 1 was used as the starting material for Example 2.

Approximately 25 mg of the solid DMET 1 reaction product of Example 1 were placed in a vial and hydrolyzed using about 10 microliters of water in about 0.5 mL of toluene. The metal was hydrolyzed to the free ligand ($C_{86}H_{92}$) and the ligand having the following structure was subsequently characterized:

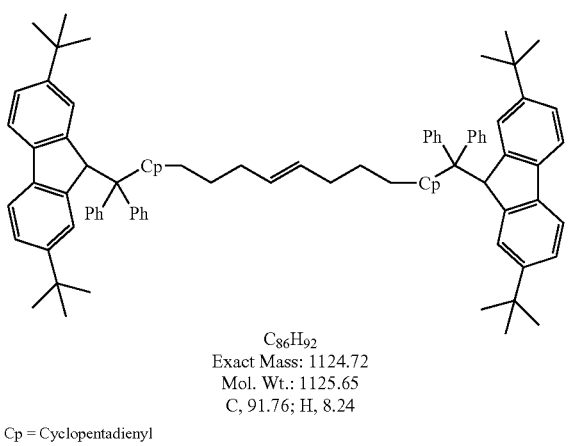

C<sub>86</sub>H<sub>92</sub>
Exact Mass: 1124.72
Mol. Wt.: 1125.65
C, 91.76; H, 8.24

Cp = Cyclopentadienyl

Figure 2:
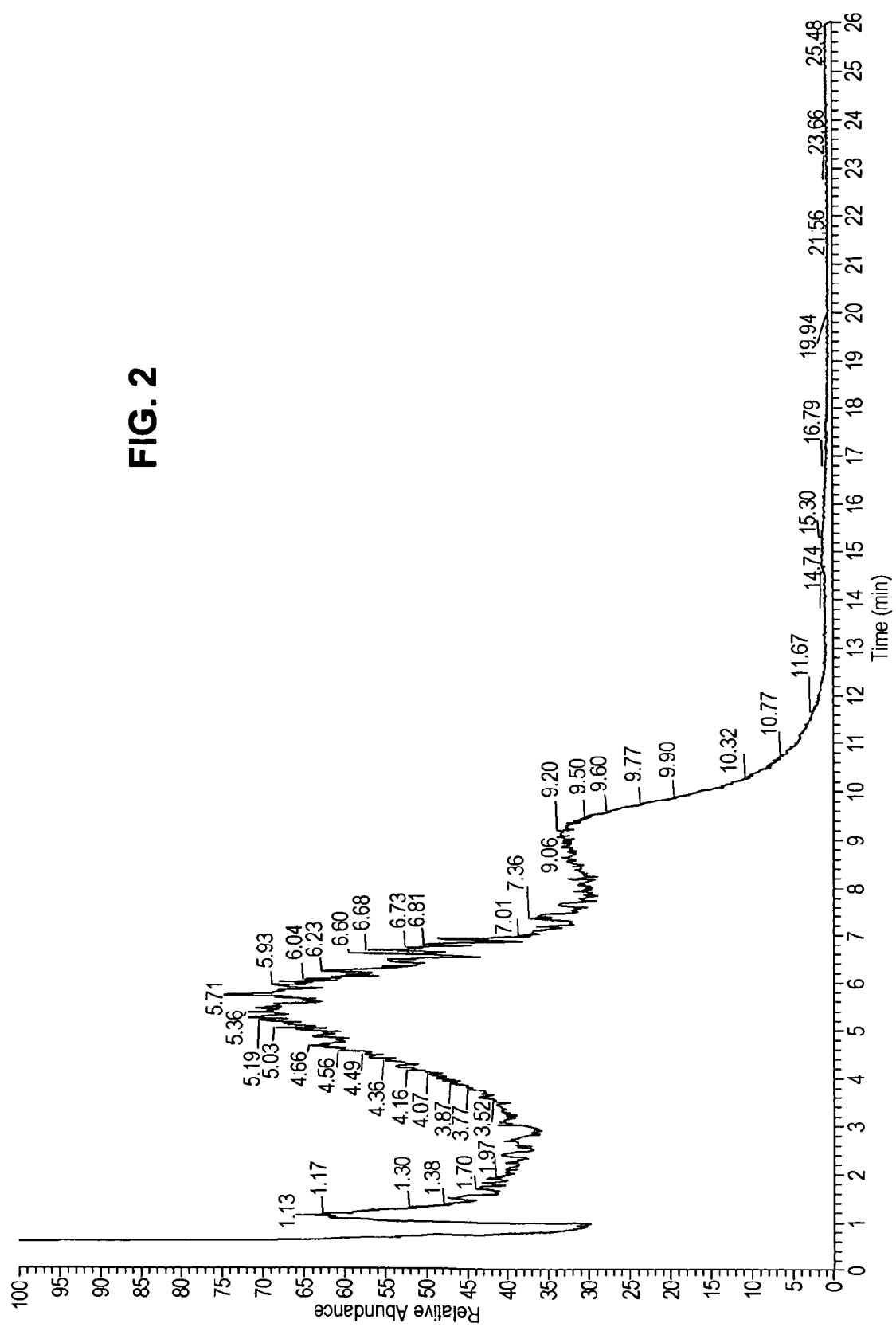
FIG. 2 presents a mass spectrum probe evolution plot of Example 2.
Figure 3:
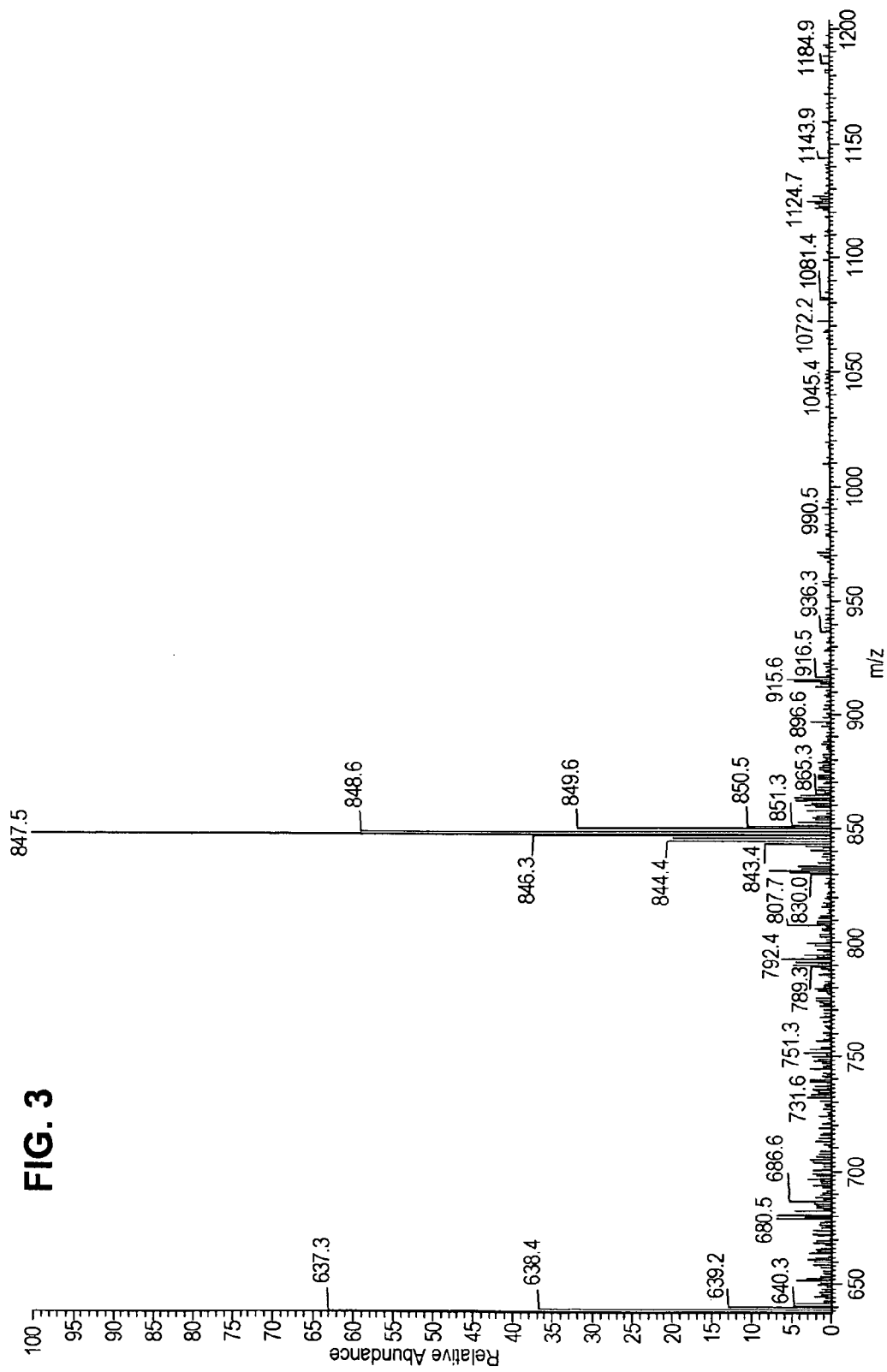
FIG. 3 presents an expanded mass spectrum plot of Example 2.

This compound was analyzed using the thermal desorption mass spectrometry procedure, DIPMS, outlined above. In FIG. 2, the peak at about 9 min is the desired product. As illustrated in FIG. 3, the prominent molecular ion observed was consistent with the expected molecular mass of about 1124 Daltons of the free ligand.

Examples 3-7

Polymerization Runs Using a Catalyst System Based on Dinuclear Metallocene DMET 1

Dinuclear metallocene compounds of the present invention were used as part of a catalyst system to polymerize olefins. All polymerizations were conducted in a one-gallon stainless steel semi-batch reactor. Two liters of isobutane and alkyl aluminum co-catalyst were used in all polymerization experiments. The typical polymerization procedure was conducted as follows: alkyl aluminum, the activator-support and the metallocene were added in order through a charge port while venting isobutane vapor. The charge port was closed and about 2 liters of isobutane were added. The contents of the reactor were stirred and heated to the desired run temperature, and ethylene was then introduced along with the desired amount of hexene. Ethylene was fed on demand to maintain the specified pressure for the specified length of the polymerization run. The reactor was maintained and controlled at the desired run temperature throughout the polymerization. Upon completion, the ethylene flow was stopped and the reactor pressure slowly vented off. The reactor was opened and the polymer product was collected and dried under vacuum at approximately 50° C. for at least two hours.

Ethylene/1-hexene copolymers were produced using the dinuclear metallocene product of Example 1, DMET 1. The specific polymerization conditions employed were a 60 minute run time, reaction temperature of 95° C., 420 psig ethylene feed, and 10 grams of 1-hexene with either 0.2 or 0.5 mmol of triisobutylaluminum (TIBA) per 100 mg of sulfated alumina. In some cases, hydrogen was also introduced into the reactor. Table I summarizes the catalyst system formulations and the amount of ethylene/hexene copolymer produced in Examples 3-7.

TABLE I

Examples 3-7 using DMET 1 dinuclear compound.

| Example | Catalyst | mg Catalyst | mmol TIBA | mg hydrogen | mg A-S | g PE |
|---------|----------|-------------|-----------|-------------|--------|------|
| 3 | DMET 1 | 1 | 0.2 | N/A | 103 | 16 |
| 4 | DMET 1 | 1 | 0.2 | N/A | 102 | 32 |
| 5 | DMET 1 | 1 | 0.5 | N/A | 106 | 22 |
| 6 | DMET 1 | 1 | 0.5 | 17 | 108 | 40 |
| 7 | DMET 1 | 2.5 | 0.5 | 17 | 107 | 35 |

Notes on Table I:

mg A-S - milligrams of sulfated alumina activator-support.

g PE - grams ethylene/hexene copolymer produced.

mg hydrogen determined by means of PV = nRT.

We claim:

1. A compound represented by any of the following structures:

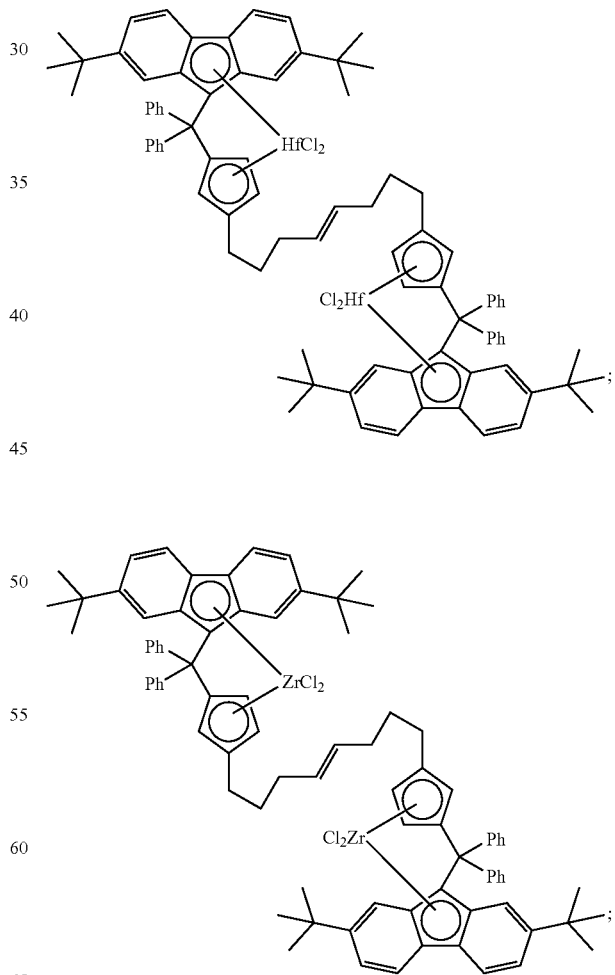

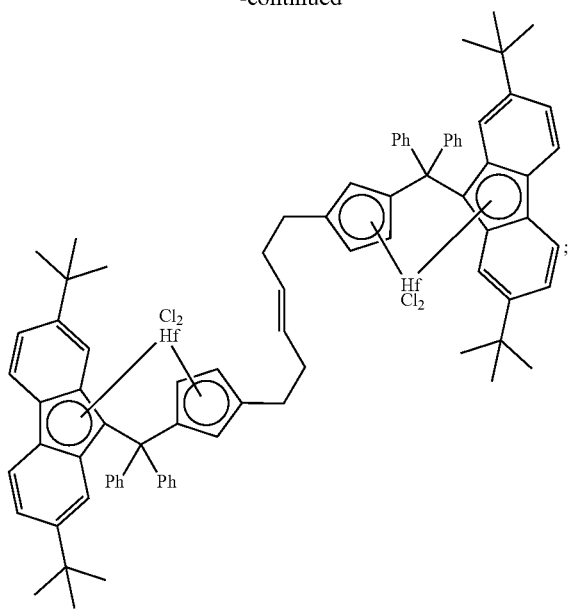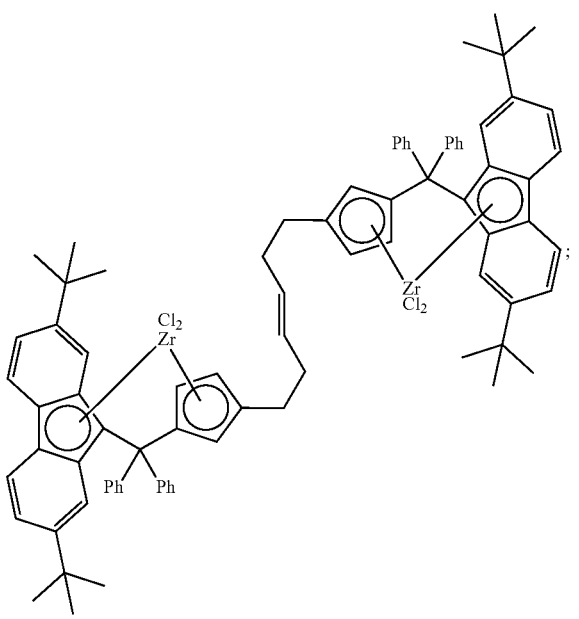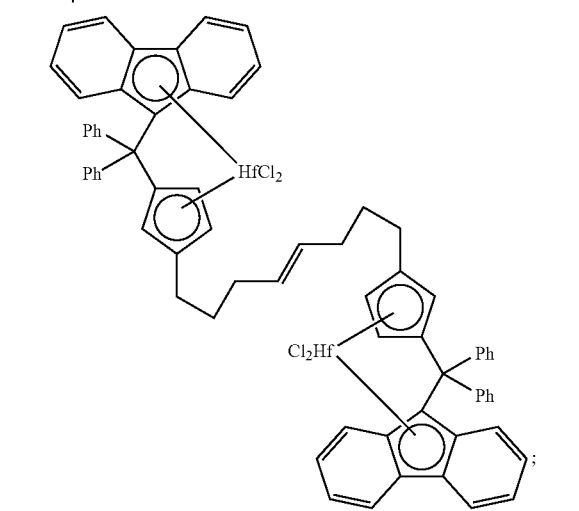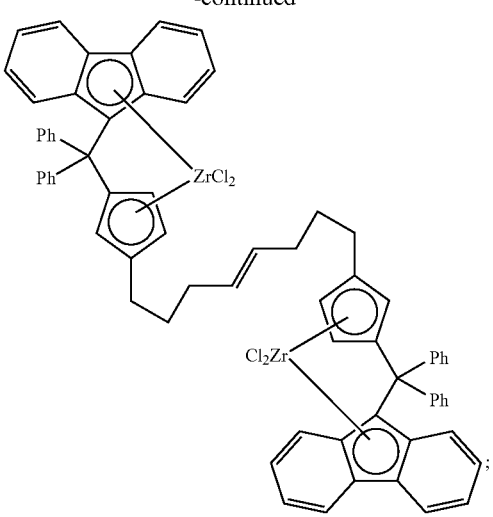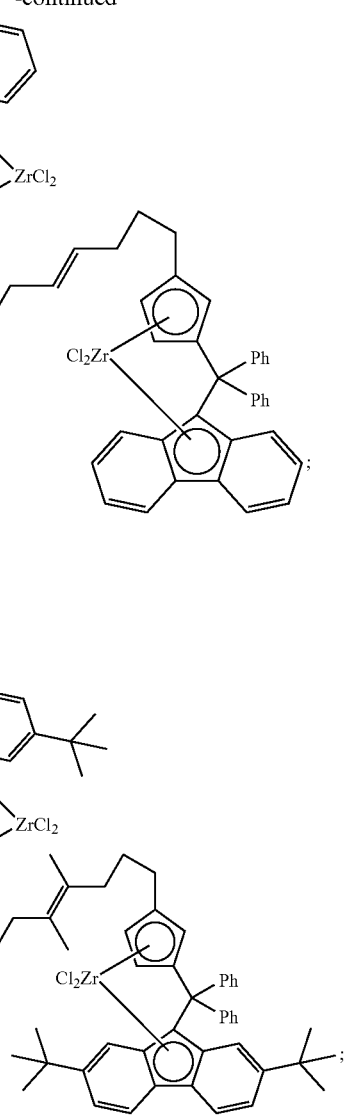

-continued
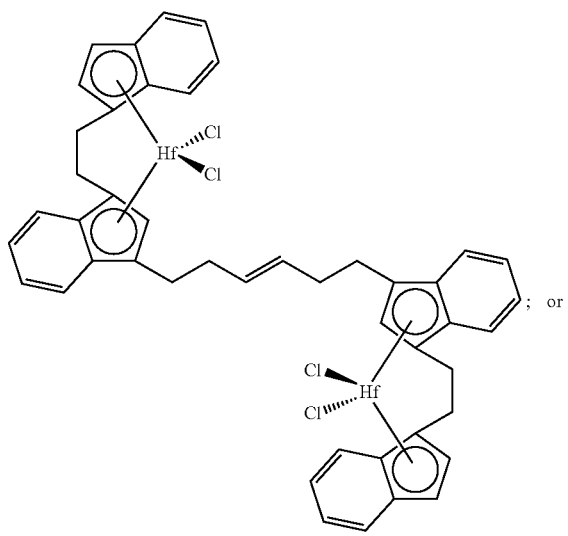
; or
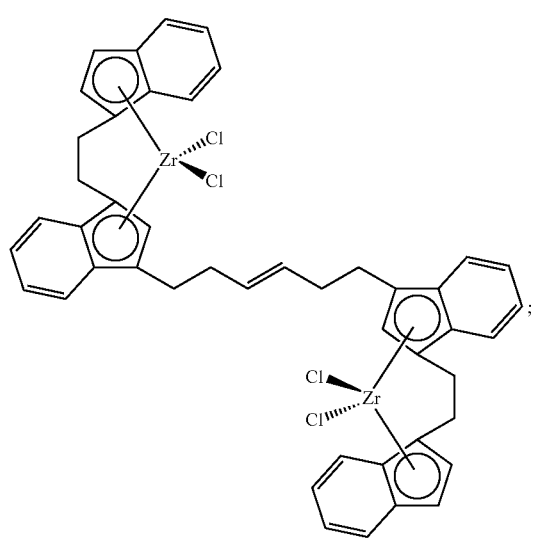
;
wherein Ph is an abbreviation for phenyl.
2. The compound of claim 1, wherein the compound is:
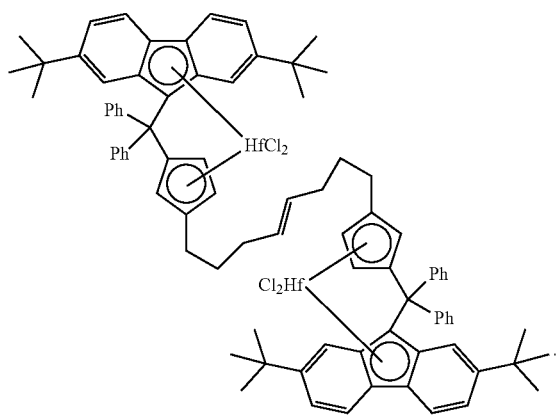
3. The compound of claim 1, wherein the compound is:
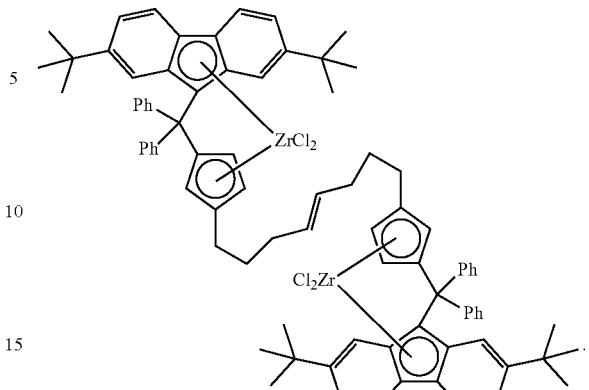
4. The compound of claim 1, wherein the compound is:
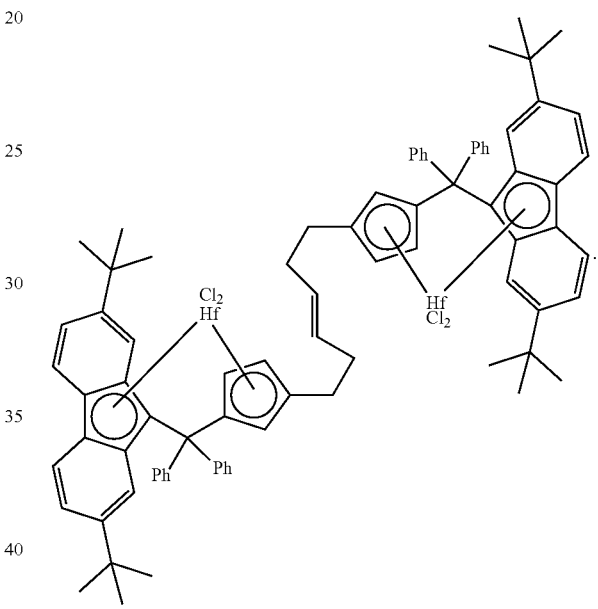
5. The compound of claim 1, wherein the compound is:
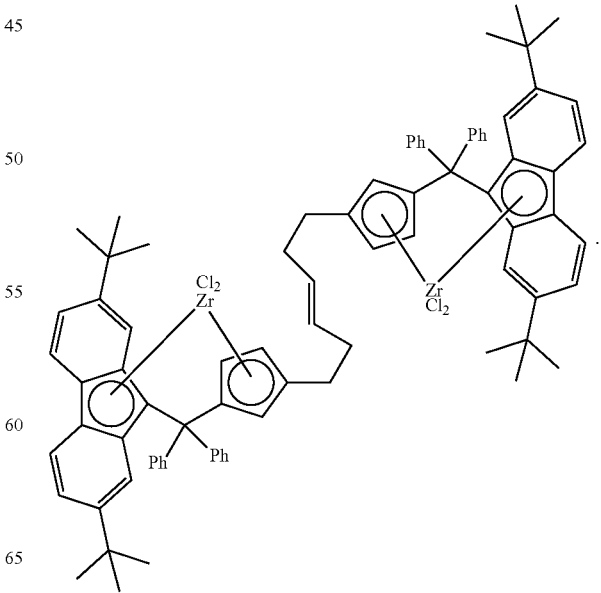

6. The compound of claim 1, wherein the compound is:
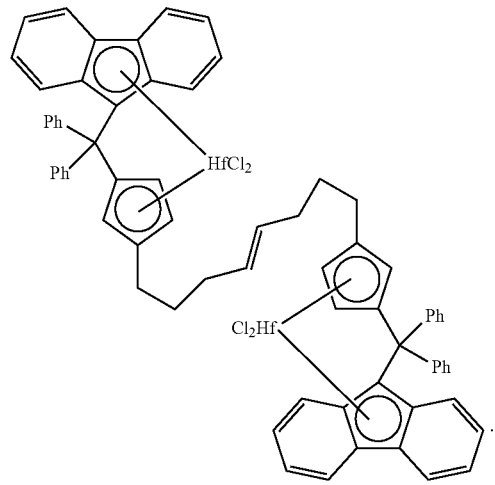
7. The compound of claim 1, wherein the compound is:
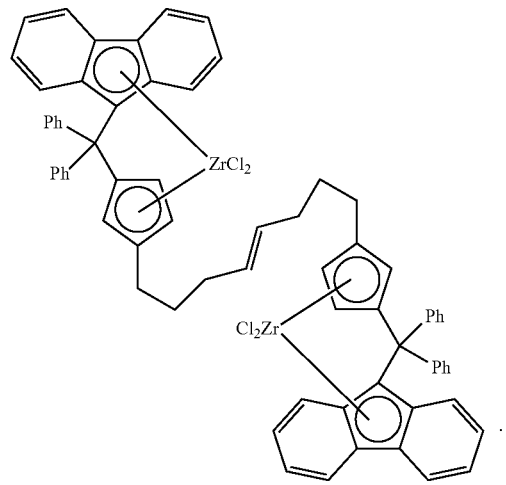
8. The compound of claim 1, wherein the compound is:
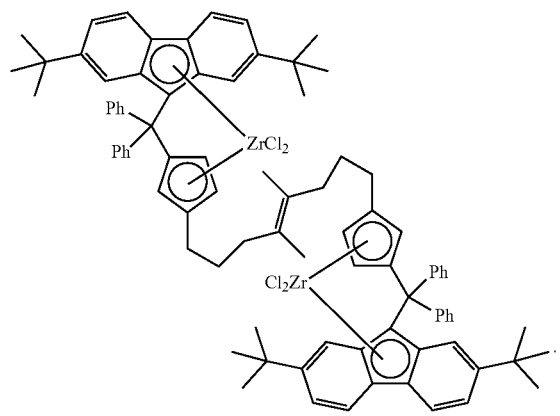
9. The compound of claim 1, wherein the compound is:
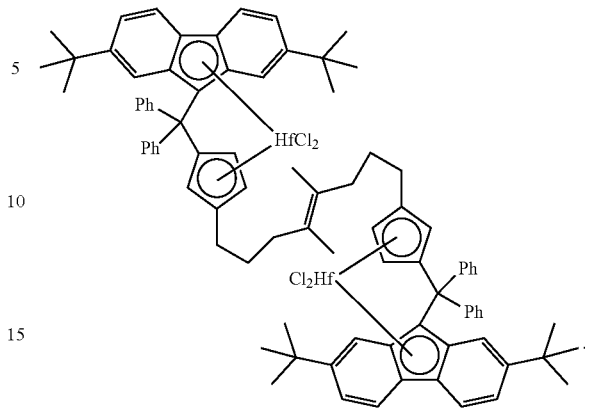
10. The compound of claim 1, wherein the compound is:
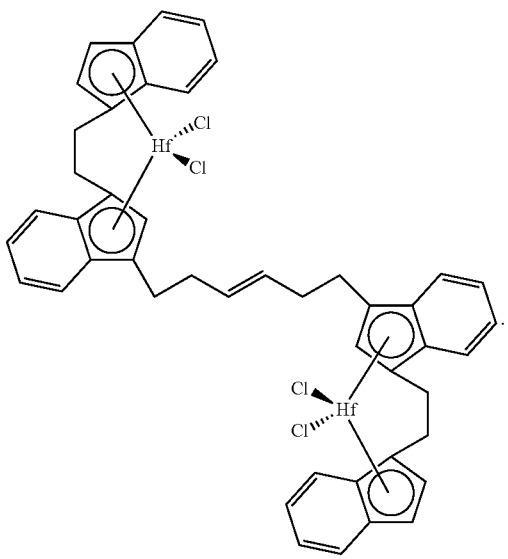
11. The compound of claim 1, wherein the compound is:
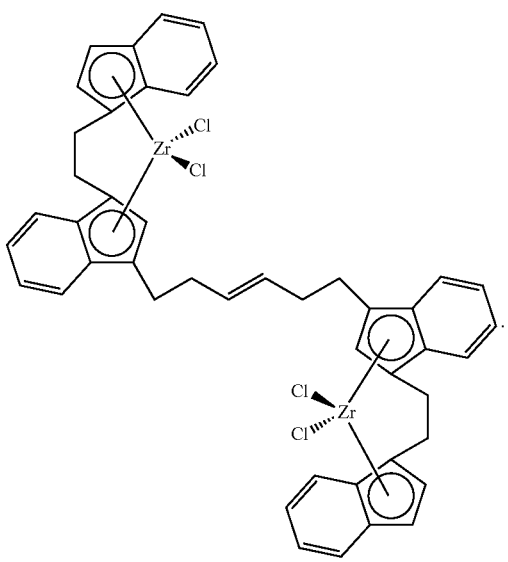

12. A catalyst composition comprising a contact product of at least one dinuclear metallocene compound and at least one activator-support,
wherein the at least one dinuclear metallocene compound is:
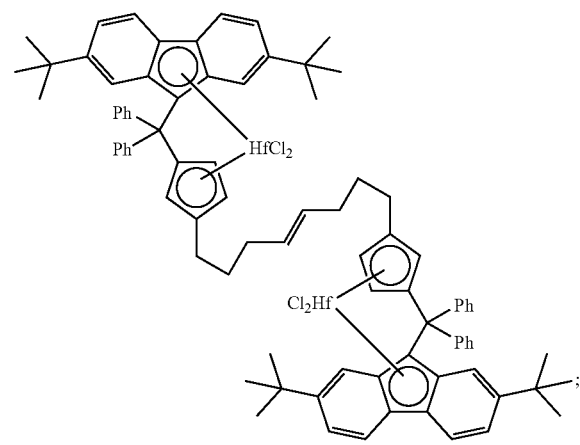
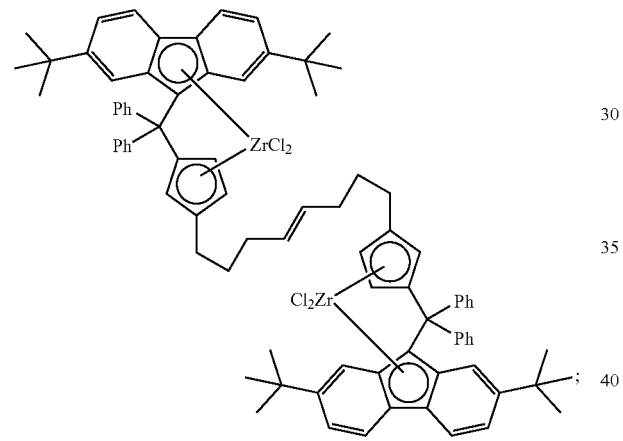
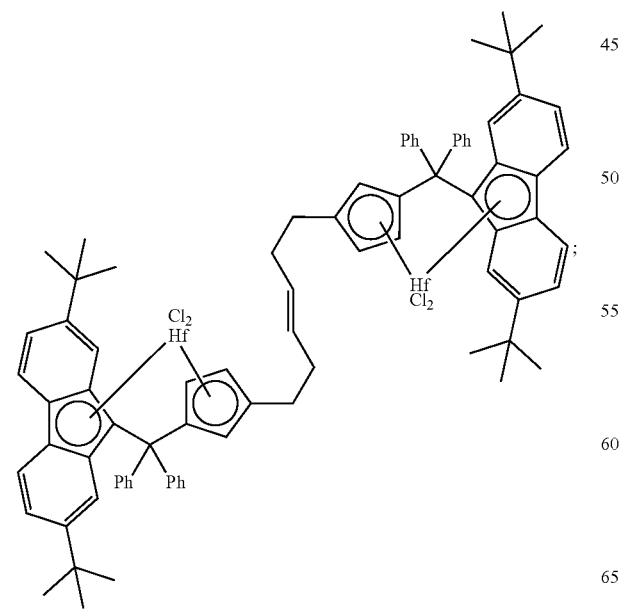
-continued
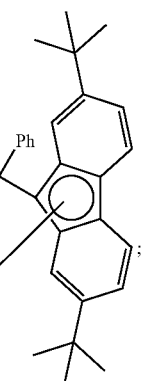
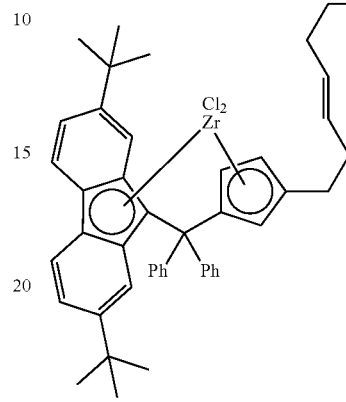
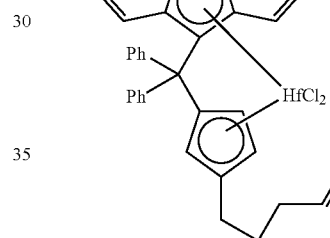
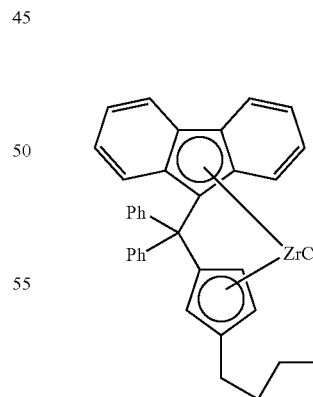
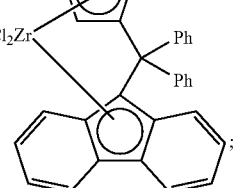

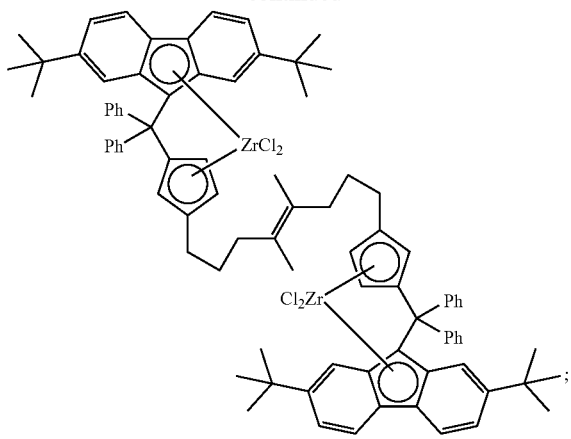

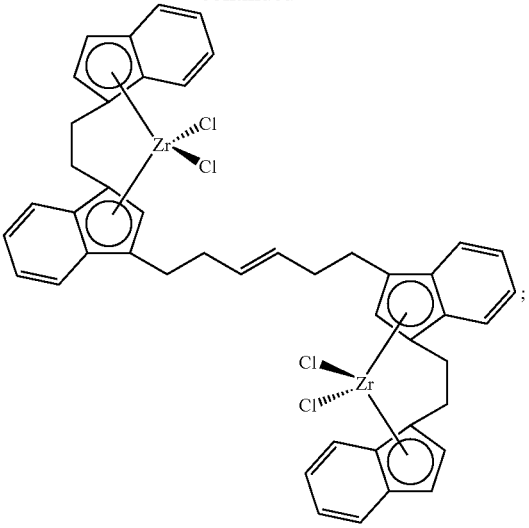

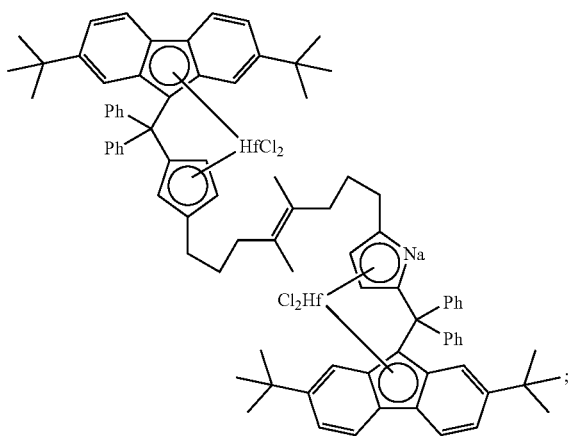

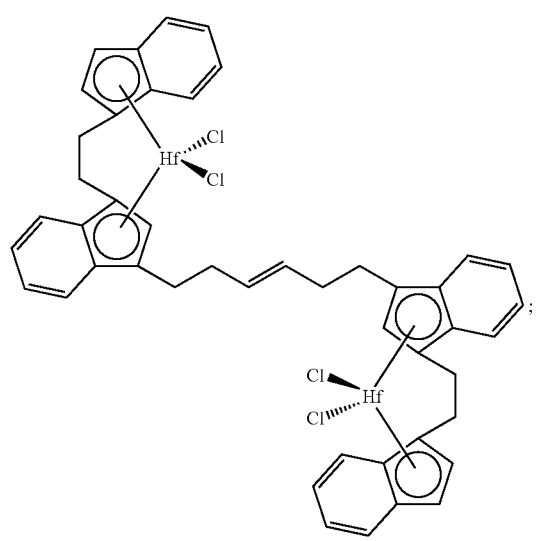

or a combination thereof, wherein Ph is an abbreviation for phenyl.

13. The catalyst composition of claim 12, wherein the at least one activator-support is fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, or any combination thereof.

14. The catalyst composition of claim 12, wherein the at least one activator-support comprises a solid oxide treated with an electron-withdrawing anion, wherein:
the solid oxide is silica, alumina, silica-alumina, aluminum phosphate, heteropolytungstate, titania, zirconia, magnesia, boria, zinc oxide, any mixed oxides thereof, or any mixture thereof; and
the electron-withdrawing anion is fluoride, chloride, bromide, phosphate, triflate, bisulfate, sulfate, or any combination thereof.

15. The catalyst composition of claim 12, wherein the at least one activator-support further comprises a metal or metal ion, and wherein the metal or metal ion is zinc, nickel, vanadium, silver, copper, gallium, tin, tungsten, molybdenum, or any combination thereof.

16. The catalyst composition of claim 12, wherein the at least one activator-support comprises a clay mineral, a pillared clay, an exfoliated clay, an exfoliated clay gelled into another oxide matrix, a layered silicate mineral, a non-layered silicate mineral, a layered aluminosilicate mineral, a non-layered aluminosilicate mineral, or any combination thereof.

17. The catalyst composition of claim 12, further comprising at least one organoaluminum compound having the formula:

$$Al(X^5)_m(X^6)_{3-m};$$

wherein:
$X^5$ is a hydrocarbyl;
$X^6$ is an alkoxide or an aryloxide, a halide, or a hydride; and
m is from 1 to 3, inclusive.

18. The catalyst composition of claim 12, further comprising at least one organoaluminum compound, wherein the at least one organoaluminum compound is trimethylaluminum, triethylaluminum, tri-n-propylaluminum, diethylaluminum ethoxide, tri-n-butylaluminum, diisobutylaluminum hydride, triisobutylaluminum, diethylaluminum chloride, or any combination thereof.

19. The catalyst composition of claim 12, further comprising at least one optional co-catalyst, wherein the at least one optional co-catalyst is at least one aluminoxane compound, at least one organozinc compound, at least one organoboron or organoborate compound, at least one ionizing ionic compound, or any combination thereof.

20. A process for polymerizing olefins comprising contacting the catalyst composition of claim 12 with at least one olefin monomer and optionally at least one olefin comonomer under polymerization conditions to produce a polymer or copolymer.

21. The process of claim 20, wherein the at least one olefin monomer comprises ethylene, propylene, or styrene.

22. The process of claim 20, wherein the at least one olefin monomer comprises ethylene and the at least one olefin comonomer comprises 1-butene, 2-butene, 3-methyl-1-butene, isobutylene, 1-pentene, 2-pentene, 3-methyl-1-pentene, 4-methyl-1-pentene, 1-hexene, 2-hexene, 3-ethyl-1-hexene, 1-heptene, 2-heptene, 3-heptene, 1-octene, styrene, or mixtures thereof.

23. The process of claim 20, wherein the process is conducted in a polymerization reactor system comprising a slurry reactor, a loop slurry reactor, a gas phase reactor, a fluidized bed reactor, a solution reactor, a tubular reactor, an autoclave reactor, or any combination thereof.

24. The process of claim 20, wherein the catalyst composition further comprises at least one organoaluminum compound, wherein the at least one organoaluminum compound is trimethylaluminum, triethylaluminum, tri-n-propylaluminum, diethylaluminum ethoxide, tri-n-butylaluminum, diisobutylaluminum hydride, triisobutylaluminum, diethylaluminum chloride, or any combination thereof; and
  wherein the at least one activator-support is fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, or any combination thereof.

25. A catalyst composition comprising a contact product of at least one dinuclear metallocene compound and at least one compound selected from at least one aluminoxane compound, at least one organozinc compound, at least one organoboron or organoborate compound, at least one ionizing ionic compound, or any combination thereof;
  wherein the at least one dinuclear metallocene compound is:

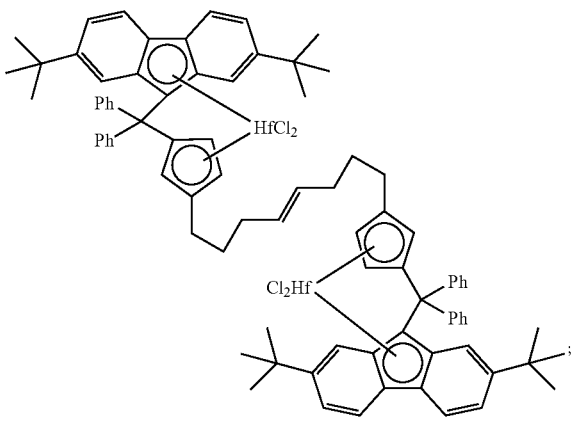

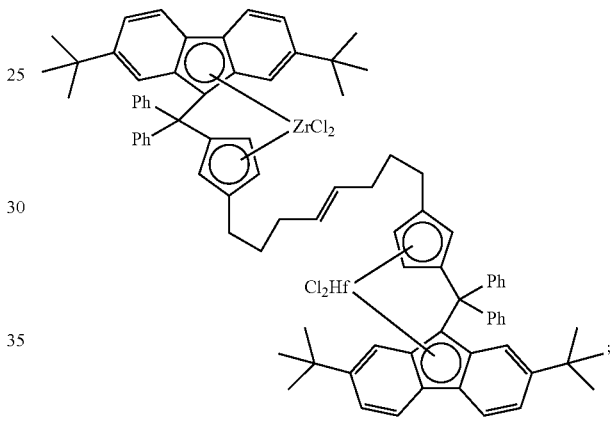

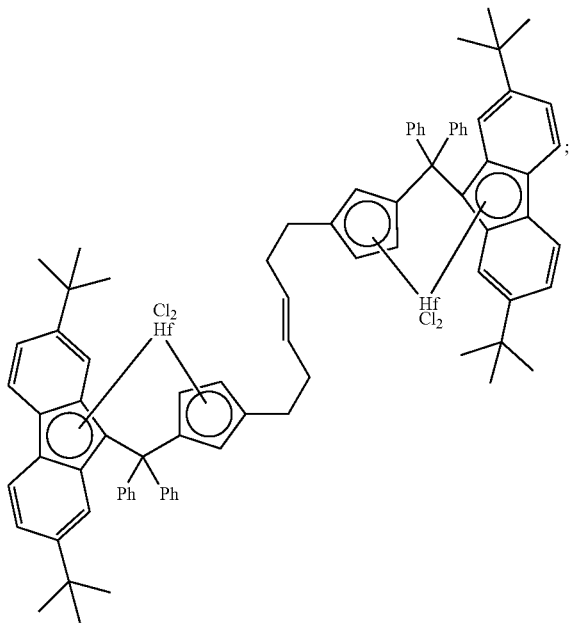

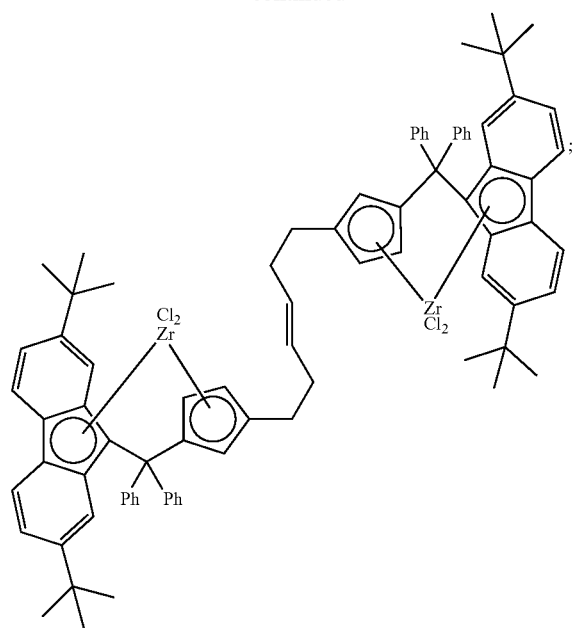
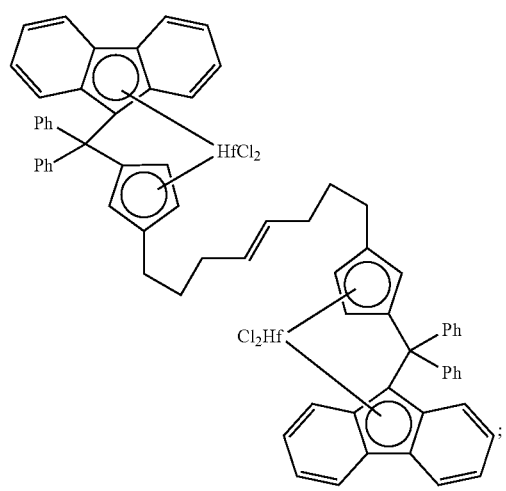
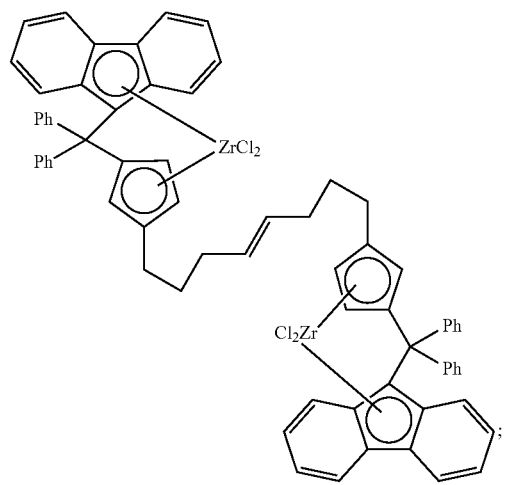
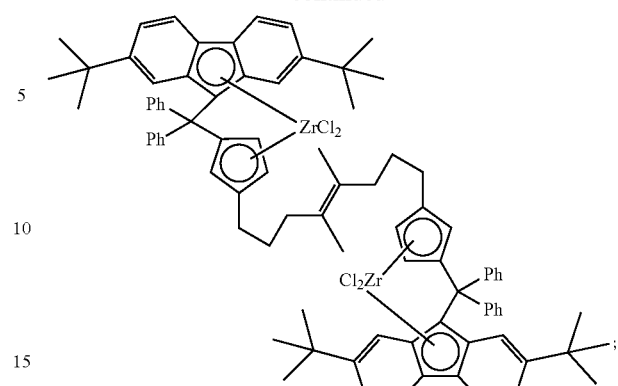
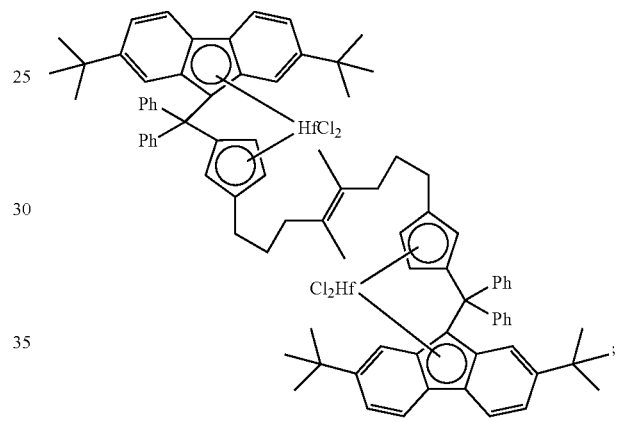
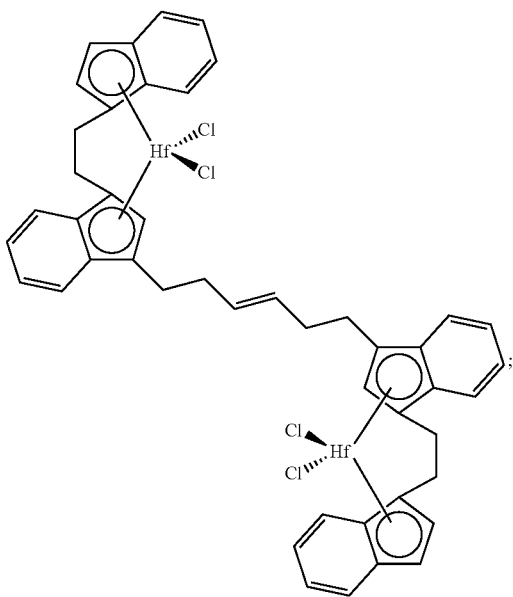

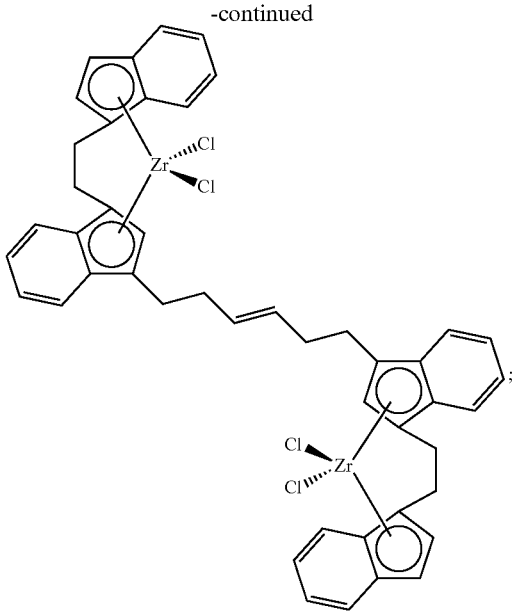

or a combination thereof, wherein Ph is an abbreviation for phenyl.

26. The catalyst composition of claim 25, wherein the at least one compound is at least one aluminoxane compound, and the at least one aluminoxane compound comprises:
(a) a cyclic aluminoxane having the formula:

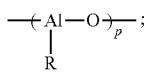

wherein:
R is a linear or branched alkyl having from 1 to 10 carbon atoms; and
p is an integer from 3 to 20;
(b) a linear aluminoxane having the formula:

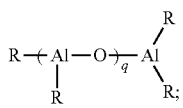

wherein:
R is a linear or branched alkyl having from 1 to 10 carbon atoms; and
q is an integer from 1 to 50;
(c) a cage aluminoxane having the formula $R_{5r+\alpha}{}^{t}R_{r-\alpha}{}^{b}Al_{4r}O_{3r}$, wherein:
$R^{t}$ is a terminal linear or branched alkyl group having from 1 to 10 carbon atoms;
$R^{b}$ is a bridging linear or branched alkyl group having from 1 to 10 carbon atoms;
r is 3 or 4; and
α is equal to $n_{Al(3)}-n_{O(2)}+n_{O(4)}$, wherein $n_{Al(3)}$ is the number of three coordinate aluminum atoms, $n_{O(2)}$ is the number of two coordinate oxygen atoms, and $n_{O(4)}$ is the number of 4 coordinate oxygen atoms; or
any combination thereof.

27. The catalyst composition of claim 25, wherein the at least one compound is at least one organoboron or organoborate compound, and the at least one organoboron or organoborate compound is N,N-dimethylanilinium tetrakis(pentafluorophenyl)borate, lithium tetrakis(pentafluorophenyl)borate, triphenylcarbenium tetrakis(pentafluorophenyl)borate, N,N-dimethylanilinium tetrakis[3,5-bis(trifluoromethyl)phenyl]borate, triphenylcarbenium tetrakis[3,5-bis(trifluoromethyl)phenyl]borate, tris(pentafluorophenyl)boron, tris[3,5-bis(trifluoromethyl)phenyl]boron, or any combination thereof.

28. The catalyst composition of claim 25, wherein the at least one compound is at least one ionizing ionic compound, and the at least one ionizing ionic compound is tri(n-butyl)ammonium tetrakis(p-tolyl)borate, tri(n-butyl)ammonium tetrakis(m-tolyl)borate, tri(n-butyl)ammonium tetrakis(2,4-dimethyl)borate, tri(n-butyl)ammonium tetrakis(3,5-dimethylphenyl)borate, tri(n-butyl)ammonium tetrakis[3,5-bis(trifluoromethyl)phenyl]borate, tri(n-butyl)ammonium tetrakis(pentafluorophenyl)borate, N,N-dimethylanilinium tetrakis(p-tolyl)borate, N,N-dimethylanilinium tetrakis(m-tolyl)borate, N,N-dimethylanilinium tetrakis(2,4-dimethylphenyl)borate, N,N-dimethylanilinium tetrakis(3,5-dimethylphenyl)borate, N,N-dimethylanilinium tetrakis[3,5-bis(trifluoromethyl)phenyl]borate, N,N-dimethylanilinium tetrakis(pentafluorophenyl)borate, triphenylcarbenium tetrakis(p-tolyl)borate, triphenylcarbenium tetrakis(m-tolyl)borate, triphenylcarbenium tetrakis(2,4-dimethylphenyl)borate, triphenylcarbenium tetrakis(3,5-dimethylphenyl)borate, triphenylcarbenium tetrakis[3,5-bis(trifluoromethyl)phenyl]borate, triphenylcarbenium tetrakis(pentafluorophenyl)borate, tropylium tetrakis(p-tolyl)borate, tropylium tetrakis(m-tolyl)borate, tropylium tetrakis(2,4-dimethylphenyl)borate, tropylium tetrakis(3,5-dimethylphenyl)borate, tropylium tetrakis[3,5-bis(trifluoromethyl)phenyl]borate, tropylium tetrakis(pentafluorophenyl)borate, lithium tetrakis(pentafluorophenyl)borate, lithium tetraphenylborate, lithium tetrakis(p-tolyl)borate, lithium tetrakis(m-tolyl)borate, lithium tetrakis(2,4-dimethylphenyl)borate, lithium tetrakis(3,5-dimethylphenyl)borate, lithium tetrafluoroborate, sodium tetrakis(pentafluorophenyl)borate, sodium tetraphenylborate, sodium tetrakis(p-tolyl)borate, sodium tetrakis(m-tolyl)borate, sodium tetrakis(2,4-dimethylphenyl)borate, sodium tetrakis(3,5-dimethylphenyl)borate, sodium tetrafluoroborate, potassium tetrakis(pentafluorophenyl)borate, potassium tetraphenylborate, potassium tetrakis(p-tolyl)borate, potassium tetrakis(m-tolyl)borate, potassium tetrakis(2,4-dimethylphenyl)borate, potassium tetrakis(3,5-dimethylphenyl)borate, potassium tetrafluoroborate, lithium tetrakis(pentafluorophenyl)aluminate, lithium tetraphenylaluminate, lithium tetrakis(p-tolyl)aluminate, lithium tetrakis(m-tolyl)aluminate, lithium tetrakis(2,4-dimethylphenyl)aluminate, lithium tetrakis(3,5-dimethylphenyl)aluminate, lithium tetrafluoroaluminate, sodium tetrakis(pentafluorophenyl)aluminate, sodium tetraphenylaluminate, sodium tetrakis(p-tolyl)aluminate, sodium tetrakis(m-tolyl)aluminate, sodium tetrakis(2,4-dimethylphenyl)aluminate, sodium tetrakis(3,5-dimethylphenyl)aluminate, sodium tetrafluoroaluminate, potassium tetrakis(pentafluorophenyl)aluminate, potassium tetraphenylaluminate, potassium tetrakis(p-tolyl)aluminate, potassium tetrakis(m-tolyl)aluminate, potassium tetrakis(2,4-dimethylphenyl)aluminate, potassium tetrakis(3,5-dimethylphenyl)aluminate, potassium tetrafluoroaluminate, or any combination thereof.

29. A process for polymerizing olefins comprising contacting the catalyst composition of claim 25 with at least one olefin monomer and optionally at least one olefin comonomer under polymerization conditions to produce a polymer or copolymer.

30. The process of claim 29, wherein the at least one olefin monomer comprises ethylene, propylene, or styrene.

31. The process of claim 29, wherein the at least one olefin monomer comprises ethylene and the at least one olefin comonomer comprises 1-butene, 2-butene, 3-methyl-1-butene, isobutylene, 1-pentene, 2-pentene, 3-methyl-1-pentene, 4-methyl-1-pentene, 1-hexene, 2-hexene, 3-ethyl-1-hexene, 1-heptene, 2-heptene, 3-heptene, 1-octene, styrene, or mixtures thereof.

32. The process of claim 29, wherein the process is conducted in a polymerization reactor system comprising a slurry reactor, a loop slurry reactor, a gas phase reactor, a fluidized bed reactor, a solution reactor, a tubular reactor, an autoclave reactor, or any combination thereof.

* * * * *